US011851410B2

(12) United States Patent
Gunning et al.

(10) Patent No.: US 11,851,410 B2
(45) Date of Patent: Dec. 26, 2023

(54) SENSORS FOR DETECTION OF NEGATIVELY CHARGED PHOSPHATE-CONTAINING MEMBRANES AND MEMBRANE COMPONENTS

(71) Applicant: THE GOVERNING COUNCIL OF THE UNIVERSITY OF TORONTO, Toronto (CA)

(72) Inventors: Patrick Thomas Gunning, Mississauga (CA); Dziyana Kraskouskaya, Misssissauga (CA); Aaron Cabral, Mississauga (CA); Bronte Murcar-Evans, Mississauga (CA); Krimo Toutah, Mississauga (CA); Elvin De Araujo, Mississauga (CA)

(73) Assignee: The Governing Council of the University of Toronto, Toronto (CA)

( * ) Notice: Subject to any disclaimer, the term of this patent is extended or adjusted under 35 U.S.C. 154(b) by 577 days.

(21) Appl. No.: 16/652,733

(22) PCT Filed: Oct. 1, 2018

(86) PCT No.: PCT/CA2018/051231
§ 371 (c)(1),
(2) Date: Apr. 1, 2020

(87) PCT Pub. No.: WO2019/068177
PCT Pub. Date: Apr. 11, 2019

(65) Prior Publication Data
US 2020/0270218 A1 Aug. 27, 2020

Related U.S. Application Data

(60) Provisional application No. 62/566,699, filed on Oct. 2, 2017.

(51) Int. Cl.
| | | |
|---|---|---|
| *C07D 417/00* | (2006.01) | |
| *C07D 257/02* | (2006.01) | |
| *C07C 233/44* | (2006.01) | |
| *C07C 309/65* | (2006.01) | |
| *C07D 213/38* | (2006.01) | |
| *G01N 21/64* | (2006.01) | |

(52) U.S. Cl.
CPC .......... *C07D 257/02* (2013.01); *C07C 233/44* (2013.01); *C07C 309/65* (2013.01); *C07D 213/38* (2013.01); *G01N 21/64* (2013.01)

(58) Field of Classification Search
CPC .................................................. C07D 417/00
See application file for complete search history.

(56) References Cited

PUBLICATIONS

Kraskouskaya, D., et al. "An Excimer-Based, Turn-On Fluorescent Sensor for the Selective Detection of Diphosphorylated Proteins in Aqueous Solution and Polyacrylamide Gels". Journal of American Chemical Society. (2014), vol. 136, pp. 1234-1237. (Year: 2014).*
Ding, Z., et al. "Nanoscale metal-organic frameworks coated with poly(vinyl alcohol) for ratiometric peroxynitrite sensing through FRET". Chem. Sci. (2017), vol. 8, pp. 5101-5106. (Year: 2017).*
G. van Meer, D. R. Voelker and G. W. Feigenson. Membrane lipids: where they are and how they behave Nat. Rev. Mol. Cell Biol., 2008, 9, 112-124.
R. A. Chaurio, C. Janko, L. E. Muñoz, B. Frey, M. Herrmann and U. S. Gaipl. Phospholipids: Key Players in Apoptosis and Immune Regulation. Molecules, 2009, 14, 4892-4914.
J. Li, X. Wang, T. Zhang, C. Wang, Z. Huang, X. Luo and Y. Deng. A review on phospholipids and their mainapplications in drug delivery systems. Asian J. Pharm. Sci., 2015, 10, 81-98.
J. N. Israelachvili, Intermolecular and surface forces, Academic Press, 2011.
P. Cullis, M. Hope and C. Tilcock. Lipid Polymorphism and the Roles of Lipids in Membranes. Chem. Phys. Lipids, 1986, 40, 127-144.
M. Bohdanowicz and S. Grinstein. Role of Phospholipids in Endocytosis,Phagocytosis, and Macropinocytosi. Physiol. Rev., 2013, 93, 69-106.
R. M. Epand and R. F. Epand. Lipid domains in bacterial membranes and the action of antimicrobial agents. Biochim. Biophys. Acta—Biomembr., 2009, 1788, 289-294.
C. Stace and N. Ktistakis. Phosphatidic acid- and phosphatidylserine-binding proteins. Biochim. Biophys. Acta—Mol. Cell Biol. Lipids, 2006, 1761, 913-926.
K. Athenstaedt and G. Daum. Phosphatidic acid, a key intermediate in lipid metabolism. Eur. J. Biochem., 1999, 266, 1-16.
V. A. Sciorra and A. J. Morris. Sequential Actions of Phospholipase D and Phosphatidic Acid Phosphohydrolase 2b Generate Diglyceride in Mammalian Cells. Mol. Biol. Cell, 1999, 10, 3863-76.
Y. Nishizuka. Protein Kinase C and Lipid Signaling for Sustained Cellular Response. FASEB J., 1995, 9, 484-96.
Andresen Bradley T, Rizzo Mark A, Shome Kuntala and Romero Guillermo(2002), The role of phosphatidic acid in the regulation of the Ras/MEK/Erk signaling cascade, FEBS Letters, 531.
Fang, U. et al. (2001). Phosphatidic acid-mediated mitogenic activation of mTOR signaling. Science, 294(5548), 1942-5.
W. Zhao, T. Róg, A. A. Gurtovenko, I. Vattulainen and M. Karttunen. Role of phosphatidylglycerols in the stability of bacterial membranes. Biochimie, 2008, 90, 930-938.
W. Dowhan. Molecular Basis for Membrane Phospholipid Diversity: Why Are There So Many Lipids? Annu. Rev. Biochem., 1997, 66, 199-232.
C. Osman, D. R. Voelker and T. Langer. Making heads or tails of phospholipids in mitochondria. J. Cell Biol., 2011, 192, 7-16.

(Continued)

*Primary Examiner* — John S Kenyon
(74) *Attorney, Agent, or Firm* — BERESKIN & PARR LLP/S.E.N.C.R.L., s.r.l.; Michael Fenwick

(57) ABSTRACT

This application relates to a method of detecting negatively charged phosphate-containing membranes and membrane components, such as in cell membranes or artificial lipid vesicles, and its use, for example, in detecting apoptosis and bacterial infection.

11 Claims, 51 Drawing Sheets

(56) References Cited

PUBLICATIONS

D. Lopez. Molecular composition of functional microdomains in bacterial membranes. Chem. Phys. Lipids, 2015, 192, 3-11.

T. Lemmin, C. Bovigny, D. Lançon and M. Dal Perar. Cardiolipin Models for Molecular Simulations of Bacterial and Mitochondrial Membranes. J. Chem. Theory Comput., 2013, 9, 670-678.

P. A. Leventis and S. Grinstein. The Distribution and Function of Phosphatidylserine in Cellular Membranes. Annu. Rev. Biophys., 2010, 39, 407-427.

B. Fadeel and D. Xue. The ins and outs of phospholipid asymmetry in the plasma membrane: roles in health and disease. Crit. Rev. Biochem. Mol. Biol., 2009, 44, 264-77.

S. Elmore. Apoptosis: A Review of Programmed Cell Death. Toxicol. Pathol., 2007, 35, 495-516.

K. Segawa, S. Kurata, Y. Yanagihashi, T. R. Brummelkamp, F. Matsuda and S. Nagata.Caspase-mediated cleavage of phospholipid flippase for apoptotic phosphatidylserine exposure. Science. 2014, 344(6188), 1164-1168.

M. Olson and L. JulianApoptotic membrane dynamics in health and disease. Cell Health Cytoskelet., 2015, vol. 7, 133.

N. Anderson and J. Borlak. Drug-induced phospholipidosis. FEBS Lett., 2006, 580, 5533-5540.

M. J. Reasor, K. L. Hastings and R. G. Ulrich. Drug-induced phospholipidosis: issues and future directions. Expert Opin. Drug Saf., 2006, 5, 567-583.

N. Liu, E. A. Tengstrand, L. Chourb and F. Y. Hsieh. Di-22:6-bis(monoacylglycerol).hosphate: A clinical biomarker of drug-induced phospholipidosis for drug development and safety assessment. Toxicol. Appl. Pharmacol., 2014, 279, 467-476.

E. Baronas, J. Lee, C. Alden and F. Hsieh. Biomarkers to monitor drug-induced phospholipidosis. Toxicol. Appl. Pharmacol., 2007, 218, 72-78.

Mills, Gordon B., and Wouter H. Moolenaar. "The emerging role of lysophosphatidic acid in cancer." Nature Reviews Cancer, vol. 3, No. 8, 2003, p. 582+.

Xu Y, Shen Z, Wiper DW, Wu M, Morton RE, Elson P, Kennedy AW, Belinson J, Markman M, Casey G. Lysophosphatidic Acid as a Potential Biomarker for Ovarian and Other Gynecologic Cancers. JAMA. 1998;280(8):719-723.

I. Vermes, C. Haanen, H. Steffens-Nakken and C. Reutelingsperger. A novel assay for apoptosis Flow cytometric detection of phosphatidylserine early apoptotic cells using fluorescein labelled expression on Annexin V. J. Immunol. Methods, 1995, 184, 39-51.

V. Gerke and S. E. Moss. Annexins: From Structure to Function. Physiol. Rev., 2002, 82, 331-371.

P. Williamson, S. van den Eijnde and R. A. Schlege. Phosphatidylserine Exposure and Phagocytosis of Apoptotic Cells 2001, Methods in Cell Biology. 66:339-364.

M. van Engeland, L. J. W. Nieland, F. C. . Ramaekers, B. Schutte and C. P. M. Reutelingsperger.Annexin V-Affinity Assay: A Review on an Apoptosis Detection System Based on Phosphatidylserine Exposure. Cytom. , 1998, 31, 1-9.

B. Pläsier, D. R. Lloyd, G. C. Paul, C. R. Thomas and M. Al-Rubeai. Automatic image analysis for quantification of apoptosis in animal cell culture by annexin-V affinity assay. J. Immunol. Methods, 1999, 229, 81-95.

J. A. Barnes and A. V Gomes. Proteolytic signals in the primary structure of annexins. Mol. Cell. Biochem., 2002, 231, 1-7.

D. Arboledas, N. Olmo, M. A. Lizarbe and J. Turnay. Role of the N-terminus in the structure and stability of chicken annexin V. FEBS Lett., 1997, 416, 217-20.

R. G. Hanshaw and B. D. Smith. New reagents for phosphatidylserine recognition and detection of apoptosis. Bioorg. Med. Chem., 2005, 13, 5035-5042.

D. Kamp, T. Sieberg and C. W. Haest. Inhibition and Stimulation of Phospholipid Scrambling Activity. Consequences for Lipid Asymmetry, Echinocytosis, and Microvesiculation of Erythrocytes. Biochemistry, 2001, 40, 9438-46.

A. Ojida, Y. Mito-oka, M. Inoue and I. Hamachi. First Artificial Receptors and Chemosensors toward Phosphorylated Peptide in Aqueous Solution. J. Am. Chem. Soc., 2002, 124, 6256-6258.

D. R. Rice, K. J. Clear, B. D. S.mith. Imaging and therapeutic applications of zinc(II)-dipicolylamine molecular probes for anionic biomembranes. Chem. Commun., 2016, 52, 8787-8801.

A. V Koulov, K. A. Stucker, C. Lakshmi, J. P. Robinson and B. D. Smith. Detection of apoptotic cells using a synthetic fluorescent sensor for membrane surfaces that contain phosphatidylserine. Cell Death Differ., 2003, 10, 1357-1359.

C. Lakshmi, R. G. Hanshaw, B. D. Smith.Fluorophore-linked zinc(II)dipicolylamine coordination complexes as sensors for phosphatidylserine-containing membranes. Tetrahedron., 2004, 60, 11307-11315.

A. V. Koulov, R. G. Hanshaw, K. A. Stucke., C. Lakshmi and B. D. Smith, Biophysical Studies of a Synthetic Mimic of the Apoptosis-Detecting Protein Annexin V. Isr. J. Chem., 2005, 45, 373-379.

W. M. Leevy, J. R. Johnson, C. Lakshmi, J. Morris, M. Marquez and B. D. Smith. Selective recognition of bacterial membranes by zinc(II)-coordination complexes. Chem. Commun., 2006, 1595.

W. M. Leevy, S. T. Gammon, H. Jiang, J. R. Johnson, D. J. Maxwell, E. N. Jackson, M. Marquez, A. David Piwnica-Worms and B. D. SmithOptical Imaging of Bacterial Infection in Living Mice Using a Fluorescent Near-Infrared Molecular Probe . . . J. Am. Chem. Soc., 2006, 128, 16476-16477.

R. G. Hanshaw, C. Lakshmi, T. N. Lambert, J. R. Johnson and B. D. Smith. Fluorescent Detection of Apoptotic Cells by Using Zinc Coordination Complexes with a Selective Affinity for Membrane Surfaces Enriched with Phosphatidylserine. ChemBioChem, 2005, 6, 2214-2220.

W. M. Leevy, S. T. Gammon, J. R. Johnson, A. J. Lampkins, H. Jiang, M. Marquez, D. Piwnica-Worms, M. A. Suckow and B. D. Smith .Noninvasive Optical Imaging of Staphylococcus aureus Bacterial Inf. ction in Living Mice Using a Bis-Dipicolylamine-Zinc(II) Affinity Group Conjugated to a Near-Infrared Fluorophore. Bioconjug. Chem., 2008, 19, 686-692.

S. Klaschik, L. E. Lehmann, A. Raadts, M. Book, A. Hoeft and F. Stuber. Real-Time PCR for Detection and Differentiation of Gram-Positive and Gram-Negative Bacteria. J. Clin. Microbiol., 2002, 40, 4304-7.

Afshari, A. et al. Bench-to-bedside review: Rapid molecular diagnostics for bloodstream infection—a new frontier? Crit. Care 16, 222 (2012).

Lee, A., Mirrett, S., Reller, L. B. & Weinstein, M. P. Detection of bloodstream infections in adults: how many blood cultures are needed? J. Clin. Microbiol. 45, 3546-8 (2007).

Kang, D.-K. et al. Rapid detection of single bacteria in unprocessed blood using Integrated Comprehensive Droplet Digital Detection. Nat. Commun. 5, 5427 (2014).

Dziyana Kraskouskaya et al. An Excimer-Based, Turn-on Fluorescent Sensor for the Selective Detection of Diphosphorylated Proteins in Aqueous Solution and Polyacrylamide Gels. J. Am. Chem. Soc. 2014, 136, 1234-1237.

Dziyana Kraskouskaya et al. Characterization and application studies of ProxyPhos, a chemosensor for the detection of proximally phosphorylated peptides and proteins in aqueous solutions/Analyst, May 25, 2017, 142, 2451-2459.

Dziyana Kraskouskaya. "Design and Development of Fluorescent Sensors for the Detection ofProximallly Phosphorylated Peptide and Protein Motifs."2015 The University of Toronto. https://tst>ace.librarv.utoronto.ca/handle/1807/80371.

PT Gunning et al. "4.05. Fluorescence-Based Chemosensors for the Detection of Biologically Relevant Phosphates in Water".in Comprehensive Supramolecular Chemistry II, vol. 4. Published Jun. 30, 2017. Elsevier Ltd.

Somkrit Marbumrung et al. "Discrimination of nucleotides by single fluorescence sensor under solvent-dependent recognition patterns." Sensors and Actuators B: Chemical 2012, 171-172, 969-975.

Florence J. Williams et al. "A Fluorescent Sensor and Gel Stain for Detection of Pyrophosphorylated Proteins."ACS Chem. Biol. 2015, 10, 1958-1963.

(56) References Cited

PUBLICATIONS

Eugenia Duodu et al. "A tool for the sequestration of ATP andPPi to aid in-solution phosphopeptide detection assays." Analyst, 2016, 141, 820-822.

Shin Mizukami et al. "A Fluorescent Anion Senor That Works in Neutral Aqueous Solution for Bioanalytical Application." J. Am. Chem. Soc. 2002, 124, 3920-3925.

\* cited by examiner

A

B

A

B

A

B

C

D

E

F

SENSORS FOR DETECTION OF NEGATIVELY CHARGED PHOSPHATE-CONTAINING MEMBRANES AND MEMBRANE COMPONENTS

CROSS-REFERENCE TO RELATED APPLICATIONS

This application is a national phase entry of PCT/CA2018/051231 filed Oct. 1, 2018, which claims the benefit of U.S. Provisional Application Ser. No. 62/566,699 filed on Oct. 2, 2017, the contents of which are hereby incorporated by reference in their entirety.

FIELD

The present application relates to chemosensors for the detection of negatively charged phosphate-containing membrane components, such as phospholipids and derivatives thereof, in, for example, biological membranes.

INTRODUCTION

Phospholipids are essential components of all living cells, where they play a structural role as a major component of cellular membranes, and are also important in metabolism, signaling pathways[1] and the immune response[2]. Phospholipids, composed of a polar phosphate head group and fatty acid tails[3], exist as free-floating monomers, but are more commonly found in aggregate forms[4], as part of a monolayer structure (e.g. micelles—spherical, single layer aggregates), or components of bi- and multi-layer systems such as intracellular liposomes/vesicles (spherical, multi-layer structures) and cell and organelle membranes[1,3]. Formation of membrane structure by phospholipids is driven by the hydrophobic effect, which packs the lipid tails together and results in the exposure of the hydrophilic phosphate head groups to the aqueous environment[3,5,6]. Glycerophospholipids, major components of mammalian and bacterial membranes[1,5,6], can be classified according to charge as either zwitterionic, of which phosphatidylcholine (PC) and phosphatidylethanolamine (PE) are most common, or negatively charged[7]. Selective detection of the negatively charged glycerophospholipids may be of particular value, as they can serve as markers for particular cell types, cellular substructures and cell signaling events. For example, negatively charged phosphatidic acid (PA) is an intermediate in lipid metabolism[8-10], is involved as a second messenger including in pathways implicated in cancer[10,11,11a,11b] and is a minor component of mammalian cellular membranes[1,8,10]. Phosphatidylglycerol (PG), on the other hand, is a major component of bacterial membranes[7,12,13], and is present primarily as a metabolite intermediate in mitochondrial membranes[1,14]. The doubly negatively charged phospholipid cardiolipin (CL) is a major component of the inner mitochondrial membrane and is a component of bacterial membranes[7,15,16]. Phosphatidylserine (PS), while only a minor component, is the most abundant negatively charged phospholipid present in mammalian cell membranes[1,17]. The distribution of PS across the membrane serves as a marker of early apoptosis[2,17-21]. Further, negatively charged phospholipids can serve as markers for disease states such as phospholipidosis, which is characterized by an excessive accumulation of negatively charged phospholipids within many tissues of the body[22,23]. Specifically, a negatively charged phospholipid derivative, di-22:6-bis(monoacylglycerol)phosphate, in serum, urine and tissues is used as a biomarker for phospholipidosis[24,25]. Lysophosphatidic acid (LPA), a pre-cursor of phosphatidic acid (PA) and other phospholipids, is primarily an extracellular signaling molecule that has recently been shown to be involved in cancer progression and metastasis, and significantly, has shown potential for use as an early diagnostic marker for certain cancers.[25a-d] Thus, an effective tool that enables robust detection of negatively charged phospholipids can be used for the detection of bacterial cells, apoptotic events, mitochondria, as well as phospholipidosis and certain cancers.

Several technologies that are based on the recognition of negatively charged membranes have found commercial application. An immunohistochemical method employing a fluorescently labeled AnnexinV protein is widely used for the early detection of apoptosis. AnnexinV exhibits strong binding to PS on the outer leaflet of mammalian cells.[26,27] In a healthy state, the negatively charged PS is maintained on the inner leaflet of mammalian membranes, but in early apoptosis, membrane asymmetry is lost, which leads to equilibration of PS levels across the membrane, resulting in its significant exposure to the outer leaflet.[2,17-21] Thus, early apoptosis can be detected by higher levels of membrane-bound AnnexinV. However, this method has significant limitations, including high $Ca^{2+}$ levels required for binding, biochemical instability and slow rate of binding.[27-32] Also problematic, is the possibility of false positives due to scramblases in the cell membrane that are activated by the high level of $Ca^{2+}$ required for AnnexinV binding.[33,34] In another example, a synthetic probe, originally reported by Hamachi et. al for the detection of phosphorylated peptides and proteins,[35] was later repurposed by the Smith group, who showed that it can be used as a turn-on chemosensor for negatively charged vesicles and a probe for apoptosis.[33,36-39] Currently marketed as PSVue™380, it operates by binding to the membrane-embedded negatively charged PS, but not the overall neutral (i.e. zwitterionic) phospholipids, and the binding event triggers an enhancement in fluorescence of its anthracene core.[39] Based on this original scaffold, a series of PSVue™ analogs, featuring different fluorophores, have been developed (Molecular Targeting Technologies Inc. Catalog).[16,33,36,37,40-42]

Based on the same principle of selective detection of negatively charged phospholipids, PSVue™380, and its infra-red emitting analogue, PSVue™794, have been further used as probes for the selective detection of bacterial cells,[36,40,41-43] whose membranes are significantly more negatively charged than the largely neutral mammalian cell membranes.[7] There is a particular need for fast, sensitive bacterial detection in clinical settings, in order to diagnose bacterial pathogens in blood or cerebrospinal fluid samples: the turnover times for the conventional methods, which include systematic culturing or qPCR, are on the scale of hours, or days, depending on the pathogen and the method.[44-47]

WO 2015/089639 describes excimer forming compounds and methods of detecting proximal phosphorylations in polypeptides.

There is a particular need for example, for fast, sensitive bacterial detection in clinical settings, in order to diagnose bacterial pathogens in blood or cerebrospinal fluid samples: the turnover times for the conventional methods, which include systematic culturing or qPCR, are on the scale of hours, or days, depending on the pathogen and the method.

SUMMARY

One object of the present application is to develop a turn-on fluorescent sensor suitable for detection of, for example, negatively charged membrane structures through selective detection of negatively charged phospholipids and derivatives thereof. A turn-on fluorescent sensor suitable for detection of negatively charged phosphate-containing compounds in membrane structures is of high value. A turn-on sensor, as compared to a probe, does not require washing of the sample to remove the unbound fluorescing probe, which enables shorter protocol times, as well as compatibility with a standard fluorometer, as compared to more laborious microscopy- and flow cytometry-based methods.

Membrane-embedded negatively charged phospholipids (MENCPs) and derivatives thereof can be used as biomarkers for a range of biological processes, including early detection of apoptosis in animal cells, drug-induced phospholipidosis, certain cancers and in selective detection of bacterial over animal cells. Currently, several technologies for the detection of apoptosis and bacterial cells are based on the recognition of MENCPs, including AnnexinV stains and PSVue™ probes. As probes, these technologies have limitations, the most significant of which, is the need for washing the unbound probe away to achieve optimal signal. In contrast, a turn-on chemosensor selective for MENCPs would address this shortcoming, and allow for a more rapid protocol for the detection of apoptosis, bacteria and for other relevant applications. As reported herein, several exemplary sensors were screened against synthetic vesicles containing biologically relevant negatively charged phospholipids including phosphatidic acid (PA), phosphatidylglycerol (PG), cardiolipin (CL) and phosphatidylserine (PS). Through these screens, sensors exhibiting high selectivity for the detection of MENCPs over zwitterionic lipids were identified. Particular selectivity was observed for PA and CL. Sensitivity of the lead sensors for MENCPs was suitable for the detection of apoptosis since vesicles containing as little as 2.5% PS were detected. In addition, sensors of the application were shown to detect both Gram-negative and Gram-positive bacteria using microscopy, fluorometry, and flow cytometry. Sensors were also shown to detect lipopolysaccharide (LPS) and lipoteichoic acid (LTA), which are major components of the Gram-negative and Gram-positive bacteria, respectively. The results suggest that these sensors can be used for the detection of MENCPs and other negatively charged species in synthetic vesicles and in biological systems.

In some embodiments, the present application includes a method of selectively detecting negatively charged phosphate-containing compounds embedded in biological membranes.

In some embodiments, the sensor comprises a turn-on dual emission fluorescent compound that is an excimer forming compound, in which the sensor is comprised of an excimer forming fluorophore. When two or more of the excimer forming fluorophores overlap or otherwise associate, a bathochromic shift in emission occurs, thereby increasing fluorescence intensity of the excimer-state fluorophore.

In some embodiments, the application includes a method of detecting negatively charged phosphate-containing membrane components comprising:
(a) combining a solution of a sample suspected of comprising negatively charged phosphate-containing membrane components with a solution comprising a compound of Formula I:

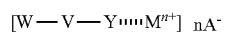

wherein,
W is a fluorophore;
V is a linker moiety;
Y is a metal ion coordinating moiety;
M is a metal cation; and
A is a weakly coordinating counter anion; and
n is 1, 2 or 3; and
(b) detecting a fluorescence signal at a wavelength specific for the fluorophore, wherein detection of the fluorescence signal in (b) indicates that the sample comprises negatively charged phosphate-containing membrane components.

In some embodiments, W is an excimer forming fluorophore. In some embodiments, W is an unsubstituted or substituted moiety shown below with any suitable point of attachment:

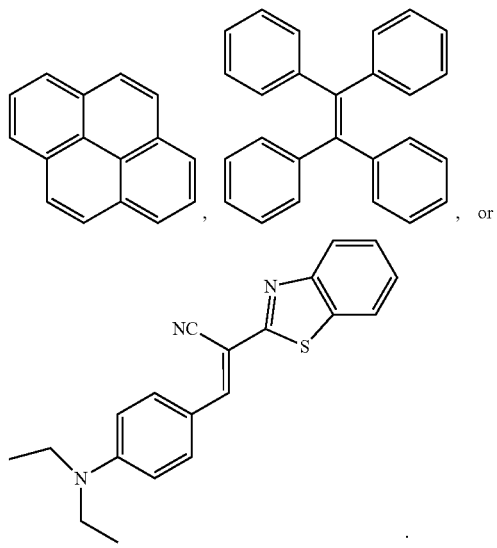

The present application also includes kits for performing the methods of the application.

The present application also includes compound of Formula IV:

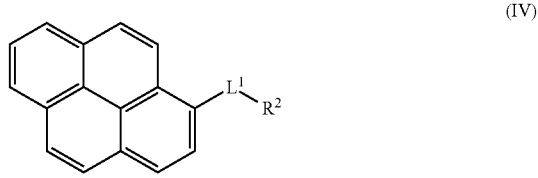

wherein:
L¹ is a linker group selected from $C_{1-20}$alkylene, $C_{2-20}$alkenylene, $C_{2-20}$alkynylene and $C_{3-10}$cycloalkylene, or a combination thereof, each of which is optionally oxo-substituted (=O) 1-3 times, and in which 1-3 carbon atoms are optionally replaced with a heteromoiety selected from NH, O, S and Si; and $R^2$ is selected from

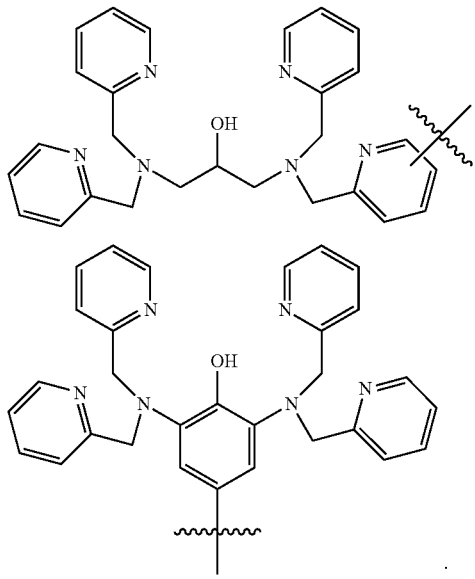

and

The present application also includes compounds of Formula V:

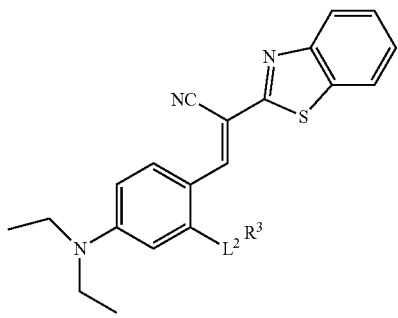

(V)

wherein

L² is a linker group selected from $C_{1-20}$alkylene, $C_{2-20}$alkenylene, $C_{2-20}$alkynylene and $C_{3-10}$cycloalkylene, or a combination thereof, each of which is optionally oxo-substituted (=O) 1-3 times, and in which 1-3 carbon atoms are optionally replaced with a heteromoiety selected from NH, O, S and Si; and R³ is selected from

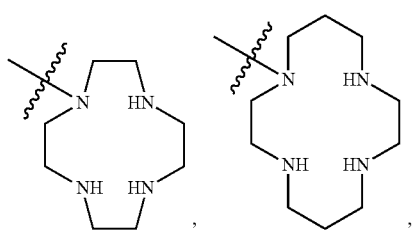

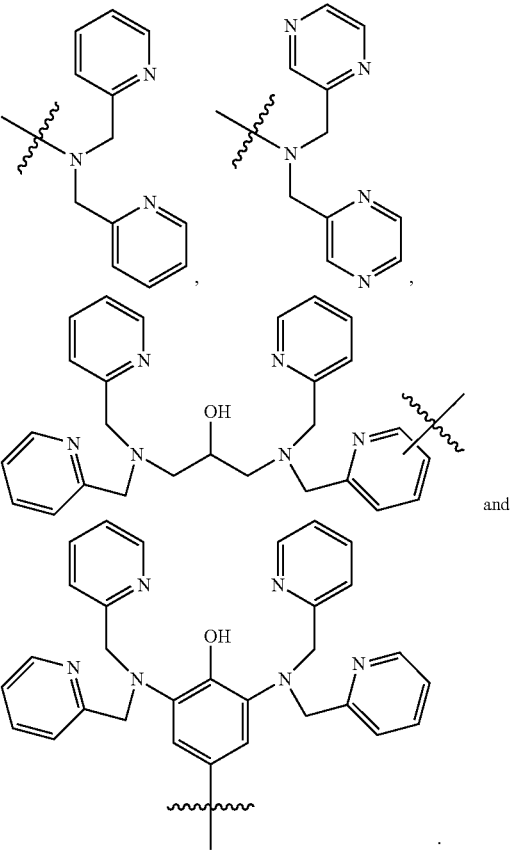

and

Other features and advantages of the present application will become apparent from the following detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

The embodiments of the application will now be described in greater detail with reference to the attached drawings in which.

DESCRIPTION OF VARIOUS EMBODIMENTS (I) Definitions

Figure 1:
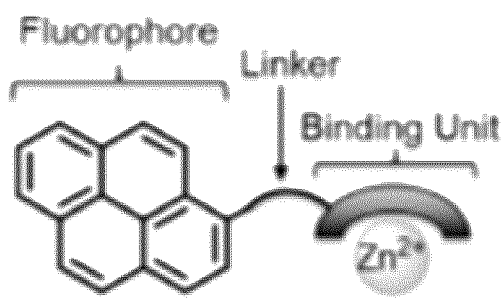
FIG. 1 shows in panel A an exemplary schematic structure of a sensor compound I, and in panel B the proposed mechanism of detection of negatively charged phospholipids.
Figure 1:
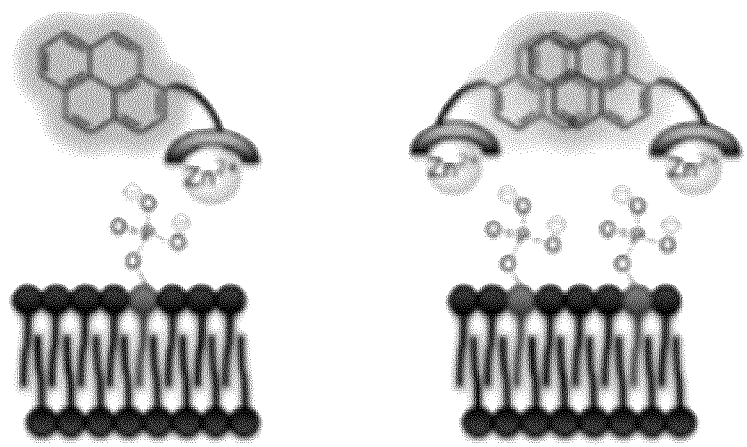

Unless otherwise indicated, the definitions and embodiments described in this and other sections are intended to be applicable to all embodiments and aspects of the present application herein described for which they are suitable as would be understood by a person skilled in the art.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a compound" should be understood to present certain aspects with one compound or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

The term "agent" as used herein indicates a compound or mixture of compounds that, when added to a composition, tend to produce a particular effect on the composition's properties.

The term "and/or" as used herein means that the listed items are present, or used, individually or in combination. In effect, this term means that "at least one of" or "one or more" of the listed items is used or present.

The term "optionally substituted" as used herein refers to no substitution on a referenced group or one or more substitutions on a referenced group where the substituent(s) are selected from halo, CN, $C_{1-6}$alkyl, $C_{2-6}$alkenyl, $C_{2-6}$alkynyl, OH, SH, $OC_{1-6}$alkyl, $SC_{1-6}$alkyl, $NH_2$, $NHC_{1-6}$alkyl, $N(C_{1-6}alkyl)(C_{1-6}alkyl)$, $C(O)C_{1-6}$alkyl, C(O)OH, C(O)

$OC_{1-6}$alkyl, $C(O)NH_2$, $C(O)NHC_{1-6}$alkyl, $C(O)N(C_{1-6}$alkyl)$(C_{1-6}$alkyl), $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneO$C_{1-6}$alkyl, $C_{1-6}$alkyleneSH, $C_{1-6}$alkyleneS$C_{1-6}$alkyl, $C_{1-6}$alkyleneNH$_2$, $C_{1-6}$alkyleneNH$C_{1-6}$alkyl and $C_{1-6}$alkyleneN($C_{1-6}$alkyl)($C_{1-6}$alkyl), wherein each alkyl, alkenyl, alkynyl, alkylene, aryl, cycloalkyl, heteroaryl and heterocycloalkyl group is optionally fluoro substituted.

The term "$C_{1-n}$alkyl" as used herein means straight or branched chain, saturated alkyl groups containing from one to n carbon atoms and includes (depending on the identity of n) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable n is an integer representing the largest number of carbon atoms in the alkyl radical.

The term "$C_{2-n}$alkenyl" as used herein means straight or branched chain, unsaturated alkyl groups containing from two to n carbon atoms and one to three double bonds, and includes (depending on the identity of n) vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like, where the variable n is an integer representing the largest number of carbon atoms in the alkenyl radical.

The term "$C_{2-n}$alkynyl" as used herein means straight or branched chain, unsaturated alkyl groups containing from two to n carbon atoms and one to three triple bonds, and includes (depending on the identity of n) ethynyl, propynyl, 2-methylprop-1-ynyl, but-1-ynyl, but-2-ynyl, but-3-ynyl, 3-methylbut-1-ynyl, 2-methylpent-1-ynyl, 4-methylpent-1-ynyl, 4-methylpent-2-ynyl, 4-methylpent-2-ynyl, penta-1,3-diynyl, hexyn-1-yl and the like, where the variable n is an integer representing the largest number of carbon atoms in the alkynyl radical.

The term "cycloalkyl" as used herein refers to a monocyclic, bicyclic or polycyclic, carbocylic ring system having 3 to "n" carbon atoms including (depending on the identity of n), but not limited to, cyclopropyl, cyclopentyl, cyclohexyl, and the like, where the variable n is an integer representing the largest number of carbon atoms in the cycloalkyl radical.

The term "$C_{6-n}$aryl" as used herein means a monocyclic, bicyclic or polycyclic, carbocyclic ring system containing from 6 to n carbon atoms and at least one aromatic ring and includes, depending on the identity of n, phenyl, naphthyl, anthracenyl, 1,2-dihydronaphthyl, 1,2,3,4-tetrahydronaphthyl, fluorenyl, indanyl, indenyl and the like, where the variable n is an integer representing the largest number of carbon atoms in the aryl radical.

The term "heteroaryl" as used herein means a monocyclic or polycyclic ring system containing from 5 to 14 atoms of which one or more, for example 1-8, suitably, 1-6, more suitably 1-5, and more suitably 1-4, of the atoms are a heteromoiety selected from O, S, NH and $NC_{1-6}$alkyl, with the remaining atoms being C or CH, said ring system containing at least one aromatic ring. Examples of heteroaryl groups, include, but are not limited to thienyl, imidazolyl, pyridyl, oxazolyl, indolyl, furanyl, benzothienyl, benzofuranyl and the like.

The term "bicyclic or polycyclic aryl moiety" as used herein refers to a bicyclic or polycyclic conjugated substituted or unsubstituted carbocyclic ring system having two or more rings including, but not limited to, naphthyl, tetrahydronaphthyl, phenanthrenyl, biphenylenyl, indanyl, indenyl, pyrenyl, peryleneyl, tetraceneyl and the like. Non-conjugated or unsaturated rings may also be bonded to or fused to the conjugated ring system.

The term "bicyclic or polycyclic heteroaryl moiety" as used herein refers to a bicyclic or polycyclic conjugated substituted or unsubstituted carbocyclic ring system having two or more rings containing, of which one or more, for example 1-8, suitably 1-6, more suitably 1-5, and more suitably 1-4, of the atoms are a heteromoiety selected from O, S, NH, $NC_{1-6}$alkyl, and C(=O), with the remaining atoms being C or CH, said ring system. Examples of heteroaryl moieties, include, but are not limited to substituted carbazoles (9-phenyl-9H-carbazole), 1H-benzo[de]isoquinoline-1,3(2H)-dione, anthra[2,1,9-def:6,5,10-d'e'f']diisoquinoline-1,3,8,10(2H,9H)-tetraone and the like. Non-conjugated or unsaturated rings may also be bonded to or fused to the conjugated ring system.

The suffix "ene" added on to any of the above groups means that the group is divalent, i.e. inserted between two other groups. When the group is a ring system, the two other groups may be located at any location on the ring system, including at adjacent and non-adjacent nodes.

The term "oxo-substituted" as used herein refers to a carbonyl group (C=O) generally replacing a $CH_2$ moiety.

The term carboxyl as used herein refers to a group of the formula COOH or $COO^-$.

The term "hydroxyl" as used herein refers to a group of the formula OH.

The term "amino" as used herein refers to an unsubstituted amino group ($NH_2$) or a primary, secondary or tertiary amino moiety substituted by alkyl or aryl groups. The term amino also includes unsaturated amino groups such as imines, or aromatic amine such as pyridine.

The term "halo" as used herein means halogen and includes chlorine, bromine, iodine and fluorine.

The term "excimer forming fluorophore" as used herein refers to a fluorophore compound that can interact with another same or different fluorophore compound to achieve excimer emission, provided that the two such fluorophores can interact together so that a complex is formed between one fluorophore in its excited state (F*) and the other fluorophore (F) in its ground state. The complex formed between F* and F, emits at a longer wavelength that the fluorophore itself.

The term "linker moiety" as used herein refers to a carbon-based moiety which connects the fluorophore with the metal ion coordinating moiety. The linker moiety may be straight-chained, branched, or cyclic, or a combination of all three, and connects one or more metal ion coordinating moieties with the fluorophore. The linker moiety optionally contains carbonyl, nitrogen and/or other heteroatom functionalities.

The term "metal ion coordinating moiety" as used herein refers to a moiety which coordinates with a metal ion, for example, a transition metal ion, a lanthanide metal ion or a post-transition metal ion and comprises one or more cyclic or acyclic organic ligands which can coordinate to a metal ion center, for example, amino, amido, carboxyl or hydroxyl groups.

The term "metal ion" as used herein refers to the positively charged forms or cations of metals.

The term "post-transition metal ion" as used herein refers to metal ions in Groups IIIB, IVB, VB, and VIB in the periodic table of the elements, and includes, but is not limited to, aluminum, gallium, germanium, indium, tin, antimony etc.

The term "lanthanide metal ion" as used herein refers to the metal ions with the atomic number from 57 to 71 in the periodic table of the elements, and includes, but is not limited to, terbium, europium, ytterbium etc.

The term "binding solution" as used herein refers to an aqueous solution containing a compound of the Formula (II) and a suitable metal ion, which optionally forms compounds of the Formula I in solution.

The term "negatively charged phosphate-containing membrane components" as used herein refers to any compound that comprises a negatively charged phosphate group, and with an overall negative charge, that is found in membrane structures.

The term "phospholipid" used herein refers to a class of lipids that are a major component of cell membranes. The structure of the phospholipid molecule generally consists of two hydrophobic fatty acid tails and a hydrophilic head comprising a phosphate group. The two components are joined together by a glycerol molecule. The phosphate group can be modified with other neutral or charged organic molecules.

The term "vesicle" or "vesicles" as used herein means a supramolecular structure comprising fluid enclosed in a lipid layer or lipid bilayer, either formed naturally in a cell such as during endocytosis or exocytosis, or formed artificially such as in the case of liposomes. A vesicle can further comprise molecules such as proteins and/or peptides.

The term "cell membrane" or "membrane" as used herein means the cell wall of a eukaryotic or a prokaryotic cell, where the cell wall comprises a lipid layer or lipid bilayer. The cell membrane or membrane can further comprise other molecules such as proteins and/or peptides.

The term "proximal" as used herein refers to the spacing between negatively charged phospholipids in, for example a membrane, such that the sites are sufficiently close to allow a bound excimer containing fluorophore compound at one site to interact, overlap or otherwise associate with a bound excimer-forming fluorophore on the other site. In some embodiments, the negatively charged phospholipids may be on two or more separate membranes, cells or vesicles, but are still close enough for interaction with an excimer containing fluorophore compound. In one embodiment, more than one negatively charged phospholipid may be present on the same membrane, cell or vesicle such as the distance between the negatively charged phospholipid sites are close enough for interaction with an excimer containing fluorophore compound. In some embodiments, the distance between negatively charged phospholipid sites may be between 2 and 100 Angstroms, optionally 3 and 50 Angstroms or suitably 5 and 30 Angstroms.

The term "subject" as used herein refers to any member of the animal kingdom. In one embodiment, the subject is a mammal, such as a human.

(II) Methods of the Application

In some embodiments, the application includes a method of detecting negatively charged phosphate-containing membrane components comprising:
(a) combining a solution of a sample suspected of comprising negatively charged phosphate-containing membrane components with a solution comprising a compound of Formula I:

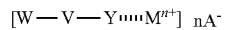

I wherein,
W is a fluorophore;
V is a linker moiety;
Y is a metal ion coordinating moiety;
M is a metal cation; and
A is a weakly coordinating counter anion; and
n is 1, 2 or 3; and
(b) detecting a fluorescence signal at a wavelength specific for the fluorophore;
wherein detection of the fluorescence signal in (b) indicates that the sample comprises negatively charged phosphate-containing membrane components.

In some embodiments, W is an excimer forming fluorophore.

In some embodiments, the fluorophore W is an optionally substituted bicyclic or polycyclic aryl or heteroaryl moiety.

In some embodiments, the fluorophore is an unsubstituted or substituted $C_{10-40}$-aryl or unsubstituted or substituted $C_{9-40}$-heteroaryl. In some embodiments, the fluorophore is unsubstituted or substituted $C_{10-20}$-aryl or unsubstituted or substituted $C_{9-20}$heteroaryl.

In some embodiments, the fluorophore is an unsubstituted or substituted moiety shown below with any suitable point of attachment to the linker moiety:

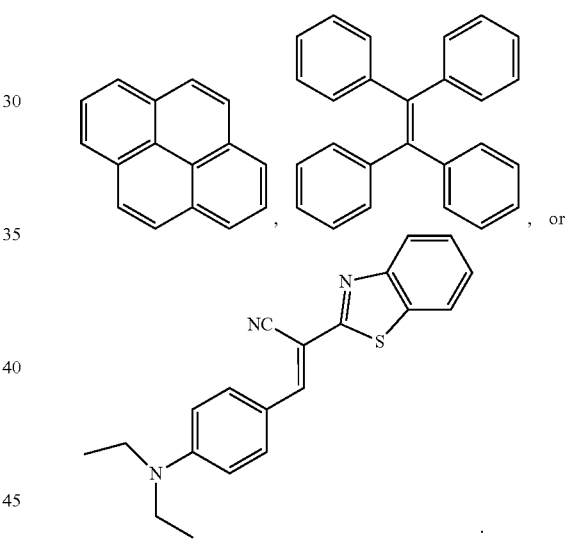

In some embodiments, the optional substituents on W are selected from halo, carboxyl, hydroxyl, $C_{1-20}$alkyl, $C_{2-20}$alkenyl, $C_{2-20}$alkynyl, $C_{3-20}$cycloalkyl, $C_{1-20}$alkoxy, —NR'R"$C_{6-14}$-aryl, and $C_{5-14}$-heteroaryl, wherein R' and R" are simultaneously or independently H or $C_{1-6}$alkyl.

In some embodiments, W is an substituted or unsubstituted

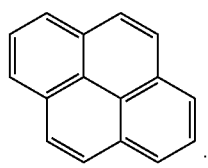 [SMILES: c1cc2ccc3cccc4ccc(c1)c2c34]

In some embodiments, W is unsubstituted.
In some embodiments, the linker moiety is $C_{1-40}$alkylene, $C_{2-40}$alkenylene, $C_{2-40}$alkynylene or $C_{3-20}$cycloalkylene, or a combination thereof, each of which is optionally oxo-substituted (=O) 1-6 times, optionally 1-3 times, and in which 1-3 carbon atoms are optionally replaced with a heteroatom/heteromoiety selected from NH, O, S and Si.

In some embodiments, the linker moiety is $C_{1-20}$alkylene, $C_{2-20}$alkenylene, $C_{2-20}$alkynylene or $C_{3-10}$cycloalkylene, or a combination thereof, each of which is optionally oxo-substituted (=O) 1-3 times, and in which 1-3 carbon atoms are optionally replaced with a heteroatom/heteromoiety selected from NH, O, S and Si.

In some embodiments, the linker moiety is selected from

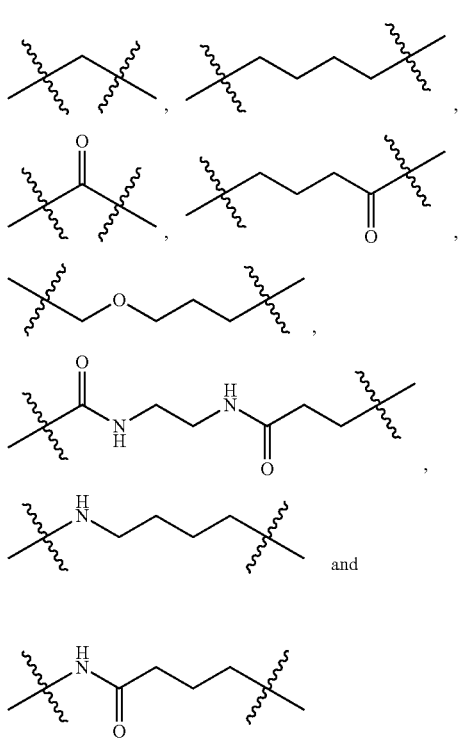

and

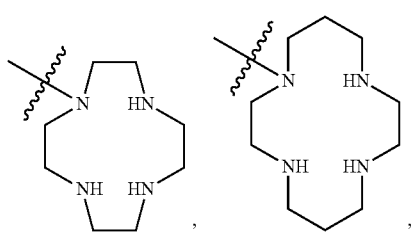

wherein ~ , represents the point of attachment to the fluorophore or the metal ion chelate moiety.

In some embodiments, the metal ion coordinating moiety is a multi-dentate moiety comprising amino, carboxyl, hydroxyl, amide, or ether groups, or other heteroatom containing moieties, wherein the heteroatom is O, S, or N.

In some embodiments, the metal ion coordinating moiety is a tri- or tetra-dentate amino group-containing moiety. In some embodiments, the tri- or tetra-dentate amino group-containing moiety is unsubstituted or substituted

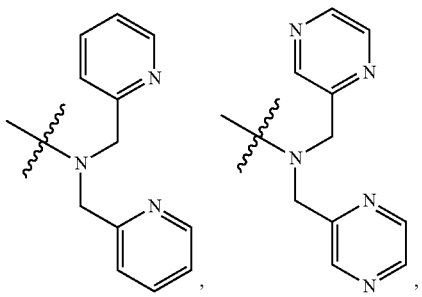

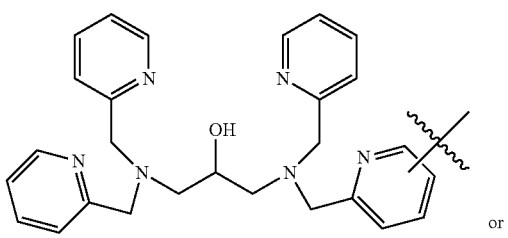

or

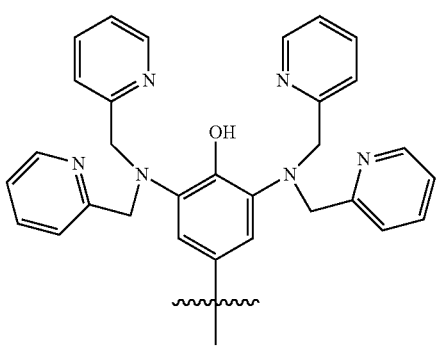

In some embodiments, the M is any suitable metal ion which coordinates, or otherwise interacts (i.e. through hydrogen bonding, ionic bonding, dipole interactions, metal-ligand interactions etc.) with the metal ion coordinating moiety, and which simultaneously binds to a negatively charged phosphate-containing membrane component (for example, in a cell membrane, a vesicle etc.). In some embodiments, M is a transition metal ion, a lanthanide metal ion or post-transition metal ion. In some embodiments, M is a divalent or trivalent metal cation. In some embodiments, M is Zn(II), Cu(II), Mn(II), Ni(II), Co(III), Fe(II), Cd(II) Al(III) or Fe(III). In some embodiments, M is Al(III) or Ga(III). In some embodiments, M is Tb(III), Eu(III), Nb(III) or Yb(III). In some embodiments, M is Zn(II).

In some embodiments, A is any suitable counter anion for a metal cation that does not prevent the metal cation from interacting with the anionic residues on the phospholipid head group. The anion may or may not dissociate from the metal cation when in aqueous solution. In some embodiments, A is selected from $CF_3SO_3^-$ (TfO$^-$), Cl$^-$, Br$^-$, I$^-$, $CH_3COO^-$, $HPO_3^-$, $HSO_4^-$, $SO_4^{2-}$ and $NO_3^-$, and the like.

In some embodiments, the compound of the Formula I is selected from:
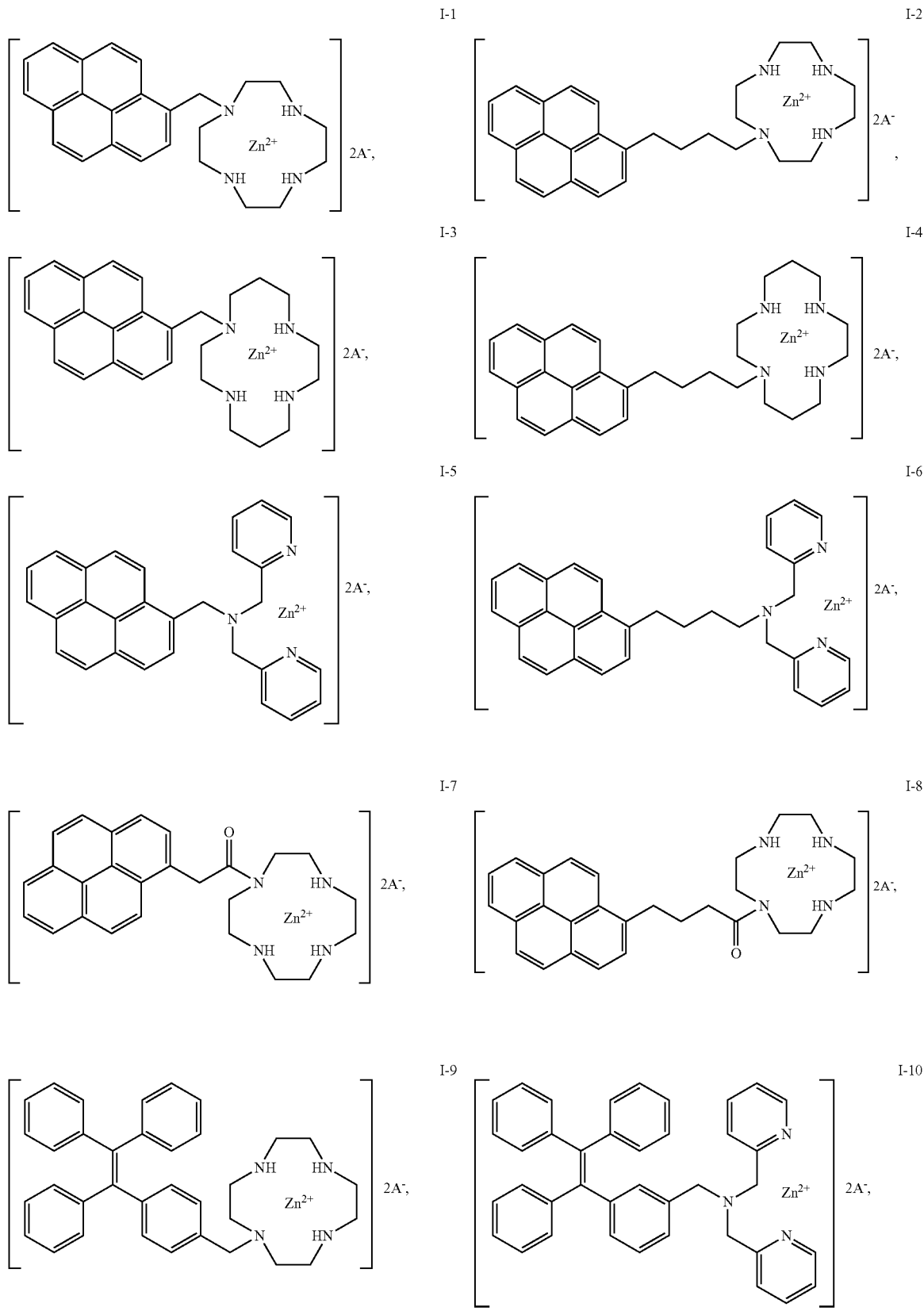

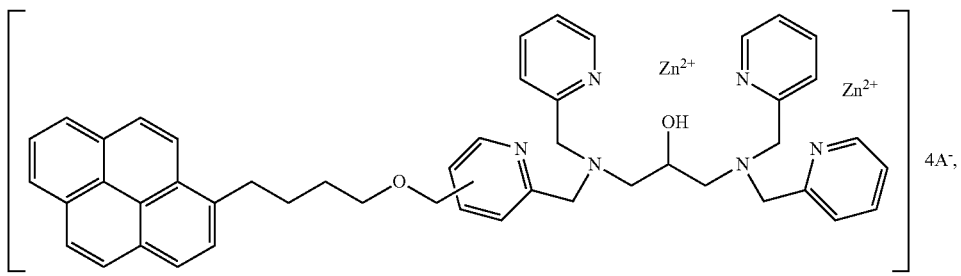
I-11
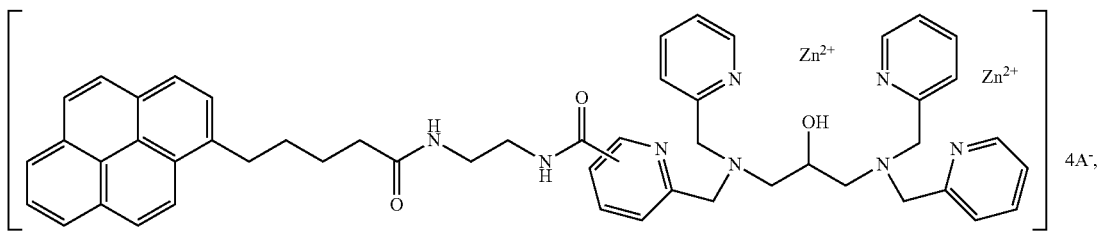
I-12
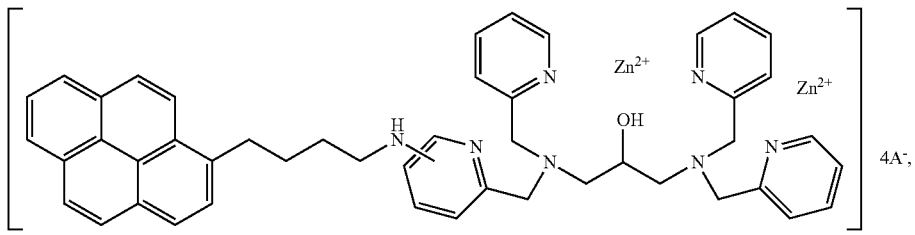
I-13
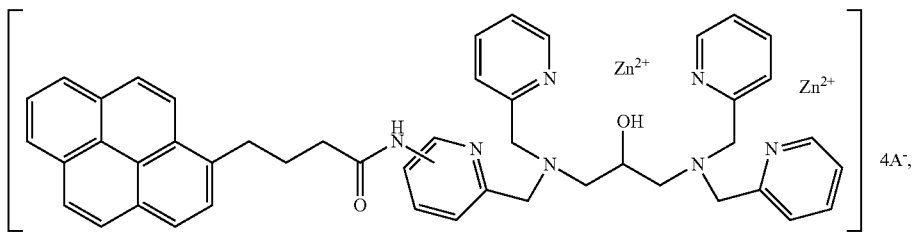
I-14
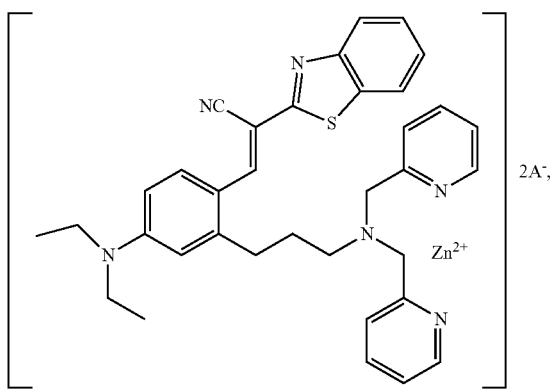
I-15
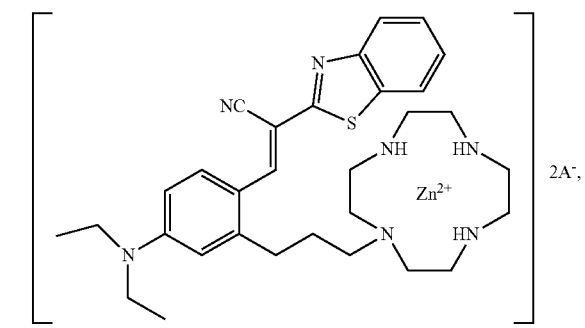
I-16

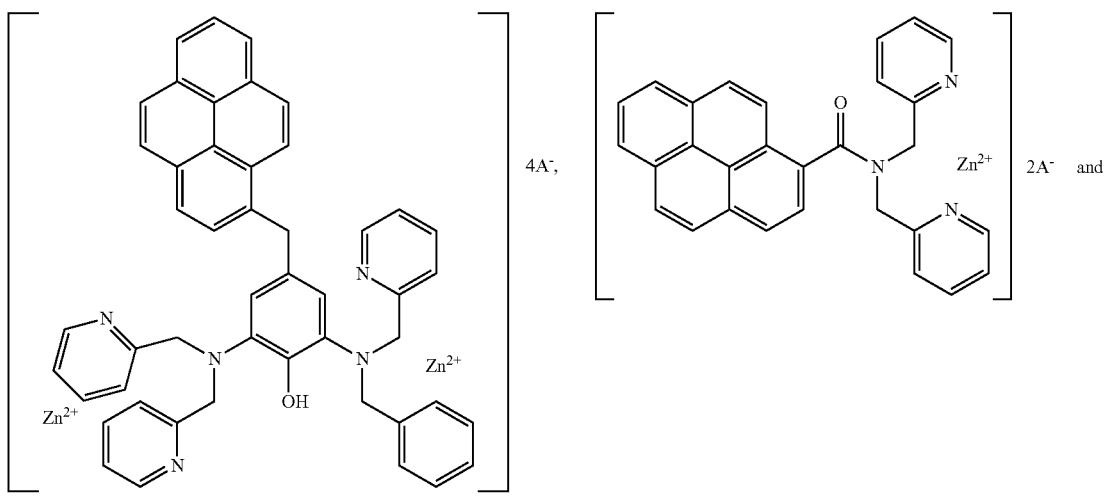
In some embodiments, the compound of Formula I-12 has the following structure:
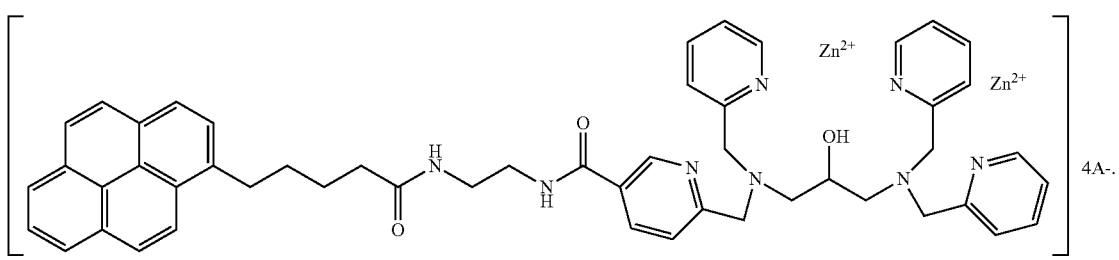

In some embodiments, the compound of Formula I-13 has the following structure:

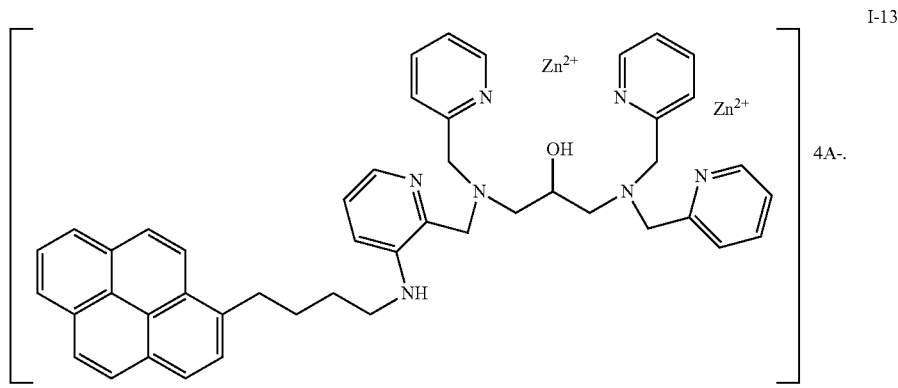

I-13

In some embodiments, the compound of Formula I-14 has the following structure:

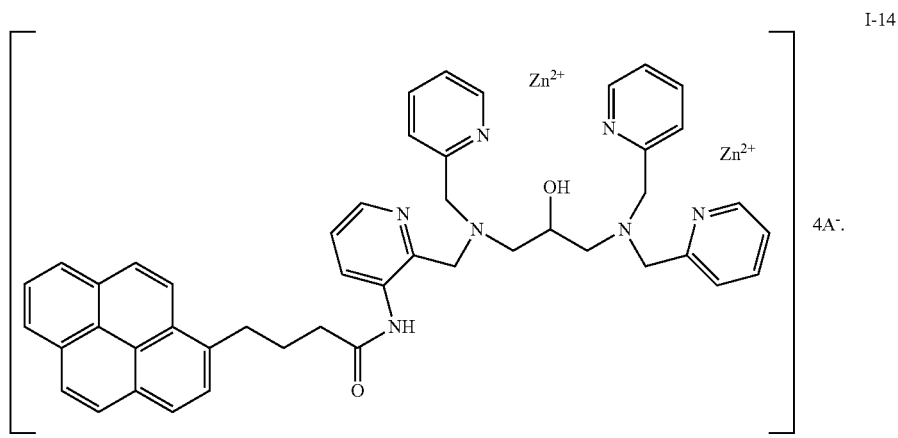

I-14

In some embodiments, it was found that, when Y is cyclen or cyclam, the method of the application does not require the presence of a metal species in the sensor compounds, Accordingly, in some embodiments, the application includes a method of detecting negatively charged phosphate-containing membrane components comprising:

(a) combining a solution of a sample suspected of comprising negatively charged phosphate-containing membrane components with a solution comprising a compound of Formula II:

W—V—Y    II wherein,
W is a fluorophore;
V is a linker moiety; and
Y is

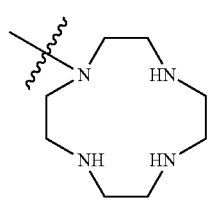

(b) detecting a fluorescence signal at a wavelength specific for the fluorophore;

wherein detection of the fluorescence signal in (b) indicates that the sample comprises negatively charged phosphate-containing membrane components.

In some embodiments, the compounds of Formula I are prepared by reacting a compound of Formula II:

W—V—Y    II, wherein W, V and Y are as defined in Formula I, with a suitable metal ion salt in an organic solvent. In some embodiments, the compounds of Formula I precipitate from the reaction solution and are isolated, for example, by filtration or any other isolation means.

In some embodiments, the compounds of the Formula I are formed in situ, for example by preparing a binding solution of a compound of Formula II and a suitable metal ion salt to form, in solution, compounds of the Formula I. In some embodiments, the binding solution comprises (i) a non-metallated compound of the Formula I; and (ii) a suitable metal ion, for example in the form of a salt. In some embodiments, the components of the binding solution are kept separate until ready for use.

In some embodiments, methods of the application comprise detecting the fluorescence signal using microscopy, flow cytometry and/or fluorometry.

In some embodiments, the fluorescence signal that is detected is at a wavelength specific for fluorescence emitted by an excimer of the fluorophore. In some embodiments the compounds of Formula I bind to negatively charged phosphate-containing membrane components that are in close proximity to each other, resulting in the formation of a $[1:1]_2$ complex of the sensor compound and leading to interaction between the fluorophores and corresponding excimer formation. In some embodiments, the fluorophore excimer formation is accompanied by a decrease in monomer-region fluorescence and the extent of excimer formation is detected and quantified by measuring the decrease in monomer fluorescence. Likewise, excimer formation is accompanied by an increase in fluorescence at the excimer-forming region of a fluorophore and the extent of excimer formation can be detected and quantified by measuring the increase in fluorescence in that region. In some embodiments, ratios of the decrease in monomer-region fluorescence and the increase in fluorescence at the excimer-forming region are calculated to detect and quantify changes at both regions.

In some embodiments, the methods of the disclosure are performed by measuring fluorescence intensity in the excimer and/or monomer regions. In some embodiments, analysis of the fluorescence is performed using fluorescence polarization, as the tertiary complex between proximal negatively charged negatively charged phosphate-containing membrane components and two excimer units limits the tumbling rate of the excimer fluorophore and increase fluorescence polarization and anisotropy values.

It will be understood that the increase in fluorescence intensity depends, for example, on the concentration of the compound of Formula I or II, and the number of negatively charged negatively charged phosphate-containing membrane components in the sample. For quantification, a calibration curve is generated based on the negatively charged phosphate-containing membrane components of known concentration which is used to compare the fluorescence signal from the sample under investigation.

In some embodiments, the relative number of negatively charged phosphate-containing membrane components can be monitored over time to determine, for example, whether this number increases or decreases over time.

In some embodiments, the fluorescence signal that is detected is compared to a control sample that does not comprise the sample and any change in fluorescence signal with the sample compared to the control indicates the presence of negatively charged phospholipids in the sample.

In some embodiments, the fluorescence signal that is detected is compared to a fluorescence signal of one or more control solutions of known quantities of negatively charged phosphate-containing membrane components and detection of a signal having a fluorescence intensity similar to the fluorescence intensity of one of the control solutions indicates that the amount of negatively charged phosphate-containing membrane components in the sample is similar to the amount of negatively charged phosphate-containing membrane components in the control solution.

The sensor compounds of the Formula I and II of the present application and binding solutions and compositions comprising these compounds are useful for detecting negatively charged phosphate-containing membrane components, such as in the form of membranes and/or vesicles. Such detection is useful for a variety of applications, including without limitation, detection of bacterial cells, apoptotic events, mitochondria, as well as phospholipidosis and certain cancers.

In some embodiments, the sample is an extract from a bacterial, yeast, insect or mammalian cell line including human cell lines.

In some embodiments, the sample is a bodily sample, such as urine, synovial fluid or blood, or any sample that contains or is suspected of containing negatively charged phospholipids.

In some embodiments, the methods disclosed herein are performed in solution, such as an aqueous buffer.

In some embodiments, sensor compounds of Formula I or II can also be used for the detection of negatively charged phosphate-containing membrane components that are attached or immobilized by any biological or synthetic means or in fixed cells or live cells.

It will be understood that the above methods can be conducted using a solution or kit, in which a compound of the Formula II and a suitable metal ion are contacted in situ to optionally form the compound of the Formula I in a binding solution. In some embodiments, the binding solution is formed before contact with the sample; for example, a binding solution comprising a compound of the Formula II and a suitable metal ion are combined in an aqueous solution to form the binding solution which is then combined with a sample to detect negatively charged phospholipids. In some embodiments, the binding solution is formed after contact with a sample; for example, an aqueous solution of a sample of a compound of the Formula II is first prepared, followed by addition of a suitable metal ion to form the binding solution. In some embodiments, the kit further comprises reagents for negative and/or positive controls.

In some embodiments, the present application describes a method for detecting negatively charged phosphate-containing membrane components in cell or vesicle membranes.

In some embodiments, the present application describes a method for detecting negatively charged phosphate-containing membrane components in bacterial membranes and/or vesicles.

In some embodiments, the present application describes a method for detecting negatively charged phosphate-containing membrane components in animal cell membranes and/or vesicles.

In some embodiments, the present application describes a method for detecting negatively charged phosphate-containing membrane components in an animal cell undergoing apoptosis.

In some embodiments, the present application describes a method for detecting bacterial infection.

In some embodiments, the negatively charged phosphate-containing membrane components being detected by methods of the present application comprise, at least one of phosphatidic acid, lysophosphatidic acid, cardiolipin, phosphatidylserine, phosphatidylglycerol, di-22:6-bis(monoacylglycerol)phosphate, lipopolysaccharide, and lipoteichoic acid. In some embodiments, the negatively charged phosphate-containing membrane components being detected are negatively charged phospholipids. In some embodiments, the negatively charged phospholipids are selected from a phosphatidylserine (PS), phosphatidic acid (PA), phosphatidylglycine and cardiolipin (CL).

(III) Compounds of the Application

The present application also includes certain novel compounds useful in the sensors of the application. Accordingly, the present application also includes compounds of Formula IV:

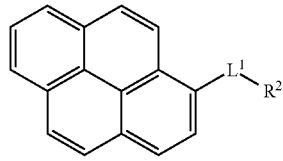

(IV)

wherein:

$L^1$ is a linker group selected from $C_{1-20}$alkylene, $C_{2-20}$alkenylene, $C_{2-20}$alkynylene and $C_{3-10}$cycloalkylene, or a combination thereof, each of which is optionally oxo-substituted (=O) 1-3 times, and in which 1-3 carbon atoms are optionally replaced with a heteromoiety selected from NH, O, S and Si; and $R^2$ is selected from

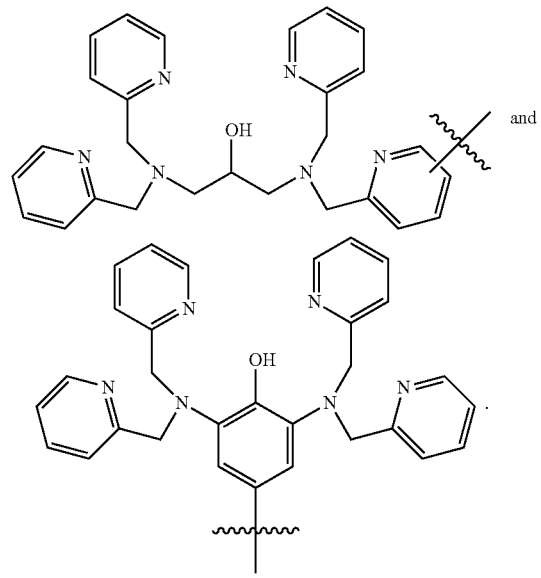

and

In some embodiments, $L^1$ is selected from:

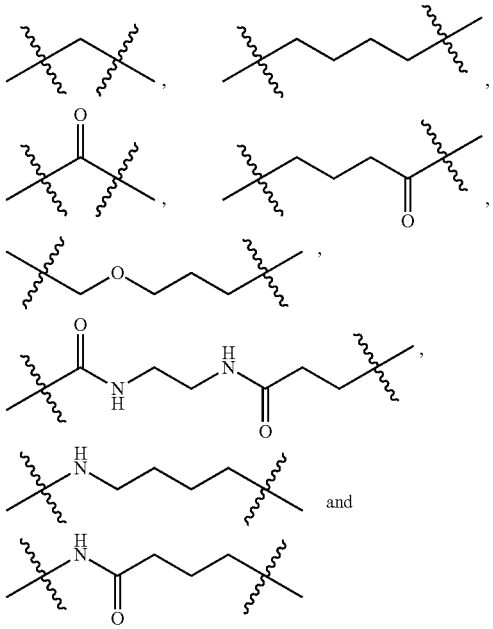

and

The present application also includes compounds of Formula V:

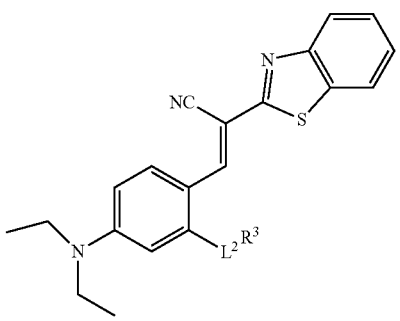

(V)

wherein $L^2$ is a linker group selected from $C_{1-20}$alkylene, $C_{2-20}$alkenylene, $C_{2-20}$alkynylene and $C_{3-10}$cycloalkylene, or a combination thereof, each of which is optionally oxo-substituted (=O) 1-3 times, and in which 1-3 carbon atoms are optionally replaced with a heteromoiety selected from NH, O, S and Si; and $R^3$ is selected from

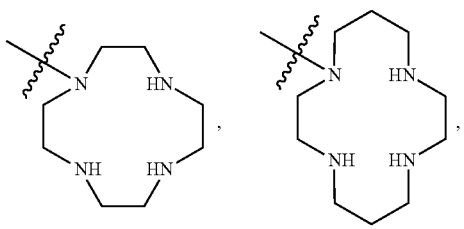

-continued

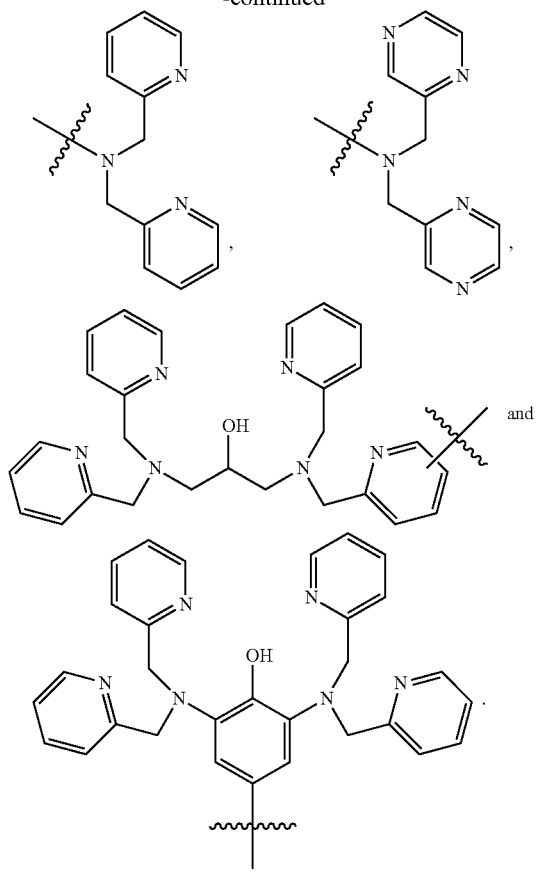

In some embodiments, $L^2$ is selected from:

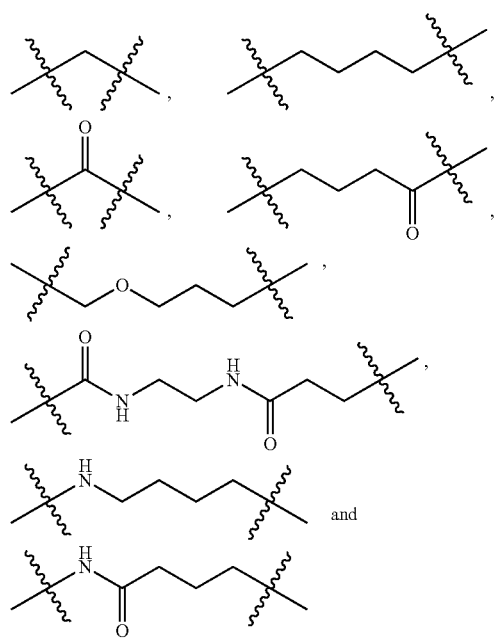

The application also includes compounds of Formula IV and V in the form of a metal chelate salt. In some embodiments, the metal is $Zn^{2+}$.

EXAMPLES

Materials and Methods:

All reagents and solvents were purchased from Sigma-Aldrich. Silica gel chromatography was performed with Silica Gel 60 (particle size 40-63 μm) obtained from EMD. Thin layer chromatography (TLC) plates were obtained from EMD. 1-palmitoyl-2-oleoyl-sn-glycero-3-phosphocholine (POPC), 1-palmitoyl-2-oleoyl-sn-glycero-3-phosphoethanolamine (POPE), 1-palmitoyl-2-oleoyl-sn-glycero-3-phospho-(1'-rac-glycerol) (sodium salt) (POPG), 1,2-dioleoyl-sn-glycero-3-phospho-L-serine (sodium salt) (DOPS), 1-palmitoyl-2-dioleoyl-sn-glycero-3-phosphate (sodium salt) (POPA), and 1,1',2,2'-tetra-(9Z-octadecenoyl) cardiolipin (sodium salt) (TOCL) were purchased from Avanti Polar Lipids (Alabaster, AL). All fluorescence experiments were performed on a Tecan Infinite M1000 using black 384-well plates (Greiner-BioOne 781076). All experiments were conducted in triplicate, in at least two independent trials.

Sensor compounds were diluted from stock solutions to a final concentration of 50 μM in 50 mM HEPES, pH 7.5, 10% DMSO, unless otherwise stated.

Care was taken to minimize exposure of compounds to light during synthesis, storage and testing. Molecular sieves were activated by heating to 125° C. under vacuum overnight. NMR spectra were recorded on a Bruker Avance III spectrometer at 23° C., operating at 400 MHz for $^1$H NMR and 100 MHz for $^{13}$C NMR spectroscopy in either $CDCl_3$ or $CD_3CN$. Chemical shifts (δ) are reported in parts per million (ppm) referenced to residual isotopic solvent. Coupling constants (J) are reported in Hertz (Hz). High Resolution Mass Spectrometry (HRMS) was performed on an AB/Sciex QStar mass spectrometer with an ESI source, MS/MS and accurate mass capabilities, associated with an Agilent 1100 capillary LC system. Low Resolution Mass Spectrometry (LRMS) was performed on a Waters Micromass ZQ model MM1. UV-vis spectra were collected using a Hewlett Packard 8452A diode array spectrophotometer with 200 μL quartz cuvettes. Purifications by prep-HPLC were performed using Atlantis Prep T3 10 μm C18 (2) 250×19 mm column run at 20 mL/min (preparative) using gradient mixtures of water with 0.1% TFA and 10:1 acetonitrile/water with 0.1% TFA. The crude mixture was injected as a solution 4:1 0.1% TFA in water/acetonitrile. Analysis by rpHPLC was performed using a Phenomex Luna 5 μm C18 (2) 150×4.60 mm column run at 1.2 mL/min (analytical) using gradient mixtures of 0.1% TFA in water and acetonitrile. Condition (A) started with 0.1% TFA water with a gradient going to 100% acetonitrile over 30 min, followed by 5 min at 100% acetonitrile. Condition (B) started with 0.1% TFA in water with a gradient going to 100% acetonitrile over 50 min, followed by 5 min at 100% acetonitrile. All final compounds were lyophilized from water/acetonitrile after purification by chromatography prior to testing. Titanic solvent was made using 92% DCM, 7% methanol and 1% ammonium hydroxide.

The sensor compounds of Formula I and Ia were prepared as previously described (WO 2015/089639).

Sensor Compound Design and Proposed Mechanism of Detection

Exemplary sensors are comprised of a $Zn^{2+}$-coordinated cyclen chelate linked to a pyrene reporter (FIG. 1A). The $Zn^{2+}$ centres are hypothesized to bind the negatively charged phospholipid residues (FIG. 1B). When negatively charged phospholipids are found in a lipid bilayer, such as a vesicle or a membrane, they may be found in close proximity, analogous to proximally phosphorylated residues on peptides and proteins. It is hypothesized that the proximity of the phospholipids could facilitate formation of a $[1:1]_2$ complex, where each of the two sensor molecules binds (via the $Zn^{2+}$ Lewis acid centre) to one of the neighbouring negatively charged phospholipid head groups, leading to interaction between the pyrene groups and the corresponding excimer formation. This is shown in FIG. 1B.

Synthesis of Sensor Compounds

Example 1: Synthesis of 1,8-bis[(2,2-dipicolylamino)methyl]anthracene (Unmetallated PSVue™380)

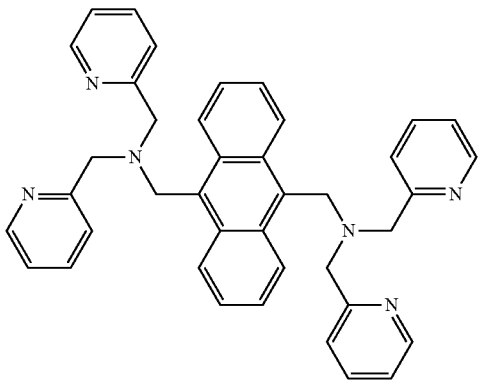 [SMILES: c1ccc(CN(Cc2ccccn2)Cc2c3ccccc3c(CN(Cc3ccccn3)Cc3ccccn3)c3ccccc23)nc1]

9,10-bis(chloromethyl)anthracene (100 mg, 0.363 mmol, 1 eq) was dissolved in THF (1 mL) and cooled to 0° C. 2,2'-dipicolylamine (0.131 ml, 0.726 mmol, 2 eq) and triethylamine (0.101 ml, 0.726 mmol, 2 eq) were dissolved in THF (1 mL) and added dropwise. The solution was stirred at room temperature for 16 h then filtered. The solvents were removed in vacuo. The residue was dissolved in DCM, washed with brine, dried over $Na_2SO_4$. After removal of the solvent in vacuo, the residue was purified by flash column chromatography (Hexanes/EtOAc) followed by recrystallization from EtOAc to give the title product (98 mg, 45%) as a pale yellow powder. $^1$H NMR (400 MHz, $CDCl_3$) δ 8.42 (d, J=5 Hz, 2H), 8.39 (dd, J=7 Hz, 4 Hz, 2H), 7.50 (td, J=8 Hz, 2 Hz, 2H), 7.42 (d, J=8 Hz, 2H), 7.28 (d, J=8 Hz, 2H), 7.02 (t, J=5 Hz, 2H), 4.63 (s, 2H), 3.86 (s, 4H). (Data in accordance with the literature: J. Am. Chem. Soc. 2002, 124, 6256-6258).

Example 2: Synthesis of PSVue™380

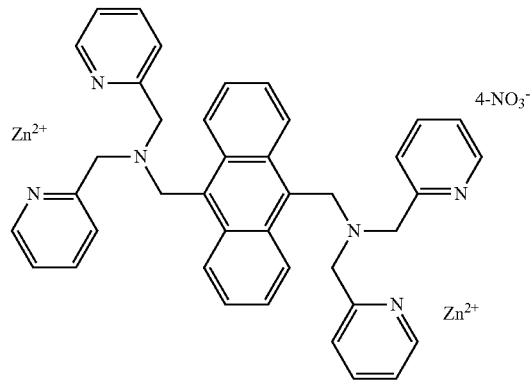 [SMILES: c1ccc(CN(Cc2ccccn2)Cc2c3ccccc3c(CN(Cc3ccccn3)Cc3ccccn3)c3ccccc23)nc1 ; [Zn+2] ; [Zn+2]]

To a solution of 1,8-bis[(2,2-dipicolylamino)methyl]anthracene (35 mg, 0.0583 mmol) in DCM (2.1 mL) was added dropwise 116 mM $Zn(NO_3)_2$ in MeOH (1 mL, 0.1166 mmol)). After stirring for 1 h at room temperature, the precipitate was filtered and washed with DCM to give PSVue™380 (42 mg, quantitative) as a pale yellow powder. $^1$H NMR (400 MHz, DMSO-$d_6$+$D_2O$) δ 8.66 (bs, 2H), 8.09 (bs, 2H), 8.00 (bs, 2H), 7.68 (bs, 2H), 7.57 (bs, 2H), 7.28 (bs, 2H), 4.94 (s, 4H), 4.10 (d, 8 Hz, 4H), 3.67 (d, 8 Hz, 4H). $^{13}$C NMR (125 MHz, DMSO-$d_6$+$D_2O$) δ 154.7, 148.7, 147.3, 141.8, 140.5, 131.9, 127.5, 126.9, 126.2, 125.9, 124.6, 58.0, 56.9, 55.8.

Example 3: 1-(pyren-1-ylmethyl)-1,4,7,10-tetraazacyclododecane (Non-Metallated II-1)

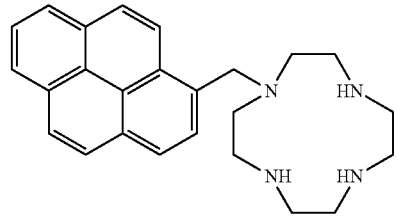 [SMILES: c1cc2ccc3ccc(CN4CCNCCNCCNCC4)c4ccc(c1)c2c34]

Compound II-1 was prepared in accordance to the following source: Gunning, P. T., Kraskouskaya, D., 2016. Excimer forming compounds. US20160304473 A1.

Example 4: 1-(4-(pyren-1-yl)butyl)-1,4,7,10-tetraazacyclododecane (II-2)

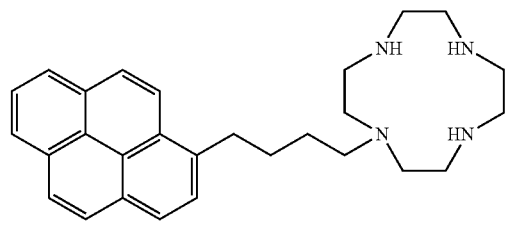 [SMILES: c1cc2ccc3ccc(CCCCN4CCNCCNCCNCC4)c4ccc(c1)c2c34]

Compound II-2 was prepared in accordance to the following source: Gunning, P. T., Kraskouskaya, D., 2016. Excimer forming compounds. US20160304473 A1.

Example 5: tri-tert-butyl 11-(pyren-1-ylmethyl)-1,4, 8,11-tetraazacyclotetradecane-1,4,8-tricarboxylate (II-3A)

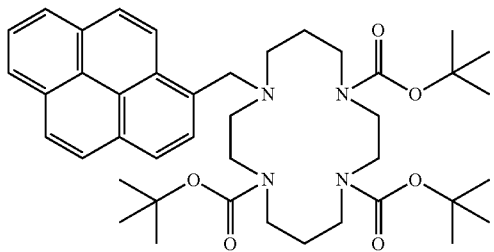 [SMILES: CC(C)(C)OC(=O)N1CCCN(C(=O)OC(C)(C)C)CCN(C(=O)OC(C)(C)C)CCCN(Cc2ccc3ccc4cccc5ccc2c3c45)CC1]

To a solution of 1-pyrenecarboxaldehyde (35 mg, 0.15 mmol) in 1 mL DCE, Boc$_3$Cyclam (50 mg, 0.10 mmol) was added and stirred together with 4 Å molecular sieves for 2 h under nitrogen atmosphere. To this solution sodium triacetoxyborohydride (42 mg, 0.2 mmol) was added and the reaction mixture was allowed to stir at ambient temperature over 24 h under nitrogen atmosphere. Subsequently, the reaction mixture was diluted with sodium bicarbonate and extracted with DCM. The extract was purified by flash chromatography with 30% ethyl acetate/hexanes to give the product (63 mg, 88%); 1H NMR (400 MHz, CDCl$_3$) δ 8.47 (d, J=9.3 Hz, 1H), 8.21-7.93 (m, 8H), 4.22 (s, 2H), 3.34 (s, 10H), 3.13 (s, 2H), 2.78 (s, 2H), 2.50 (s, 2H), 1.88 (s, 2H), 1.76-1.66 (m, 2H), 1.51-1.17 (m, 27H); $^{13}$C NMR (100 MHz, CDCl$_3$) δ 155.55, 132.64, 131.33, 130.87, 130.77, 129.71, 128.41, 127.47, 127.10, 125.83, 125.00, 124.83, 124.50, 124.06, 79.67, 79.44, 58.59, 54.24, 53.43, 47.81, 47.07, 29.72, 28.50, 28.46, 28.31; LRMS (ESI+) m/z calc'd for C$_{42}$H$_{58}$N$_4$O$_6$Na [M+Na]$^+$ 737.42, found 737.65.

Example 6: 1-(pyren-1-ylmethyl)-1,4,8,11-tetraazacyclotetradecane (II-3)

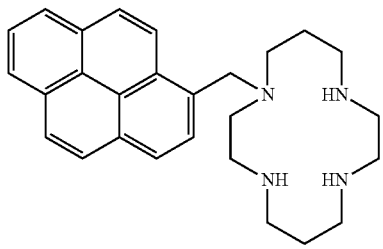 [SMILES: c1cc2ccc3ccc(CN4CCCNCCNCCCNCC4)c4ccc(c1)c2c34]

To a solution of compound II-3A (108 mg, 0.15 mmol) in 10 mL DCM, 5 mL TFA was added. The reaction mixture was stirred at rt. The progress of the reaction was monitored using MS. The reaction mixture was concentrated down in vacuo and the TFA was azeotroped off in vacuo with MeOH. The crude product was taken up in MeOH and passed through a column packed with Amberlite IRN-78. The solvent was evaporated in vacuo. The mixture was then purified by preparative HPLC. The product was again passed through a column packed with Amberlite IRN-78 to give the product (45 mg, 72%); mp 101-104° C.; $^1$H NMR (400 MHz, CDCl$_3$) δ 8.47 (d, J=9.3 Hz, 1H), 8.18-8.05 (m, 5H), 8.02 (s, 2H), 7.97 (t, J=7.6 Hz, 1H), 4.19 (s, 2H), 2.90-2.79 (m, 6H), 2.78-2.74 (m, 2H), 2.70-2.64 (m, 6H), 2.62-2.57 (m, 2H), 2.56-2.48 (m, 4H), 1.87 (quint, J=5.3 Hz, 2H), 1.60 (quint, J=5.3 Hz, 2H); $^{13}$C NMR (100 MHz, CDCl$_3$) δ 132.8, 131.2, 130.6, 130.4, 129.5, 128.0, 127.3, 127.0, 126.9, 125.7, 124.9, 124.8, 124.74, 124.72, 124.4, 123.5, 56.8, 54.8, 54.1, 50.3, 48.9, 48.6, 48.3, 47.5, 47.4, 27.9, 26.4; LRMS (ESI+) m/z calc'd for C$_{27}$H$_{35}$N$_4$ [M+H]$^+$ 415.29, found 415.20; HRMS (ESI+) m/z calc'd for C$_{27}$H$_{35}$N$_4$ [M+H]$^+$ 415.2862, found 415.2854; rpHPLC t$_R$: condition (A) 12.499 min., condition (B) 19.601 min., purity 99.8% and 96.1% respectively.

Example 7: tri-tert-butyl 11-(4-(pyren-1-yl)butyl)-1, 4,8,11-tetraazacyclotetradecane-1,4,8-tricarboxylate (II-4A)

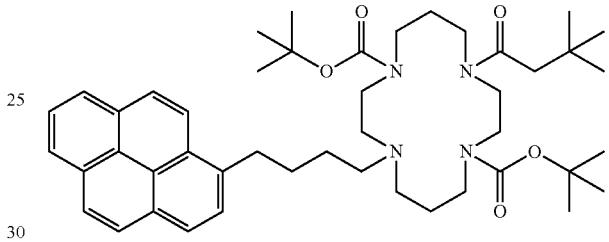

To a solution of 4-(pyren-1-yl)butanal (37 mg, 0.14 mmol) in 0.9 mL DCE, Boc$_3$Cyclam (45 mg, 0.09 mmol) was added and stirred together with 4 Å molecular sieves for 2 h under nitrogen atmosphere. To this solution sodium triacetoxyborohydride (38 mg, 0.18 mmol) was added and the reaction mixture was allowed to stir at ambient temperature over 24 h under nitrogen atmosphere. Subsequently, the reaction mixture was diluted with sodium bicarbonate and extracted with DCM. The extract was purified by flash chromatography with 35% ethyl acetate/hexanes to give the product (43 mg, 63%); $^1$H NMR (400 MHz, CDCl$_3$) δ 8.29 (d, J=9.3 Hz, 1H), 8.21-7.98 (m, 7H), 7.88 (d, J=7.8 Hz, 1H), 3.46-3.09 (m, 14H), 2.59 (s, 2H), 2.50-2.33 (m, 4H), 1.93-1.74 (m, 4H), 1.73-1.58 (m, 4H), 1.53-1.41 (m, 27H); $^{13}$C NMR (100 MHz, CDCl$_3$) δ 155.69, 136.80, 131.44, 130.91, 129.80, 128.58, 127.52, 127.24, 127.20, 126.57, 125.81, 125.11, 125.05, 124.86, 124.81, 124.67, 123.40, 79.55, 79.36, 55.42, 48.69, 48.55, 47.30, 46.90, 46.62, 45.69, 33.54, 29.85, 29.72, 28.56, 28.50, 26.79; LRMS (ESI+) m/z calc'd for C$_{45}$H$_{65}$N$_4$O$_6$ [M+H]$^+$ 757.49, found 757.69.

Example 8: Compound II-4

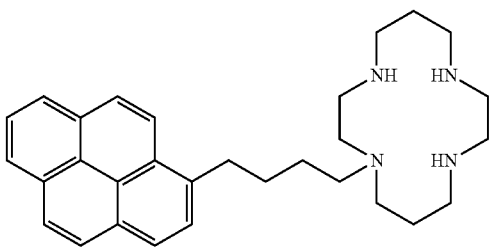 [SMILES: c1cc2ccc3ccc(CCCCN4CCCNCCNCCCNCC4)c4ccc(c1)c2c34]

To a solution compound II-4A (79 mg, 0.1 mmol) in 15 mL DCM, 1 mL TFA was added. The reaction mixture was stirred at rt. The progress of the reaction was monitored using MS. The reaction mixture was concentrated down in vacuo and the TFA was azeotroped off in vacuo with MeOH. The crude product was taken up in MeOH and passed through a column packed with Amberlite IRN-78. The solvent was evaporated in vacuo. The mixture was then purified by preparative HPLC. The product was again passed through a column packed with Amberlite IRN-78 to give the product (38 mg, 80%); $^1$H NMR (400 MHz, CDCl$_3$) δ 8.30 (d, J=9.3 Hz, 1H), 8.17-8.08 (m, 4H), 8.04-7.95 (m, 3H), 7.88 (d, J=7.8 Hz, 1H), 3.35 (t, J=7.5 Hz, 2H), 2.62 (t, J=5.3 Hz, 2H), 2.59-2.54 (m, 4H), 2.51-2.47 (m, 2H), 2.46-2.41 (m, 4H), 2.40-2.33 (m, 4H), 2.24-2.20 (m, 2H), 1.85 (quint, J=8.1 Hz, 2H), 1.73-1.66 (m, 2H), 1.65-1.59 (m, 2H), 1.59-1.51 (m, 2H); $^{13}$C NMR (100 MHz, CDCl$_3$) δ 137.1, 131.3, 130.8, 129.6, 128.4, 127.3, 127.2, 127.1, 126.4, 125.6, 124.9, 124.67, 124.65, 124.5, 123.4, 54.6, 54.2, 52.6, 51.2, 49.8, 49.3, 48.5, 47.7, 47.6, 33.4, 30.0, 28.6, 26.4, 26.1; LRMS (ESI+) m/z calc'd for C$_{30}$H$_{40}$N$_4$ [M+H]$^+$ 456.33, found 457.32. rpHPLC t$_R$: condition (A) 13.550 min., condition (B) 21.547 min., purity 99.0% and 98.9% respectively.

Example 9: 1-(pyren-1-yl)-N, N-bis(pyridin-2-ylmethyl)methanamine (II-5)

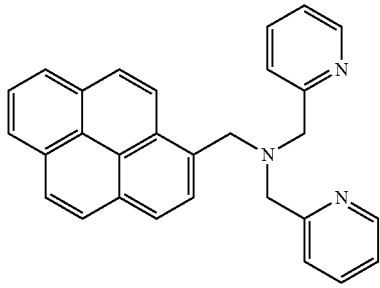 [SMILES: c1ccc(CN(Cc2ccccn2)Cc2ccc3ccc4cccc5ccc2c3c45)nc1]

Compound II-5 was prepared in accordance to the following source: Gunning, P. T., Kraskouskaya, D., 2016. Excimer forming compounds. US20160304473 A1.

Example 10: 4-(pyren-1-yl)-N,N-bis(pyridin-2-ylmethyl)butan-1-amine (II-6)

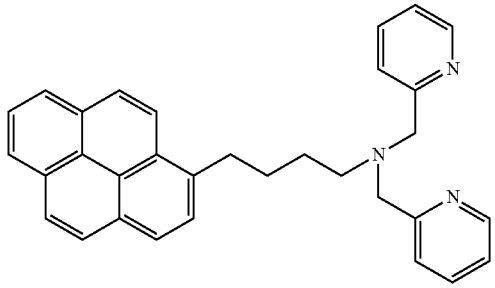 [SMILES: c1ccc(CN(CCCCc2ccc3ccc4cccc5ccc2c3c45)Cc2ccccn2)nc1]

Compound II-6 was prepared in accordance to the following source: Gunning, P. T., Kraskouskaya, D., 2016. Excimer forming compounds. US20160304473 A1.

Example 11: 2-(pyren-1-yl)-1-(1,4,7,10-tetraazacyclododecan-1-yl)ethanone (II-7)

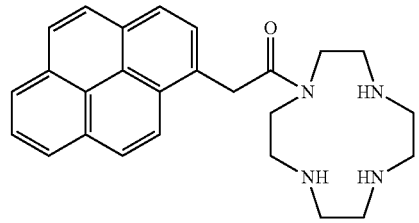 [SMILES: O=C(Cc1ccc2ccc3cccc4ccc1c2c34)N1CCNCCNCCNCC1]

Compound II-7 was prepared in accordance to the following source: Gunning, P. T., Kraskouskaya, D., 2016. Excimer forming compounds. US20160304473 A1.

Example 12: tri-tert-butyl 10-(4-(pyren-1-yl)butanoyl)-1,4,7,10-tetraazacyclododecane-1,4,7-tricarboxylate (II-8A)

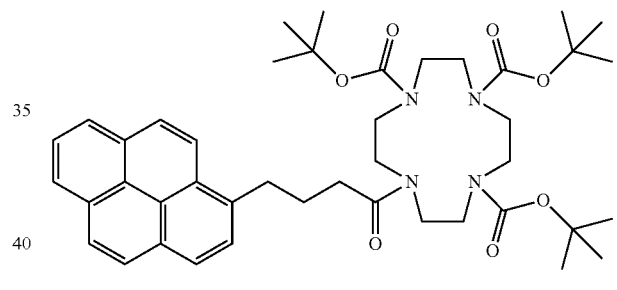

To a solution of 1-pyrenebutyric acid (48.8 mg, 0.169 mmol) in 1 mL DMF was added Boc$_3$Cyclen (80 mg, 0.169 mmol) and TBTU (87 mg, 0.271 mmol) and the reaction mixture was stirred for 30 min at rt. DIPEA (103 μL, 0.592 mmol) was then added to this reaction mixture and stirred at rt for 16 h. Subsequently, the mixture was diluted with water and extracted with dichloromethane. The combined organic phases were dried over sodium sulfate and concentrated. The crude product was purified by flash chromatography with 30% ethyl acetate/hexanes to give the product (93 mg, 74%); $^1$H NMR (400 MHz, CDCl$_3$) δ 8.35 (d, J=9.2 Hz, 1H), 8.19-8.09 (m, 4H), 8.01 (s, 2H), 7.98 (t, J=7.6 Hz, 1H), 7.88 (d, J=7.8 Hz, 1H), 3.80-3.19 (m, 16H), 2.50 (bs, 2H), 2.24 (p, J=7.0 Hz, 2H), 2.05 (s, 2H), 1.48 (s, 9H), 1.42 (s, 18H); $^{13}$C NMR (100 MHz, CDCl$_3$) δ 171.1, 155.4, 136.1, 131.4, 130.9, 129.9, 128.8, 127.5, 127.3, 127.2, 126.6, 125.8, 125.1, 125.0, 124.8, 124.8, 124.7, 123.5, 80.3, 80.3, 80.1, 60.4, 51.4, 49.7, 33.1, 28.5, 28.4, 27.1, 21.0, 14.2; LRMS (ESI+) m/z calc'd for C$_{43}$H$_{58}$N$_4$O$_7$Na [M+Na]$^+$ 751.42, found 751.42.

Example 13: 4-(pyren-1-yl)-1-(1,4,7,10-tetraazacyclododecan-1-yl)butan-1-one (II-8)

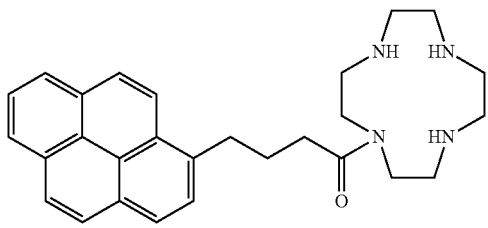 [SMILES: O=C(CCCc1ccc2ccc3cccc4ccc1c2c34)N1CCNCCNCCNCC1]

To a solution of compound II-8A (102 mg, 0.14 mmol) in 10 mL DCM, 5 mL TFA was added. The reaction mixture was stirred at rt. The progress of the reaction was monitored using MS. The reaction mixture was concentrated down in vacuo and the TFA was azeotroped off in vacuo with MeOH. The crude product was taken up in MeOH and passed through a column packed with Amberlite IRN-78. The solvent was evaporated in vacuo. The mixture was then purified by preparative HPLC. The product was again passed through a column packed with Amberlite IRN-78 to give the product (49 mg, 79%); mp 83-86° C.; $^1$H NMR (400 MHz, CD$_3$OD) δ 8.31 (d, J=9.3 Hz, 1H), 8.15-8.10 (m, 2H), 8.09-8.04 (m, 2H), 8.01-7.91 (m, 3H), 7.84 (d, J=7.8 Hz, 1H), 3.60-3.53 (m, 4H), 3.36-3.29 (m, 2H), 3.10 (br, 10H), 3.00 (br, 2H), 2.53 (t, J=7.3 Hz, 2H), 2.08 (quint, J=7.7 Hz, 2H); $^{13}$C NMR (100 MHz, CD$_3$OD) δ 175.3, 136.1, 131.4, 130.9, 129.9, 128.6, 127.2, 127.1, 127.0, 126.3, 125.7, 124.8, 124.7, 124.6, 124.6, 124.5, 123.2, 48.3, 47.3, 46.7, 44.8, 43.9, 32.3, 32.0, 26.8; LRMS (ESI+) m/z calc'd for C$_{28}$H$_{35}$N$_4$O [M+H]$^+$ 443.28, found 444.22; HRMS (ESI+) m/z calc'd for C$_{28}$H$_{35}$N$_4$O [M+H]$^+$ 443.2811, found 443.2815; rpHPLC t$_R$: condition (A) 13.382 min., condition (B) 19.843 min., purity 100.0% and 99.8% respectively.

Example 14: 2-(p-tolyl)ethene-1,1,2-triyl)tribenzene (II-9A)

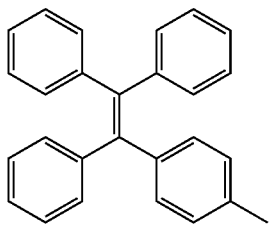 [SMILES: Cc1ccc(C(=C(c2ccccc2)c2ccccc2)c2ccccc2)cc1]

2-Bromo-1,1,2-triphenylethylene (300 mg, 0.895 mmol) 4-methylphenylboronic acid (146 mg, 1.07 mmol), tetrabutylammonium bromide (14.4 mg, 0.0447 mmol), and tetrakis(triphenylphosphine)palladium(0) (103 mg, 0.0895 mmol) were transferred into a rbf under argon. The reagents were dissolved in 9 mL of THF, and then 0.2 mL of 2 M potassium carbonate (2 mmol) was injected into the rbf. The solution was stirred in an oil bath at 100° C. for 16 h. The solvent was evaporated and the residue was extracted with chloroform and brine. The organic layers were combined and dried with anhydrous magnesium sulfate. The crude product was purified by column chromotography using 4:1 DCM/Hexanes as eluent (267 mg, 86%). $^1$H NMR (400 MHz, CDCl$_3$) δ 7.21-7.03 (m, 15H), 6.96 (s, 4H), 2.31 (s, 3H).

Example 15: (2-(4-(bromomethyl)phenyl)ethene-1,1,2-triyl)tribenzene (II-9B)

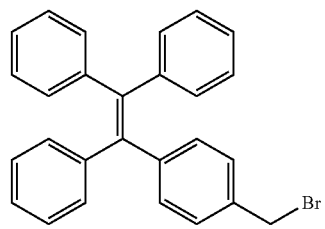 [SMILES: BrCc1ccc(C(=C(c2ccccc2)c2ccccc2)c2ccccc2)cc1]

A solution of II-9A (160 mg, 0.462 mmol), N-bromosuccinimide (90.4 mg, 0.508 mmol) and benzoyl peroxide (11.2 mg, 0.0462 mmol) were dissolved in 2.5 mL of chloroform. The solution was refluxed for 14 h. The mixture was extracted with dichloromethane and water. The organic layers were combined, dried with magnesium sulfate and concentrated down in vacuo. The crude product was purified by column chromotography using 5% ethyl acetate in hexanes as eluent to give the product as a white solid (145 mg, 74%). $^1$H NMR (400 MHz, CDCl$_3$) δ 7.23-7.06 (m, 19H), 4.46 (s, 2H).

Example 16: tri-tert-butyl 10-(4-(1,2,2-triphenylvinyl)benzyl)-1,4,7,10-tetraazacyclododecane-1,4,7-tricarboxylate (II-9C)

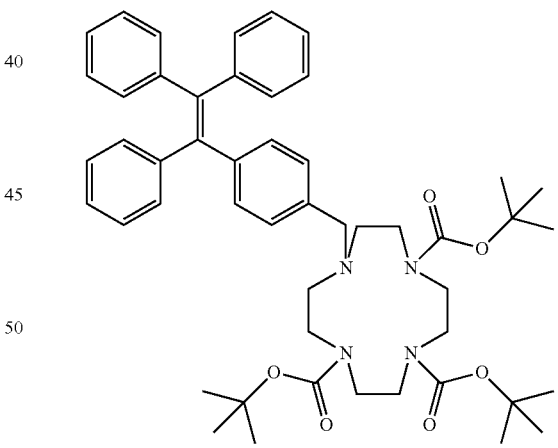

A solution of II-9B (145 mg, 0.341 mmol), Boc$_3$Cyclen (201 mg, 0.426 mmol) and potassium carbonate (236 mg, 1.7 mmol) was dissolved in 3.5 mL acetonitrile and refluxed overnight. The solution was concentrated down in vacuo and the residue was extracted with dichloromethane and water. The organic layer was washed with brine and dried with magnesium sulfate. The solvent was concentrated down in vacuo and purified by flash chromatography using ethyl acetate/hexanes (2:1) as eluent to give the product (176 mg, 87%). $^1$H NMR (400 MHz, CDCl$_3$) δ 7.16-6.96 (m, 19H), 3.65 (s, 2H), 3.61-3.52 (m, 4H), 3.44-3.03 (m, 8H), 1.51-

1.45 (br, 28H). LRMS (ESI+) m/z calc'd for $C_{50}H_{65}N_4O_6$ [M+H]$^+$ 818.09, found 817.86.

Example 17: 1-(4-(1,2,2-triphenylvinyl)benzyl)-1,4,7,10-tetraazacyclododecane (II-9)

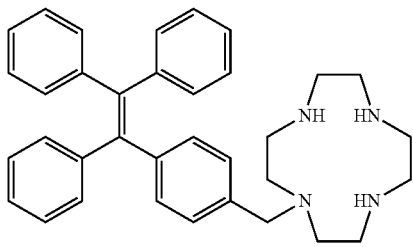 [SMILES: c1ccc(C(=C(c2ccccc2)c2ccc(CN3CCNCCNCCNCC3)cc2)c2ccccc2)cc1]

To a solution of II-9C (176 mg, 0.215 mmol) in 2 mL DCM, 0.72 mL TFA was added. The reaction mixture was stirred at rt overnight. The progress of the reaction was monitored using MS. The reaction mixture was concentrated down in vacuo and the TFA was azeotroped off in vacuo with MeOH. The crude product was taken up in MeOH and passed through a column packed with Amberlite IRN-78. The solvent was evaporated in vacuo. The mixture was then purified by preparative HPLC. The product was again passed through a column packed with Amberlite IRN-78 to give the product (82 mg, 86%); $^1$H NMR (400 MHz, CDCl$_3$) δ 7.14-7.07 (m, 9H), 7.07-7.00 (m, 8H), 7.00-6.95 (m, 2H), 3.57 (s, 2H), 2.80 (t, J=6.6, 3.7 Hz, 4H), 2.67 (t, J=5.0 Hz, 4H), 2.57 (t, J=7.1, 4.4, 3.6 Hz, 8H). LRMS (ESI+) m/z calc'd for $C_{35}H_{41}N_4$ [M+H]$^+$ 517.74, found 517.50; rpHPLC $t_R$: condition (A) 16.241 min., condition (B) 26.261 min., purity 98.6% and 97.5% respectively.

Example 18: 1-(pyridin-2-yl)-N-(pyridin-2-ylmethyl)-N-(3-(1,2,2-triphenylvinyl)benzyl)methanamine (II-10)

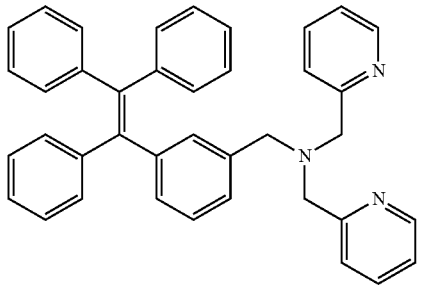 [SMILES: c1ccc(C(=C(c2ccccc2)c2cccc(CN(Cc3ccccn3)Cc3ccccn3)c2)c2ccccc2)cc1]

A mixture of II-9B (151 mg, 0.356 mmol), bis(2-pyridylmethyl)amine (106 mg, 0.534 mmol) and K$_2$CO$_3$ (246 mg, 178 mmol) in acetonitrile (3.6 mL) was added together under Nitrogen atmosphere, and refluxed overnight. After, the solution was concentrated down in vacuo, followed by dissolving the residue in DCM and extracted with water and brine. The combined organic layers were dried with magnesium sulfate and concentrated in vacuo. The mixture was then purified by preparative HPLC. The product was passed through a column packed with Amberlite IRN-78 to give the product (79 mg, 41%). $^1$H NMR (400 MHz, CD$_3$CN-d3) δ 8.49 (dt, J=4.9, 1.2 Hz, 2H), 7.70 (td, J=7.7, 1.8 Hz, 2H), 7.51 (d, J=7.8 Hz, 2H), 7.23-7.09 (m, 10H), 7.07-6.97 (m, 11H), 3.71 (s, 4H), 3.57 (s, 2H); $^{13}$C NMR (101 MHz, CD$_3$CN-d3) δ 148.82, 136.34, 130.89, 130.87, 130.75, 128.31, 127.71, 127.70, 127.64, 126.46, 122.77, 121.98, 117.30, 59.52. HRMS (ESI+) m/z calc'd for $C_{39}H_{34}N_3$ [M+H]$^+$ 544.2747, found 544.2752.

Example 19: 2-(bromomethyl)-6-((4-(pyren-1-yl)butoxy)methyl)pyridine (II-11A)

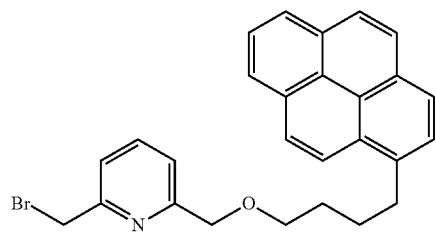 [SMILES: BrCc1cccc(COCCCCc2ccc3ccc4cccc5ccc2c3c45)n1]

To a stirred solution of 1-pyrenebutanol (442 mg, 1.61 mmol) in 16.1 mL dry THF (0.1 M) in an ice bath was added 95% NaH (407 mg, 16.1 mmol) under an Nitrogen atmosphere. The reaction flask was removed from the ice bath after 30 min and allowed to return to room temperature. After, 2,6-bis(bromomethyl)pyridine (1.07 g, 4.07 mmol) was added and the flask was stirred at ambient temperature for 4 h under an Nitrogen atmosphere. Subsequently, the reaction mixture was quenched with methanol and concentrated by evaporation. The organic layer was extracted in DCM and NaHCO$_{3(aq)}$ and dried with excess sodium sulfate. The extract was filtered and concentrated by evaporation. The crude material was purified by flash chromatography was performed (20% ethyl acetate in hexanes) to afford the product as a white powder (502 mg, 68%). $^1$H NMR (400 MHz, CH$_2$Cl$_2$-d$_2$) δ 8.32 (d, J=9.0 Hz, 1H), 8.23-7.95 (m, 7H), 7.92 (d, J=8.0 Hz, 1H), 7.66 (t, J=8.0 Hz, 1H), 7.38-7.27 (m, 2H), 4.59 (s, 2H), 4.51 (s, 2H), 3.65 (t, J=6.0 Hz, 2H), 3.45-3.36 (m, 2H), 2.05-1.93 (m, 2H), 1.90-1.78 (m, 2H); LRMS (ESI+) m/z calc'd for $C_{27}H_{25}BrNO$ [M+H]$^+$ 459.41, found 460.38.

Example 20: 1-amino-3-(((6-((4-(pyren-1-yl)butoxy)methyl)pyridin-2-yl)methyl)amino)propan-2-ol (II-11B)

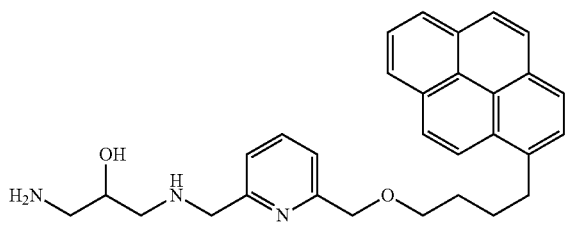 [SMILES: NCC(O)CNCc1cccc(COCCCCc2ccc3ccc4cccc5ccc2c3c45)n1]

To a stirred solution of II-11A (270 mg, 0.589 mmol) in 2.4 mL DMF was added 1,3-diamino-2-propanol (531 mg, 5.89 mmol) and potassium carbonate (244 mg, 1.77 mmol). The reaction was stirred at ambient temperature for 1 hr under an Nitrogen atmosphere. The reaction mixture was filtered and concentrated by evaporation. The crude material was purified by flash chromatography (14% MeOH, 85%

DCM, 1% NH₄OH) to afford compound II-11B as a brown oil (202 mg, 73%). ¹H NMR (400 MHz, CH₂Cl₂-d₂) δ 8.28 (d, J=9.0 Hz, 1H), 8.15 (d, J=8.0 Hz, 2H), 8.14-7.91 (m, 5H), 7.86 (d, J=8.0 Hz, 1H), 7.55 (t, J=8.0 Hz, 1H), 7.22 (d, J=8.0 Hz, 1H), 7.10 (d, J=8.0 Hz, 1H), 4.54 (s, 2H), 3.82 (d, J=3.0 Hz, 2H), 3.71 (s, 2H), 3.58 (s, 1H), 3.42-3.30 (m, 2H), 2.83 (dd, J=12.0, 3.0 Hz, 1H), 2.73-2.61 (m, 2H), 2.55 (dd, J=12.0, 8.0 Hz, 1H), 1.98-1.89 (m, 1H), 1.87-1.73 (m, 2H), 1.30 (d, J=12.0 Hz, 1H), 0.95-0.83 (m, 1H); LRMS (ESI+) m/z calc'd for C₃₀H₃₄N₃O₂ [M+H]⁺ 468.26, found 468.36.

Example 21: 1-(bis(pyridin-2-ylmethyl)amino)-3-(((6-((4-(pyren-1-yl)butoxy)methyl)pyridin-2-yl)methyl)(pyridin-2-ylmethyl)amino)propan-2-ol (II-11)

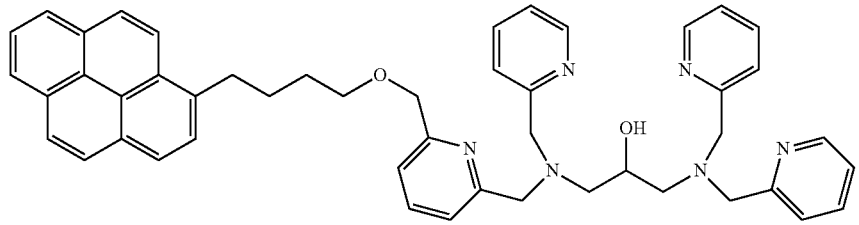 [SMILES: OC(CN(Cc1ccccn1)Cc1ccccn1)CN(Cc1ccccn1)Cc1cccc(COCCCCc2ccc3ccc4cccc5ccc2c3c45)n1]

To a stirred solution of compound II-11B (200 mg, 0.428 mmol, 1 equiv.) in 10 mL 1,2-dichloroethane (DCE, 0.04 M) was added 2-pyridinecarboxaldehyde (0.407 mL, 4.28 mmol, 10 equiv.) and 20-30 Å molecular sieves under an Nitrogen atmosphere. After, Na(OAc)₃BH (952 mg, 4.49 mmol, 10.5 equiv.) was added and the reaction was left stirring overnight at ambient temperature. The reaction mixture was quenched using saturated sodium bicarbonate, extracted in DCM and NaHCO₃₍aq₎, and dried with excess magnesium sulfate. The extract was filtered and concentrated by evaporation. The crude material was purified by flash chromatography (93% DCM, 6% MeOH, 1% NH₄OH) to afford the compound as a brown oil (125 mg, 40%). ¹H NMR (400 MHz, CD₃CN) δ 8.44-8.36 (m, 3H), 8.31 (d, J=9.5 Hz, 1H), 8.19 (dd, J=7.5, 1.5 Hz, 2H), 8.13 (d, J=8.0 Hz, 1H), 8.09 (d, J=9.5 Hz, 1H), 8.05 (d, J=1.0 Hz, 2H), 8.01 (t, J=7.5 Hz, 1H), 7.89 (d, J=8.0 Hz, 1H), 7.63-7.53 (m, 4H), 7.31 (t, J=8.0 Hz, 3H), 7.20 (dd, J=7.5, 3.0 Hz, 2H), 7.10 (dd, J=6.5, 5.0 Hz, 3H), 4.64 (s, 1H), 4.47 (s, 2H), 3.86-3.65 (m, 9H), 3.57 (t, J=6.5 Hz, 2H), 3.34 (t, J=8.0 Hz, 2H), 2.53 (dd, J=13.0, 3.0 Hz, 2H), 2.39 (ddd, J=13.0 7.5, 3.0 Hz, 2H), 1.92-1.83 (m, 2H), 1.80-1.70 (m, 2H). ¹³C NMR (101 MHz, CD₂Cl₂) δ 159.57, 158.82, 158.13, 148.73, 148.33, 136.96, 136.65, 136.35, 136.04, 131.29, 130.79, 129.59, 128.47, 127.35, 127.18, 126.93, 126.32, 125.68, 124.84, 124.80, 124.66, 124.64, 124.50, 123.38, 122.82, 121.92, 121.69, 121.25, 120.22, 119.13, 73.64, 70.67, 67.08, 64.08, 60.62, 60.53, 58.90, 33.07, 29.68, 28.36. HRMS (ESI+): m/z: calc'd for C₄₈H₄₉N₆O₂: 741.3917; found: 741.3916.

Example 22: Compound II-12A

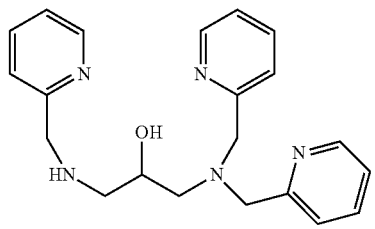 [SMILES: OC(CNCc1ccccn1)CN(Cc1ccccn1)Cc1ccccn1]

This compound was prepared according to the following source: Kawasaki, A., Kobashi, T., Koike, T., Takahagi, M., 2004. Method for labelling phosphorylated peptides, complex compounds used in the methods, process for producing the same, and their intermediates. EP1455189 A1.

Example 23: Compound II-12B

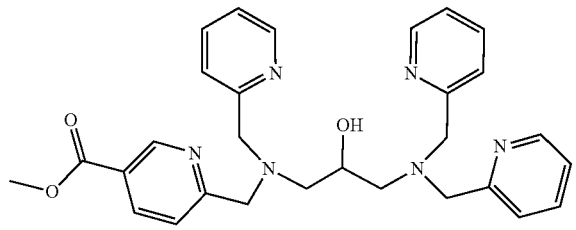 [SMILES: COC(=O)c1ccc(CN(Cc2ccccn2)CC(O)CN(Cc2ccccn2)Cc2ccccn2)nc1]

This compound was prepared according to the following source: Kawasaki, A., Kobashi, T., Koike, T., Takahagi, M., 2004. Method for labelling phosphorylated peptides, complex compounds used in the methods, process for producing the same, and their intermediates. EP1455189 A1.

Example 24: Compound II-12C

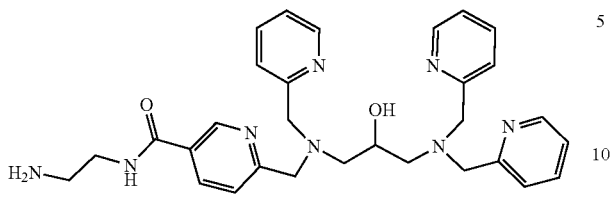

This compound was prepared according to the following source: Kawasaki, A., Kobashi, T., Koike, T., Takahagi, M., 2004. Method for labelling phosphorylated peptides, complex compounds used in the methods, process for producing the same, and their intermediates. EP1455189 A1.

Example 25: 2-(((3-(bis(pyridin-2-ylmethyl)amino)-2-hydroxypropyl)(pyridin-2-ylmethyl)amino)methyl)-N-(2-(3-(pyren-1-yl)propanamido)ethyl) isonicotinamide (II-12)

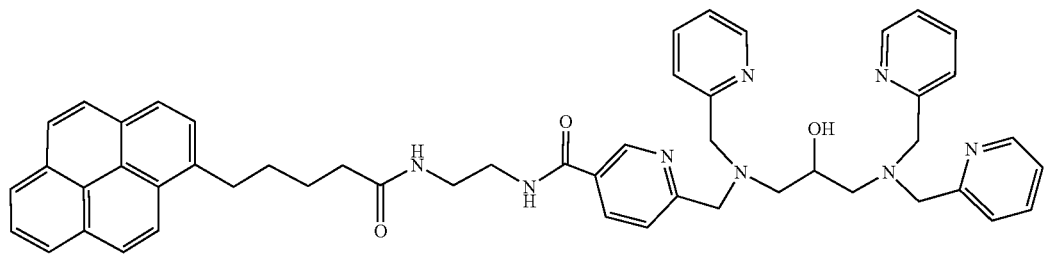 [SMILES: O=C(CCCCc1ccc2ccc3cccc4ccc1c2c34)NCCNC(=O)c1ccc(CN(Cc2ccccn2)CC(O)CN(Cc2ccccn2)Cc2ccccn2)nc1]

A solution of 1-pyrenebutyric acid (55.5 g, 0.192 mmol), I-12C (104 mg, 0.192 mmol) and DMAP (47 mg, 0.385 mmol) in DCM (11 mL) was stirred under an argon atmosphere. EDC (73.7 mg, 0.385 mmol) was separately dissolved in DCM (1.5 mL) and added. The solution was stirred at ambient temperature overnight. The solution was extracted with water and dried with anhydrous Magnesium sulfate. The product was concentrated down in vacuo and the crude product purified by preparative TLC using DCM/MeOH/NH$_4$OH 91:8:1 as the eluent to yield the product as a yellow oil. $^1$H NMR (400 MHz, CDCl$_3$) δ 8.84 (s, 1H), 8.35 (t, J=5.0 Hz, 2H), 8.12 (d, J=10.5 Hz, 1H), 8.02 (dd, J=16.0, 8.0 Hz, 2H), 7.93 (d, J=8.5 Hz, 2H), 7.91-7.80 (m, 4H), 7.68 (d, J=8.0 Hz, 1H), 7.53-7.36 (m, 3H), 7.29-7.11 (m, 4H), 7.05-6.93 (m, 3H), 6.88 (t, 5.0 Hz, 1H), 3.88-3.59 (m, 9H), 3.48-3.41 (m, 2H), 3.41-3.33 (m, 2H), 3.20 (t, J=7.5 Hz, 2H), 2.50 (dd, J=13.0, 3.5 Hz, 2H), 2.41 (dd, J=13.0, 8.0 Hz, 2H), 2.22 (t, J=7.0 Hz, 2H), 2.13-1.97 (m, 2H). LRMS (ESI+) m/z calc'd for C$_{50}$H$_{50}$N$_8$O$_3$Na [M+Na]$^+$ 833.99, found 833.86.

Example 26: Compound II-13A

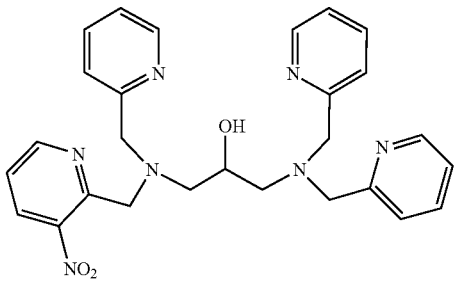 [SMILES: O=[N+]([O-])c1cccnc1CN(Cc1ccccn1)CC(O)CN(Cc1ccccn1)Cc1ccccn1]

This compound was prepared according to the following source: Kawasaki, A., Kobashi, T., Koike, T., Takahagi, M., 2004. Method for labelling phosphorylated peptides, complex compounds used in the methods, process for producing the same, and their intermediates. EP1455189 A1.

Example 27: Compound II-13B

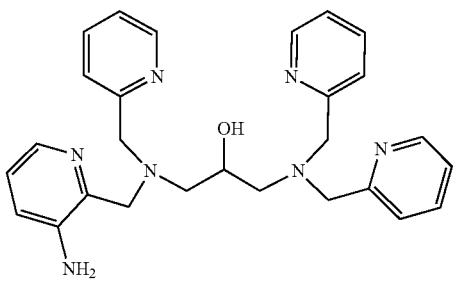 [SMILES: Nc1cccnc1CN(Cc1ccccn1)CC(O)CN(Cc1ccccn1)Cc1ccccn1]

This compound was prepared according to the following source: Kawasaki, A., Kobashi, T., Koike, T., Takahagi, M., 2004. Method for labelling phosphorylated peptides, complex compounds used in the methods, process for producing the same, and their intermediates. EP1455189 A1.

Example 28: 1-(bis(pyridin-2-ylmethyl)amino)-3-(((6-((4-(pyren-1-yl)butyl)amino)pyridin-2-yl)methyl)(pyridin-2-ylmethyl)amino)propan-2-ol (II-13)

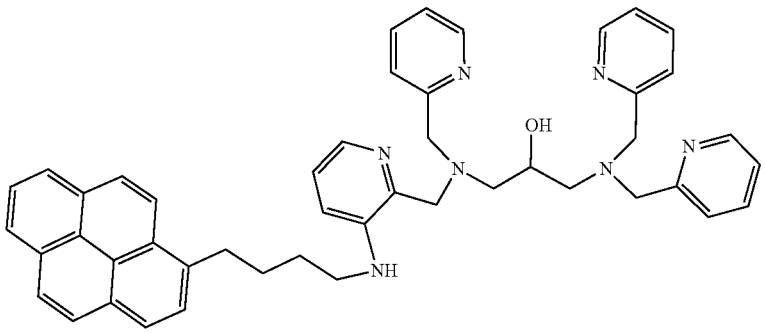 [SMILES: OC(CN(Cc1ccccn1)Cc1ccccn1)CN(Cc1ccccn1)Cc1ncccc1NCCCCc1ccc2ccc3cccc4ccc1c2c34]

A solution of precursor II-13B (181 mg, 0.385 mmol) dissolved in DCE (2 mL) was transferred into a solution of 4-(pyren-1-yl)butanal (157 mg, 0.578 mmol) in DCE (2 mL). To this solution was added acetic acid (66.2 μL, 1.16 mmol), followed by addition of powdered NaBH(OAc)$_3$ (245 mg, 1.16 mmol) in one portion under nitrogen at ambient temperature, and stirred overnight. The mixture was diluted with DCM and quenched with concentrated NH$_4$OH in water. The two layers were separated, and the aqueous layer was extracted with DCM (10 mL×2). The combined organic layers were washed 3 times with water and brine and dried using magnesium sulfate. The crude was purified with the use of preparative HPLC (0.1% TFA in 100% water to 100% ACN gradient). The collected fractions were lyophilized from ACN/Water to give the product (16 mg, 6%). $^1$H NMR (400 MHz, CDCl$_3$) δ 8.71 (d, J=5.5 Hz, 2H), 8.66 (d, J=5.5 Hz, 1H), 8.21 (d, J=9.0 Hz, 1H), 8.19-8.13 (m, 2H), 8.11 (d, J=7.5 Hz, 1H), 8.09-8.04 (m, 2H), 8.04-7.94 (m, 4H), 7.89-7.79 (m, 2H), 7.75 (d, J=8.0 Hz, 2H), 7.68 (d, J=5.5 Hz, 2H), 7.46 (t, J=6.0 Hz, 2H), 7.33-7.22 (m, 1H), 7.16 (dd, J=8.5, 5.5 Hz, 1H), 6.89 (d, J=8.5 Hz, 1H), 4.33-4.11 (m, 8H), 4.07 (d, J=15.0 Hz, 2H), 3.35 (dd, J=9.0, 6.0 Hz, 3H), 3.17-3.07 (m, 2H), 2.74-2.50 (m, 2H), 2.03-1.89 (m, 2H), 1.85-1.72 (m, 2H). $^{13}$C NMR (101 MHz, CDCl$_3$) δ 153.32, 153.22, 145.52, 143.83, 143.55, 143.15, 142.71, 136.39, 135.80, 131.31, 130.74, 129.73, 128.47, 127.48, 127.27, 127.00, 126.71, 126.42, 126.04, 125.97, 125.79, 125.04, 124.86, 124.81, 124.67, 123.26, 121.36, 64.67, 59.54, 58.40, 56.65, 54.14, 42.84, 32.89, 28.84, 27.81. LRMS (ESI+) m/z calc'd for C$_{47}$H$_{47}$N$_7$ONa [M+Na]$^+$ 748.93, found 748.70. HRMS (ESI+): m/z: calc'd for C$_{47}$H$_{48}$N$_7$O [M+H]+: 726.3915, found: 726.3906.

Example 29: N-(6-(((3-(bis(pyridin-2-ylmethyl)amino)-2-hydroxypropyl)(pyridin-2-ylmethyl)amino)methyl)pyridin-2-yl)-4-(pyren-1-yl)butanamide (II-14)

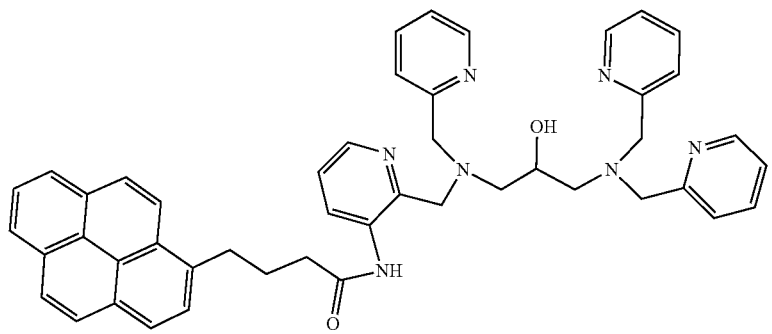 [SMILES: O=C(CCCc1ccc2ccc3cccc4ccc1c2c34)Nc1cccnc1CN(Cc1ccccn1)CC(O)CN(Cc1ccccn1)Cc1ccccn1]

To a solution of 1-pyrenebutyric acid (73 mg, 0.253 mmol) in DCM (2.5 mL), DMAP (4.94 mg, 0.0404 mmol) and triethylamine (35.2 µL, 0.253 mmol) were added at ambient temperature. A solution of II-13B (95 mg, 0.202 mmol) in DCM (2.5 mL) was added dropwise at ambient temperature. EDC (48 mg, 0.253 mmol) was then added and the reaction was refluxed overnight. Afterwards, the reaction was allowed to stir for another 24 h at ambient temperature. The obtained reaction mixture extracted with DCM and water. The combined organic layers were washed 3 times with water and brine and dried using magnesium sulfate. The crude product was purified by column chromatography (DCM:MeOH:NH$_4$OH 93:6:1) to obtain a yellow oil. $^1$H NMR (400 MHz, CD$_3$CN) δ 9.04 (s, 1H), 8.71 (dd, J=10.8, 5.5 Hz, 4H), 8.53 (d, J=8.4 Hz, 1H), 8.45 (dd, J=4.5, 1.0 Hz, 1H), 8.37 (d, J=9.5 Hz, 1H), 8.32 (td, J=8.0, 1.5 Hz, 2H), 8.25 (td, J=8.0, 1.5 Hz, 1H), 8.21 (d, J=7.5 Hz, 2H), 8.15 (dd, J=11.5, 8.5 Hz, 2H), 8.07 (s, 2H), 8.03 (t, J=8.0 Hz, 1H), 7.94 (d, J=8.0 Hz, 1H), 7.85-7.63 (m, 6H), 4.35-4.00 (m, 8H), 3.42 (t, J=7.0 Hz, 2H), 2.71 (dd, J=14.0, 2.0 Hz, 1H), 2.64 (t, J=7.0 Hz, 2H), 2.59 (d, J=14.0 Hz, 1H), 2.48 (dd, J=14.0, 10.0 Hz, 1H), 2.37 (dd, J=14.0, 9.5 Hz, 1H), 2.28-2.16 (m, 2H), 2.00 (d, J=5.0 Hz, 1H), 1.97 (p, J=2.5 Hz, 1H). LRMS (ESI+): m/z: calcd for C$_{47}$H$_{46}$N$_7$O$_2$: 740.93; found: 740.71. HRMS (ESI+): m/z: calc'd for C$_{47}$H$_{46}$N$_7$O$_2$: 740.3708; found: 740.3711.

Example 30: 5-(diethylamino)-2-formylphenyl trifluoromethanesulfonate (II-15A)

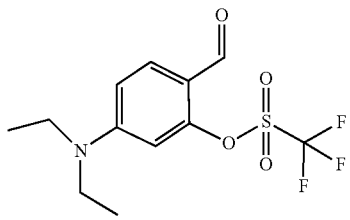 [SMILES: CCN(CC)c1ccc(C=O)c(OS(=O)(=O)C(F)(F)F)c1]

A solution of 4-(diethylamino)salicylaldehyde (300 mg, 1.55 mmol) in 21 mL of DCM, was added pyridine (0.251 mL, 3.1 mmol) and trifluoromethanesulfonic acid (0.495 mL, 2.94 mmol) under a nitrogen atmosphere at 0° C. The reaction mixture was stirred for 4 h, and then quenched with water. This mixture was washed further with water and extracted with DCM, before being dried with magnesium sulfate and filtered. The resultant solution was evaporated down in vacuo. The crude was then purified via flash chromatography (8:1 Hexane/EtOAc) to obtain a white powder (336 mg, 66.7%). $^1$H NMR (400 MHz, CDCl$_3$) δ 9.91 (s, 1H), 7.74 (d, J=9.0 Hz, 1H), 6.64 (dd, J=9.0, 2.5 Hz, 1H), 6.42 (d, J=2.5 Hz, 1H), 3.42 (q, J=7.0 Hz, 1H), 1.21 (t, J=7.0 Hz, 1H). $^{13}$C NMR (100 MHz, CDCl$_3$) δ 184.50, 152.96, 152.19, 132.21, 120.11, 116.92, 115.78, 110.24, 102.96, 44.92, 11.96. $^{19}$F NMR (376 MHz, CDCl$_3$) δ -74.32 (s). LRMS (ESI+) m/z calc'd C$_{12}$H$_{15}$F$_3$NO$_4$S [M+H]$^+$ 326.06, found 326.23.

Example 31: N,N-bis(pyridin-2-ylmethyl)-3-(4,4,5,5-tetramethyl-1,3,2-dioxaborolan-2-yl)propan-1-amine (II-15B)

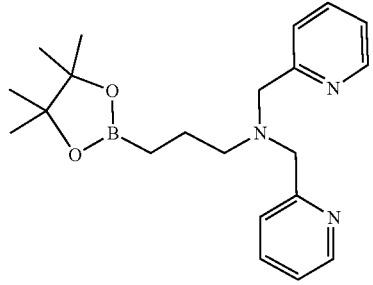 [SMILES: CC1(C)OB(CCCN(Cc2ccccn2)Cc2ccccn2)OC1(C)C]

A microwave vial charged with bis(2-pyridylmethyl)amine, 3-bromopropylboronic acid pinacol ester and K2CO3 in MeCN, was stirred at 60° C. for 24 hours. The reaction mixture was extracted with water and ethyl acetate. The combined organic phases were dried with sodium sulfate and concentrated down in vacuo to give the crude material. The crude was then purified via flash chromatography (Hexane/EtOAc) to obtain a white powder (177 mg, 48%). $^1$H NMR (400 MHz, CDCl$_3$) δ 8.44 (d, J=4.5 Hz, 2H), 7.59 (t, J=7.5 Hz, 2H), 7.52 (d, J=7.5 Hz, 2H), 7.07 (t, J=6.0 Hz, 2H), 3.75 (s, 4H), 2.45 (t, J=7.5 Hz, 2H), 1.62 (p, J=8.0 Hz, 2H), 1.13 (s, 12H), 0.69 (t, J=8.0 Hz, 2H). $^{13}$C NMR (101 MHz, CDCl$_3$) δ 160.10, 148.63, 136.18, 122.56, 121.58, 82.74, 74.71, 60.19, 56.48, 24.69, 24.58, 21.35. LRMS (ESI+) m/z calc'd C$_{21}$H$_{30}$BN$_3$O$_2$Na [M+Na]$^+$ 390.29, found 390.49.

Example 32: 2-(3-(bis(pyridin-2-ylmethyl)amino)propyl)-4-(diethylamino)benzaldehyde (II-15C)

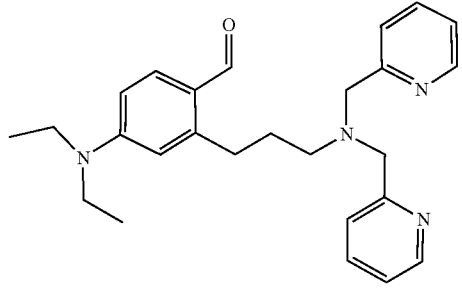 [SMILES: CCN(CC)c1ccc(C=O)c(CCCN(Cc2ccccn2)Cc2ccccn2)c1]

To a stirred solution of II-15A (100 mg, 0.307 mmol) in 1.1 mL THF was added II-15B (169 mg, 0.461 mmol), 3 M NaOH (0.3 mL, 0.896 mmol), and 1,1'-bis-(diphenylphosphinoferrocene)Pd (45 mg, 0.0614 mmol). The reaction mixture was heated at 100° C. for 2 h. After cooling to room temperature, the solution was concentrated down in vacuo. The residue with ethyl acetate and water. The organic layer was dried with magnesium sulfate and evaporated. The crude material was purified by preparative TLC (3% MeOH in DCM) to give the product (49.2 mg, 38.4%). LRMS (ESI+) m/z calc'd C$_{26}$H$_{32}$N$_4$ONa [M+Na]$^+$ 439.56, found 439.44.

Example 33: (E)-2-(benzo[d]thiazol-2-yl)-3-(2-(3-(bis(pyridin-2-ylmethyl)amino)propyl)-4-(diethylamino)phenyl)acrylonitrile (II-15)

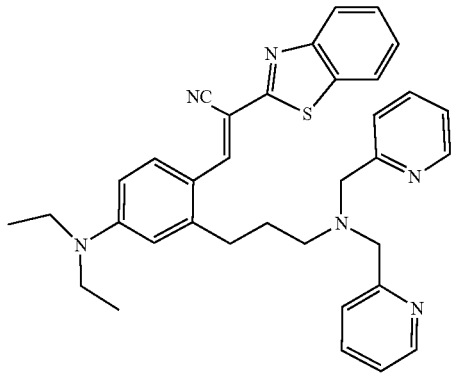

To a stirred solution of II-15C (49.2 mg, 0.118 mmol) in 1.2 mL EtOH was added benzothiazole-2-acetonitrile (20.6 mg, 0.118 mmol) under an nitrogen atmosphere. After, piperidine (11.7 uL, 0.118 mmol) was added and the reaction was left stirring overnight at ambient temperature. The resultant mixture was washed with 0.1% HCl, and the crude extracted via DCM, before being dried with magnesium sulfate and filtered. The resultant solution was evaporated in vacuo. The crude was purified with the use of preparative HPLC (0.1% TFA in 100% water to 100% ACN gradient). The collected fractions were lyophilized from ACN/Water to give the product (29 mg, 43%). $^1$H NMR (400 MHz, MeOH-d$_4$) δ 8.36 (d, J=4.5 Hz, 2H), 8.31 (d, J=9.0 Hz, 1H), 8.29 (s, 1H), 7.89 (d, J=8.0 Hz, 1H), 7.86 (d, J=8.0 Hz, 1H), 7.67 (td, J=7.5, 1.5 Hz, 2H), 7.60 (d, J=8.0 Hz, 2H), 7.49 (t, J=7.2 Hz, 1H), 7.41 (t, J=7.6 Hz, 1H), 7.18-7.13 (m, 2H), 6.64 (dd, J=9.0, 2.5 Hz, 1H), 6.50 (d, J=2.5 Hz, 1H), 3.82 (s, 4H), 3.45 (q, J=7.0 Hz, 4H), 2.79 (t, J=8.0 Hz, 3H), 2.66 (t, J=8.0 Hz, 3H), 1.93-1.77 (m, 3H), 1.19 (t, J=7.0 Hz, 6H). $^{13}$C NMR (100 MHz, MeOH-d$_4$) δ 165.54, 159.04, 153.47, 151.04, 147.98, 147.27, 144.23, 137.24, 134.07, 130.41, 126.49, 123.40, 122.35, 122.19, 121.36, 117.19, 111.90, 109.60, 96.36, 59.91, 53.73, 44.21, 31.59, 29.50, 11.80. HRMS (ESI+): m/z: calc'd for $C_{35}H_{37}N_6S$ [M+H]$^+$ 573.2795; found: 573.2786.

Example 34: 4-(diethylamino)-2-(3-oxopropyl)benzaldehyde (II-16A)

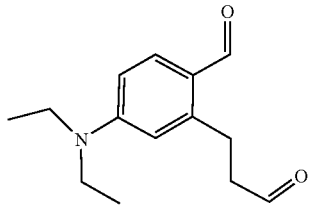 [SMILES: CCN(CC)c1ccc(C=O)c(CCC=O)c1]

In a microwave vial, allyl alcohol (0.0136 mL, 0.2 mmol) was added to a mixture of II-15A (78.1 mg, 0.24 mmol), palladium acetate (2.25 mg, 0.01 mmol), sodium bicarbonate (33.6 mg, 0.4 mmol) and tetrabutylammonium bromide (200 mg, 0.62 mmol) under a nitrogen atmosphere, and heated at 110° C. for 3 h. The resultant mixture was washed with cold aqueous 0.1 M HCl, extracted with DCM, and dried with magnesium sulfate. The resultant solution was evaporated in vacuo. The crude was purified via flash column chromatography (7:3 hexane/EtOAc) to give 2 as a yellow solid (10 mg, 21.4%). $^1$H NMR (400 MHz, CD$_2$Cl$_2$): 9.85 (1H, t, J=1.5 Hz), 9.82 (1H, s), 7.60 (1H, d, J=9.0 Hz), 7.28 (s, CDCl$_3$), 6.59 (1H, dd, J=9.0, 3.0 Hz), 6.49 (2H, d, J=3.0 Hz), 3.45 (4H, q, J=8.0 Hz), 3.32 (2H, t, J=7.5 Hz), 2.81 (2H, td, J=7.5, 1.5 Hz), 1.24 (6H, t, J=7.0 Hz); $^{13}$C NMR (100 MHz, CD$_2$Cl$_2$): 202.05, 190.26, 137.98, 113.05, 108.59, 77.01, 45.09, 44.61, 29.71, 26.93, 12.53. LRMS (ESI+) m/z calc'd $C_{14}H_{19}NO_2Na$ [M+Na]$^+$ 256.30, found 256.32.

Example 35: tri-tert-butyl 10-(3-(5-(diethylamino)-2-formylphenyl)propyl)-1,4,7,10-tetraazacyclododecane-1,4,7-tricarboxylate (II-16B)

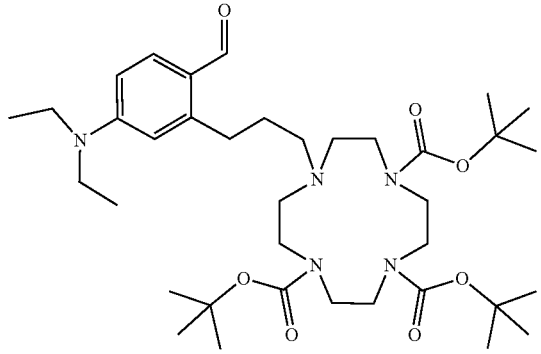 [SMILES: CCN(CC)c1ccc(C=O)c(CCCN2CCN(C(=O)OC(C)(C)C)CCN(C(=O)OC(C)(C)C)CCN(C(=O)OC(C)(C)C)CC2)c1]

A solution of II-16A (29.2 mg, 0.125 mmol) in 0.5 ml of DCE was added to a solution of Boc$_3$cyclen (47.3 mg, 0.1 mmol) in 0.5 mL of DCE in a rbf at 0° C., and stirred together with 4 Å molecular sieves for 2 h under nitrogen atmosphere. Sodium triacetoxyborohydride (31.8 mg, 0.15 mmol) in 0.2 mL of DCE was then added, and the reaction stirred for 24 h at rt. The resultant mixture was washed with water, extracted with DCM, and dried under magnesium sulfate. The solution was evaporated down in vacuo. The crude was purified by flash chromatography (1:1 Hexane/EtOAc) to give an orange solid (50 mg, 58%). $^1$H NMR (400 MHz, CD$_2$Cl$_2$): 9.87 (1H, s), 7.64 (1H, d, J=8.8 Hz), 6.58 (1H, dd) 6.43 (1H, d, J=8.8 Hz), 3.6-2.6 (16H, m), 1.60 (4H, s), 1.48 (9H, s), 1.45 (18H, s), 1.30-1.22 (6H, m). $^{13}$C NMR (100 MHz, CD$_2$Cl$_2$): 189.93, 151.34, 112.28, 108.55, 79.19, 77.01, 44.54, 29.71, 28.72, 28.51, 12.59. LMRS (ESI+) m/z calc'd $C_{37}H_{64}N_5O_7$ [M+H]$^+$ 690.95, found 690.64.

Example 36: tri-tert-butyl (E)-10-(3-(2-(2-(benzo[d]thiazol-2-yl)-2-cyanovinyl)-5-(diethylamino)phenyl)propyl)-1,4,7,10-tetraazacyclododecane-1,4,7-tricarboxylate (II-16C)

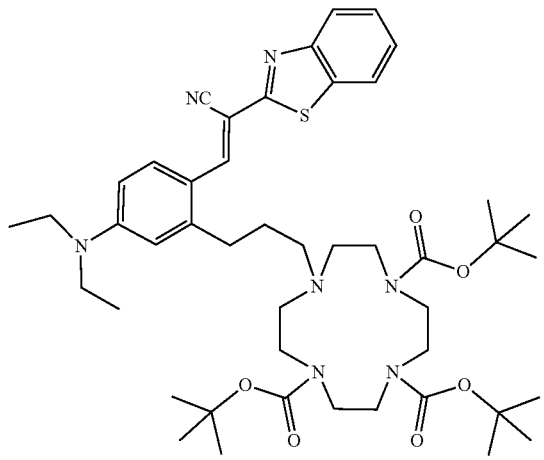

To a stirred solution of II-16B (50 mg, 0.0725 mmol) in 1 mL EtOH was added benzothiazole-2-acetonitrile (13.9 mg, 0.0798 mmol) under a nitrogen atmosphere. After, piperidine (21.5 uL, 0.217 mmol) was added and the reaction was left stirring overnight at ambient temperature. The resultant mixture was washed with 0.1% HCl, and the crude extracted via DCM, before being dried with magnesium sulfate and filtered. The resultant solution was evaporated in vacuo. The crude material was purified by flash chromatography (7:3 Hexane/EtOAc) to give a red solid (30 mg, 48.9%). $^1$H NMR (400 MHz, $CD_2Cl_2$): 8.45-6.4 (15H), 4.15 (2H, q, J=7.2 Hz), 3.54-3.15 (21H, m), 1.48-1.42 (28H, m), 1.31-1.26 (34H, m) 0.94-0.81 (21H, m). LMRS (ESI+) m/z calc'd $C_{46}H_{68}N_7O_6S$ [M+H]$^+$ 847.15, found 846.75.

Example 37: (E)-3-(2-(3-(1,4,7,10-tetraazacyclododecan-1-yl)propyl)-4-(diethylamino)phenyl)-2-(benzo[d]thiazol-2-yl)acrylonitrile (II-16)

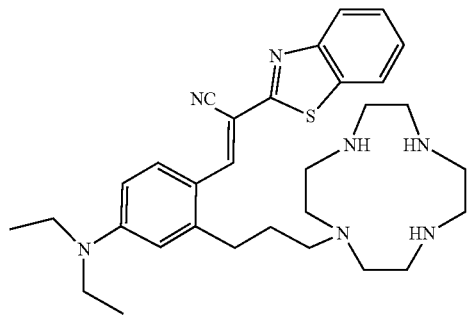

85% wt Phosphoric Acid (0.0592 ml, 1.02 mmol) was added to II-16C (30 mg, 0.0355 mmol) in 0.3 mL of DCM under $N_2$, and the reaction was stirred overnight at rt. The solution was cooled to 0° C., and 1 mL of water was added. The reaction was then quenched with 2M NaOH, and resultant mixture was filtered to give a red precipitate. The crude was purified with the use of preparative HPLC (0.1% TFA in 100% water to 100% ACN gradient). The collected fractions were lyophilized from ACN/Water to give II-16 as a red crystal (1 mg, 5%); LRMS (ESI+) m/z calc'd for $C_{31}H_{44}N_7S$ [M+H]$^+$ 546.80, found 546.54.

Example 38: Compound II-17

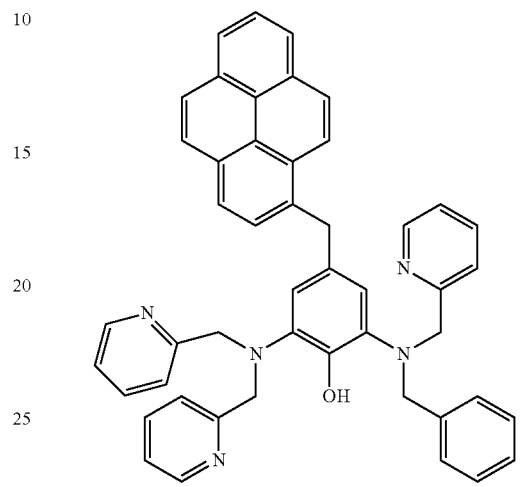

Example 39: N,N-bis(pyridin-2-ylmethyl)pyrene-1-carboxamide (II-18)

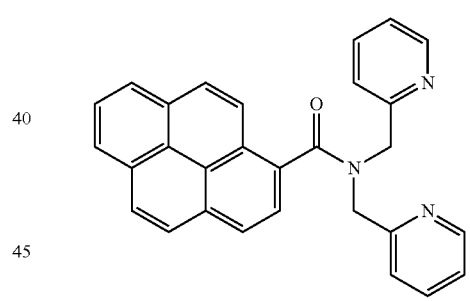

To a solution of 1-pyrenecarboxylic acid (50 mg, 0.2 mmol) in DCM (2 mL) was added oxalyl chloride (51.5 μL, 0.6 mmol). One drop of DMF was also injected as a catalyst. The resulting mixture was stirred at room temperature for 4 h. Evaporation of the volatiles yielded pyrene-1-carbonyl chloride. The product was dissolved in DCM (1 mL) and was added dropwise to the solution of DPA (183 μL, 1.02 mmol) in DCM (2.5 mL). The resulting solution was stirred at room temperature for 3 h. The reaction mixture was washed with distilled water, evaporated, and concentrated to dryness to afford the product as a yellowish oil. 1H NMR (400 MHz, DMSO-d$_6$) δ 8.72 (dt, J=5, 1.5 Hz, 1H), 8.54-8.48 (m, 1H), 8.44-8.02 (m, 9H), 7.90 (td, J=8, 2 Hz, 1H), 7.65 (td, J=8, 2 Hz, 1H), 7.57 (d, J=8 Hz, 1H), 7.41 (ddd, J=8, 5, 1 Hz, 1H), 7.24 (ddd, J=8, 5, 1 Hz, 1H), 7.11 (d, J=8 Hz, 1H), 5.24 (s, 1H), 4.74 (s, 1H), 4.51 (d, J=14 Hz, 2H). $^{13}$C NMR (100 MHz, DMSO-d$_6$) δ 171.41, 157.38, 156.58, 149.77, 149.75, 137.43, 137.25, 131.81, 131.41, 131.17, 130.78, 128.80, 128.51, 127.64, 127.44, 127.11, 126.25, 126.08, 125.05, 124.89, 124.47, 124.12, 124.08, 123.03, 122.98, 122.71, 122.20, 54.48, 50.33. LRMS (ESI+) m/z calc'd for $C_{29}H_{21}N_3ONa$ [M+Na]$^+$ 450.50, found 450.41.

Example 40: Compound II-19

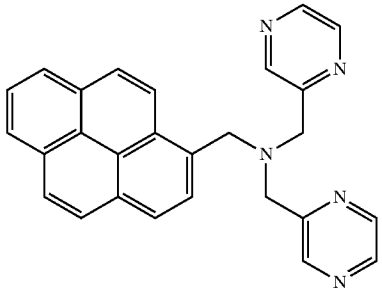 [SMILES: c1cc2ccc3ccc(CN(Cc4cnccn4)Cc4cnccn4)c4ccc(c1)c2c34]

Example 41: Formation of Zinc Chelates (Compounds of Formula I)

To a solution of the compound of Formula II (1 equivalent) in ACN was added Zn(OTf)$_2$ (1 equivalent). After stirring for 2 h at room temperature, distilled water was added and the solution was lyophilized to give the compounds of Formula I.

Example 42 Lipid Detection

Example 42.1 Vesicle Preparation

Small Unilamellar Vesicles (SUVs) were prepared by the extrusion method. Appropriate amounts of lipid in the desired proportions were weighed out to create 10 mM liposome suspensions. The lipids were then dissolved in a minimum amount of chloroform and vortexed to ensure thorough mixing. The excess solvent was then dried off under a gentle stream of nitrogen and allowed to dry overnight in a vacuum dessicator to remove any remaining traces of solvent. The resulting lipid film was then hydrated with 2 mL of HEPES buffer (50 mM HEPES, pH 7.5) for 1 h. The sample was then subjected to five cycles of freeze-thaw-vortex, cycling between liquid nitrogen and a 60° C. water bath. The resulting suspension of multilamellar vesicles (MLVs) was then extruded 25 times through a 0.1 µm polycarbonate membrane installed in a mini-extruder (Avanti Polar Lipids, Alabaster, AL) to form SUV.

Example 42.2 Serial Dilution Vesicle Fluorescence Intensity Experiments 10 mM stock solutions of vesicles were diluted separately to 400 µM and 80 µM in pH 7.5, 50 mM HEPES buffer. Two concentration ranges were prepared through serial dilutions (400-42 µM, 4:5 dilution; 80-4 µM, 3:4 dilution). The sensors were dissolved to a concentration of 50 µM (from 800 µM stock solutions in 100% DMSO) in 50 mM HEPES, pH 7.5, 10% DMSO buffer. 30 µL of the vesicle solutions were combined with 30 µL of sensor solutions, the mixtures were incubated for 10 min away from light, and the fluorescence intensity was recorded at 476 nm (10 nm bandwidth) following excitation at 350 nm. For the monomer of sensor compounds, emission at 376 nm (10 nm bandwidth) was measured following excitation at 350 nm (5 nm bandwidth). Fluorescence intensities measured were used to calculate the following parameters: $\Delta FI_{exc}$, $\Delta\Delta FI_{exc}$, $\Delta FI_{mon}$, $\Delta\Delta FI_{mon}$, $\Delta\Delta FI_{exc/mon}$ and $\Delta\Delta\Delta FI$. The following equations were used for the calculations:

$$\Delta FI_{exc} = \frac{FI_{exc\,sensor+vesicle}}{FI_{exc\,sensor}} \quad \text{Equation 1}$$

$$\Delta\Delta FI_{exc} = \frac{\Delta FI_{exc\,vesicle}}{\Delta FI_{exc\,100\%\,PC}} \quad \text{Equation 2}$$

$$\Delta FI_{mon} = \frac{FI_{mon\,sensor+vesicle}}{FI_{mon\,sensor}} \quad \text{Equation 3}$$

$$\Delta\Delta FI_{exc/mon} = \frac{\Delta FI_{exc}}{\Delta FI_{mon}} \quad \text{Equation 4}$$

$$\Delta\Delta FI_{mon} = \frac{\Delta FI_{mon\,vesicle}}{\Delta FI_{mon\,100\%\,PC}} \quad \text{Equation 5}$$

$$\Delta\Delta\Delta FI = \frac{\Delta\Delta FI_{exc}}{\Delta\Delta FI_{mon}}. \quad \text{Equation 6}$$

To evaluate the potential of exemplary sensors of the application for selective detection of negatively charged phospholipids within biological and artificial lipid membrane structures, sensor compounds II were screened against small unilamellar vesicles, composed of (unless otherwise stated) 50% (mol) POPC (PC) and 50% of POPE (PE), DOPS (PS), POPG (PG), POPA (PA) or TOCL (CL). Of these, PC and PE represented the zwitterionic vesicles; PS (−1), PA (−1), PG (−1) and CL (−2) represented the negatively charged vesicles. The commercially available sensor for the detection of negatively charged membranes, PSVue™ 380, was tested alongside sensors compounds Ia to allow direct comparison of the sensitivity and selectivity profiles.

The initial proof-of-concept experiment was conducted to probe whether compound I-1 selectively detected negatively charged vesicles over the zwitterionic vesicles. Compound I-1 (25 µM) was incubated with or without zwitterionic PC or PE vesicles, or negatively charged PS, PG, PA, or CL vesicles (2-200 µM) in 50 mM HEPES, pH 7.5, 5% DMSO, and fluorescence intensity corresponding to excimer emission (476 nm) was measured. The fluorescence enhancement of the excimer ($\Delta FI_{exc}$) species in the presence of vesicles was calculated using equation 1, which is defined as the ratio of the emission intensities of the sensor-vesicle sample and the sensor alone.

Figure 2:
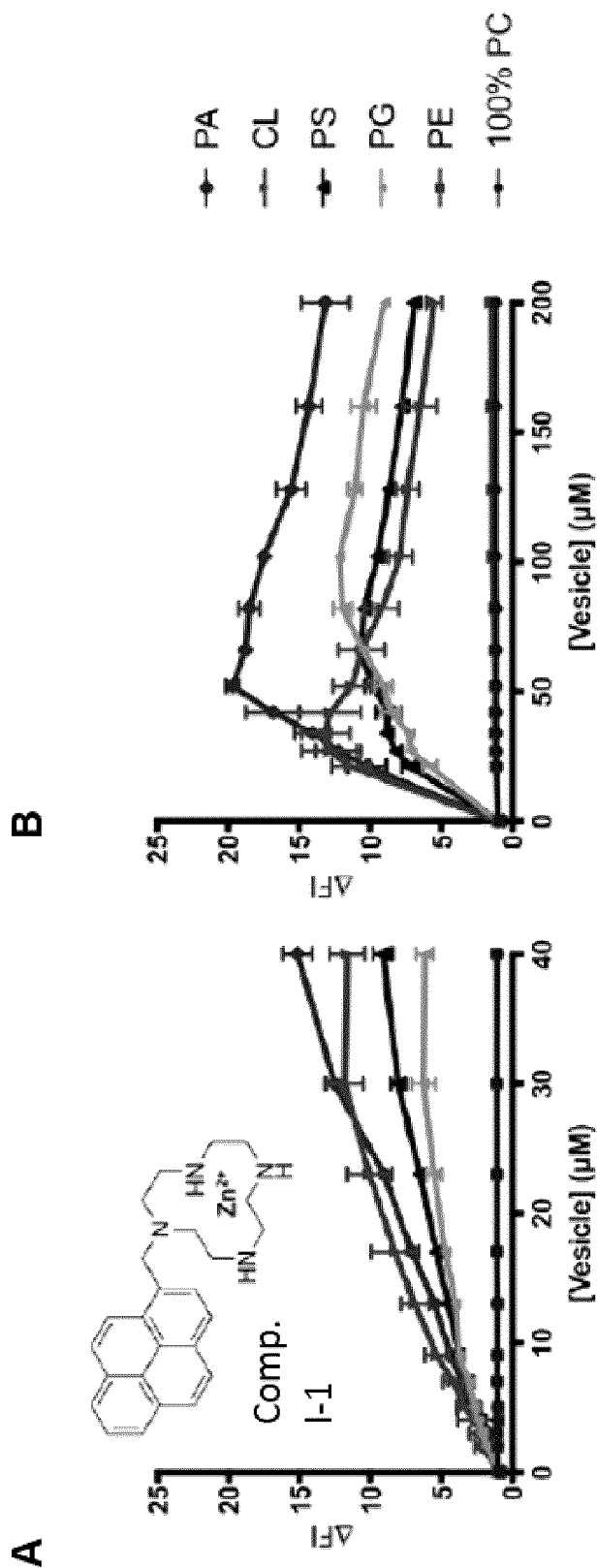
FIG. 2 shows the excimer fluorescence enhancement of exemplary compound I-1 upon addition of zwitterionic (PC, PE) and negatively charged (PA, PS, PG, CL) vesicles. Panel A shows the $\Delta FI_{exc}$ of compound I-1 at vesicle concentrations between 0-40 μM. Panel B shows the $\Delta FI_{exc}$ of compound I-1 at vesicle concentrations between 0-200 μM. Buffer: 50 mM HEPES, 5% DMSO, pH 7.5. [Ia-1]=25 μM. $\lambda_{ex/em}$=350/476 nm.

FIG. 2 panels A and B show that sensor compound I-1 selectively detected all negatively charged vesicles ($\Delta FI_{exc} \geq 5$) over the two zwitterionic vesicles ($\Delta FI_{exc} \sim 1$) at different vesicle concentrations. PA vesicles were detected best, with $\Delta FI$ values reaching 20 at 50 µM PA vesicle concentration, closely followed by CL, and further by PS and PG. While not wishing to be limited by theory, higher sensitivity to PA and CL vesicles could be attributed to the higher negative charge associated with these lipids: the head group of PA contains a phosphate-monoester (as compared to the phosphate-diester in CL, PG and PS) affording a doubly-ionizable phosphate group, while CL contains two phosphate-diester groups per lipid molecule (PA, PG, and PS contain one). Additionally, while not wishing to be limited by theory, the phosphate-monoester of PA is less sterically hindered, which could facilitate more optimal binding of the sensor molecules. A linear response was, on average, observed from 2 to 40 µM vesicles (50 µM for PA) (panel A), followed by a gradual decrease in signal at higher vesicle concentration (panel B). The observed decrease is consistent with the proposed $[1:1]_2$ sensing mechanism of the sensor compounds; the excimer-emitting $[1:1]_2$ complex dissociates in favour of forming monomer-emitting $[1:1]_2$ complexes. The zwitterionic PC and PE vesicles were not detected, with an excimer signal almost identical to that of the sensor alone. This is consistent with the proposed sensing mechanism (FIG. 1B), which relies on the coordinative interaction between the negatively charged phospholipid head group and the Lewis acid $Zn^{2+}$ of the sensors.

Following the validation that the sensor compound I-1 is suitable for the selective detection of vesicles containing negatively charged lipids, the remaining exemplary sensors compounds of Formula I were investigated with the goal of identifying a sensor derivative which would afford maximum sensitivity and selectivity for negatively charged vesicles. For each sensor, monomer (376 nm) and excimer (476 nm) emission intensities ($FI_{mon}$ and $FI_{exc}$, respectively) were recorded, and were used to calculate the following parameters: $\Delta FI_{exc}$ (hereon referred to as $\Delta FI$; Equation 1); $\Delta\Delta FI_{exc}$ (hereon referred to as $\Delta\Delta FI$; Equation 2); $\Delta FI_{mon}$ (Equation 3); $\Delta\Delta FI_{exc/mon}$ (Equation 4); $\Delta\Delta FI_{mon}$ (Equation 5) and $\Delta\Delta\Delta FI$ (Equation 6). $\Delta\Delta FI$ parameter was used to provide an unbiased quantification of sensors' selectivity for negatively charged over zwitterionic vesicles by expressing the signal as a ratio of the $\Delta FI$ of each vesicle to the $\Delta FI$ of a zwitterionic PC vesicle, (Equation 2).

Figure 3:
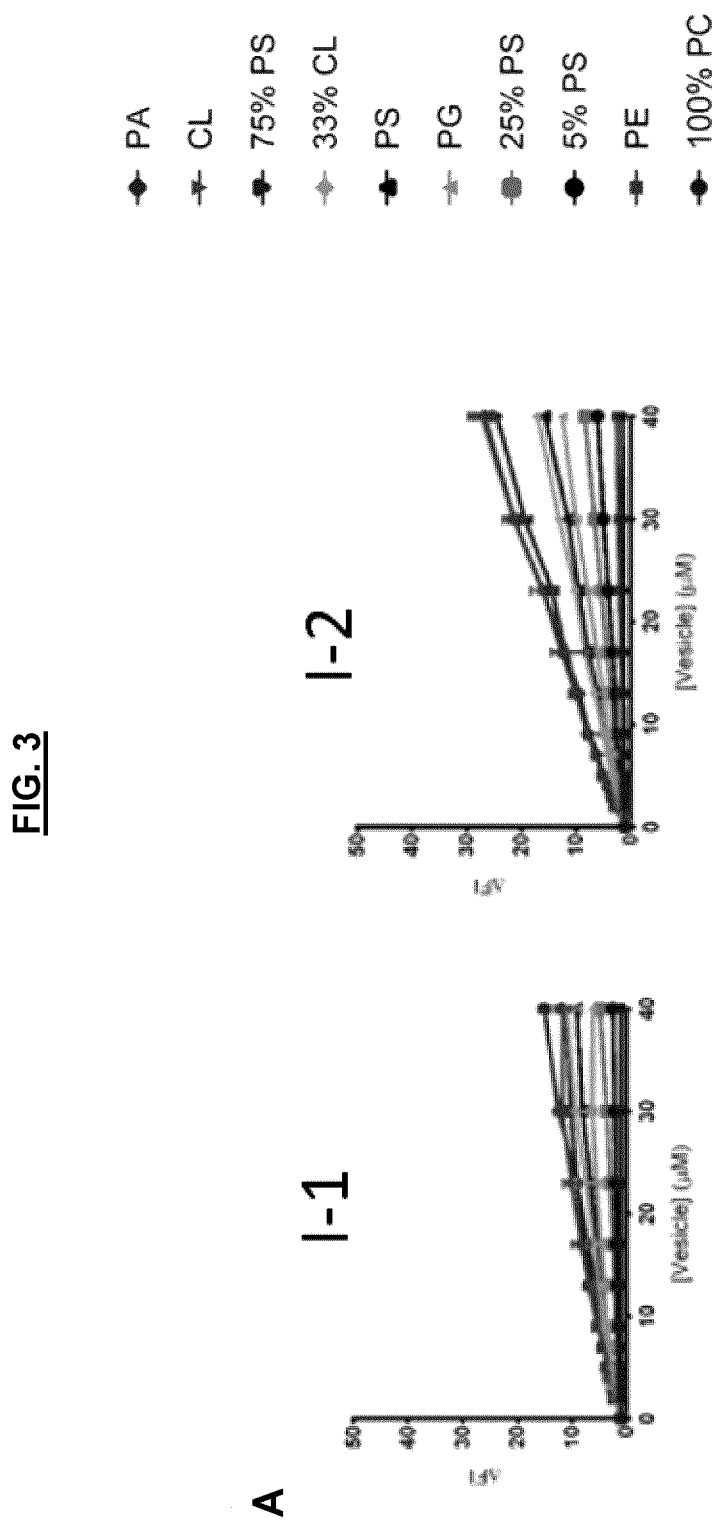
FIG. 3 shows the $\Delta FI_{exc}$ data for exemplary compounds I-2, I-3, I-4, I-5, and I-6 and compounds II-1, II-4, and II-5 for various vesicles. Panel A shows data at vesicle concentrations from 0 to 40 μM. Panel B shows data at vesicle concentrations from 0 to 200 μM. Buffer: 50 mM HEPES, 5% DMSO, pH 7.5. [I and II compounds]=25 μM. $\lambda_{ex/em}$=350/476 nm.
Figure 3:
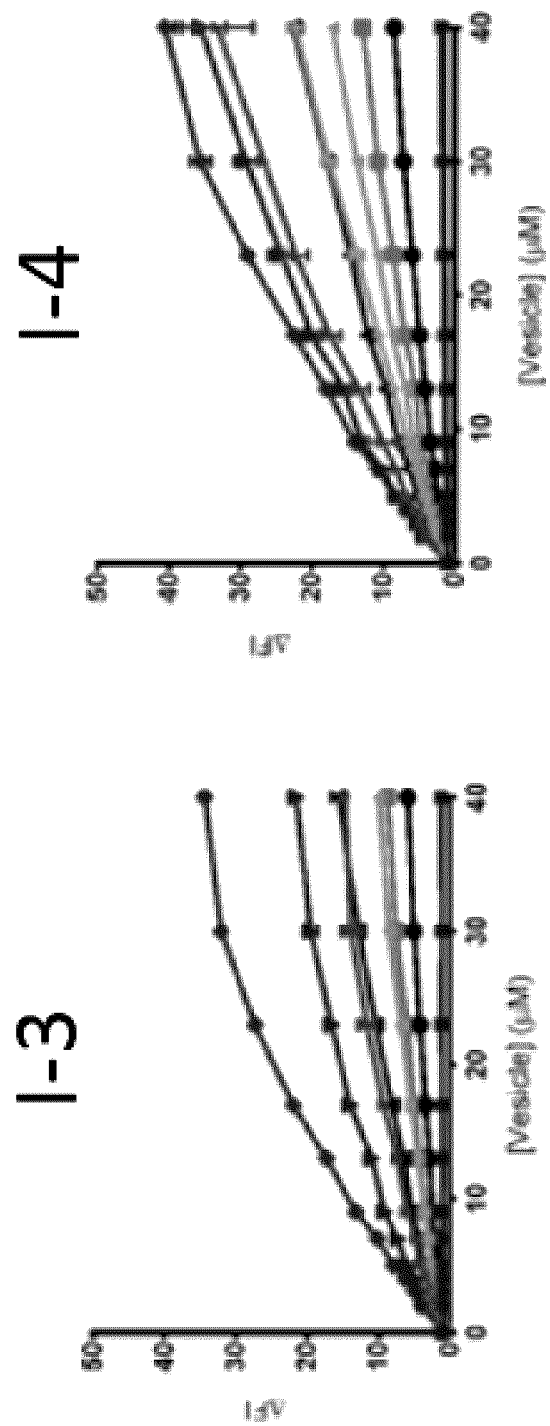
Figure 3:
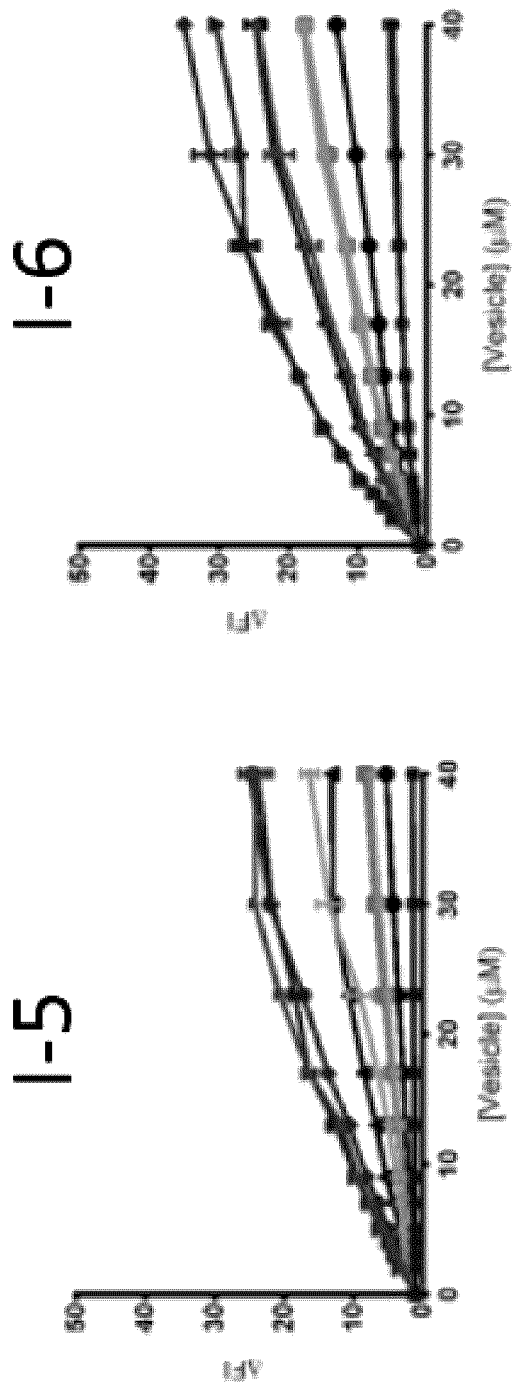
Figure 3:
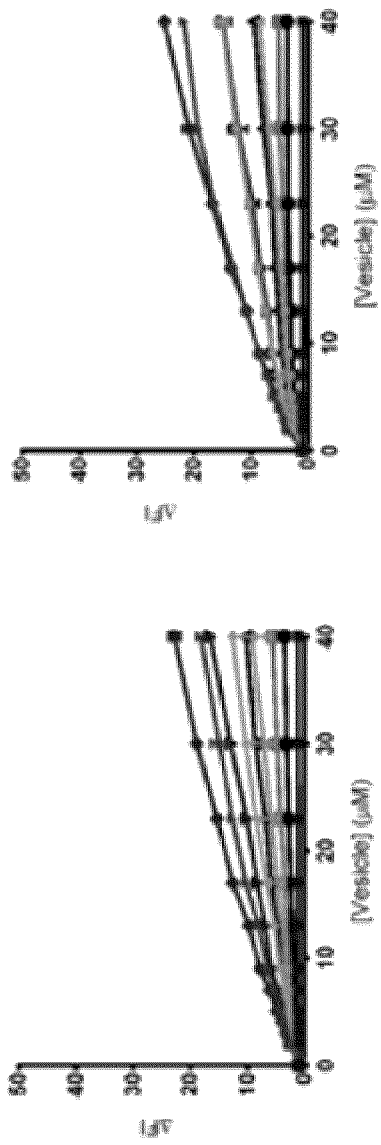
Figure 3:
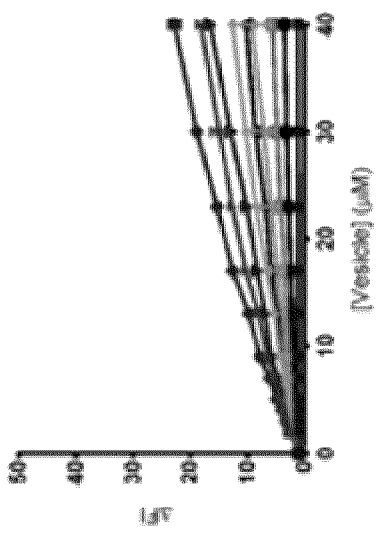
Figure 3:
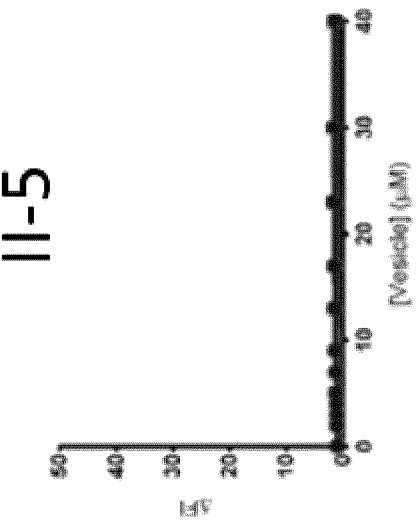
Figure 3:
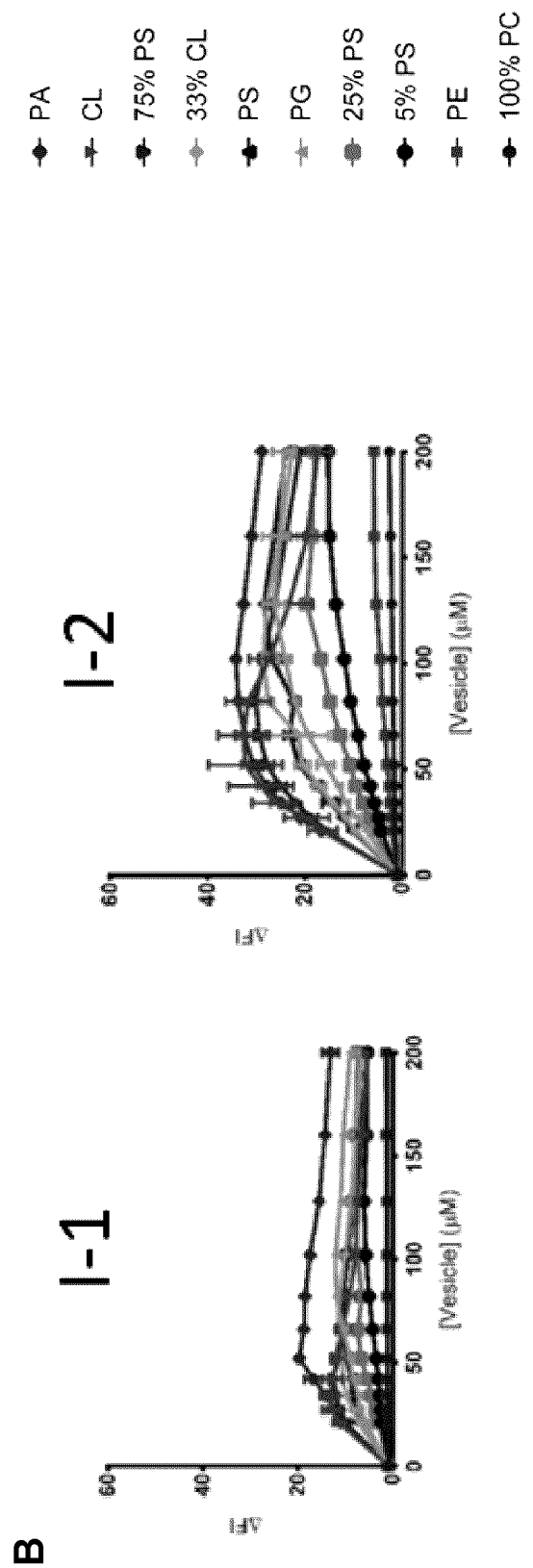
Figure 3:
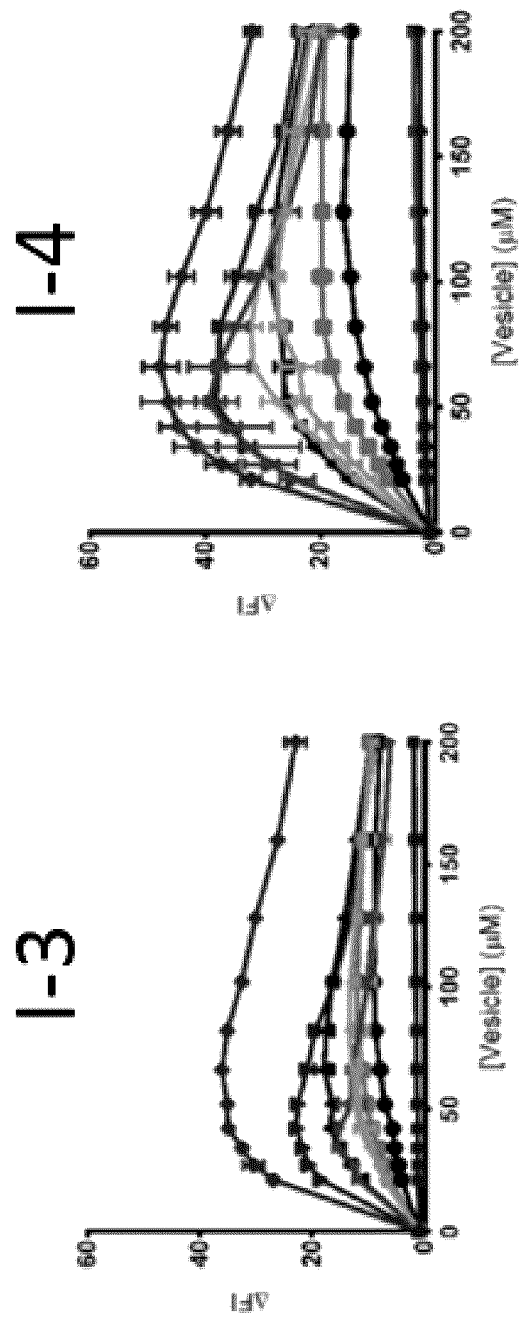
Figure 3:
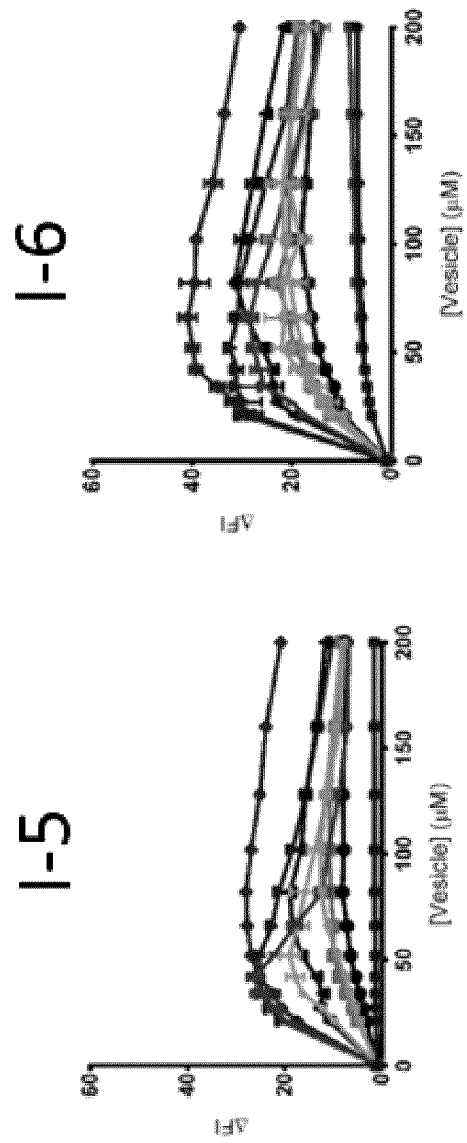
Figure 3:
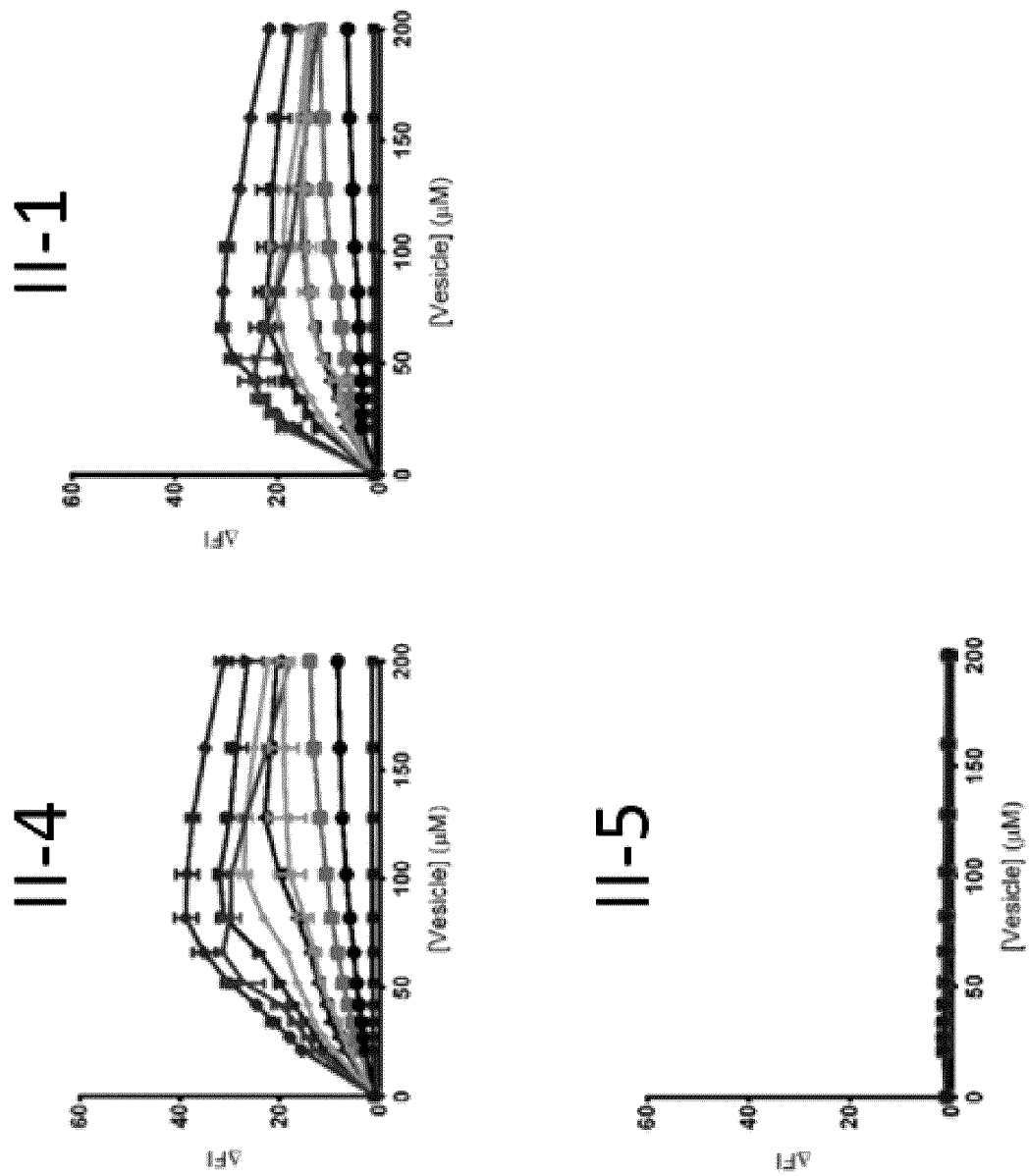
Figure 4:
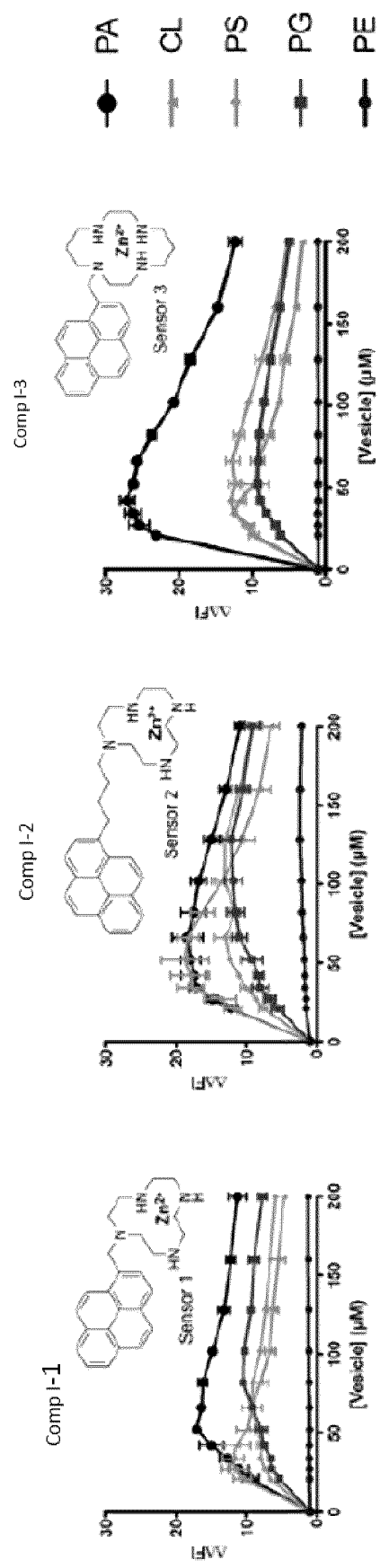
FIG. 4 shows the ΔΔFI for exemplary compounds I-1, I-2, I-3, I-4, I-5, I-6 and PSVue™380 for zwitterionic (PE) and negatively charged (PA, PS, PG, CL) vesicles at vesicle concentrations between 0-200 μM. Buffer: 50 mM HEPES, 5% DMSO, pH 7.5. [I and II compounds]=25 μM, $\lambda_{ex/em}$=350/476 nm. [PSVue™380]=1 μM, $\lambda_{ex/em}$=380/440 nm.
Figure 4:
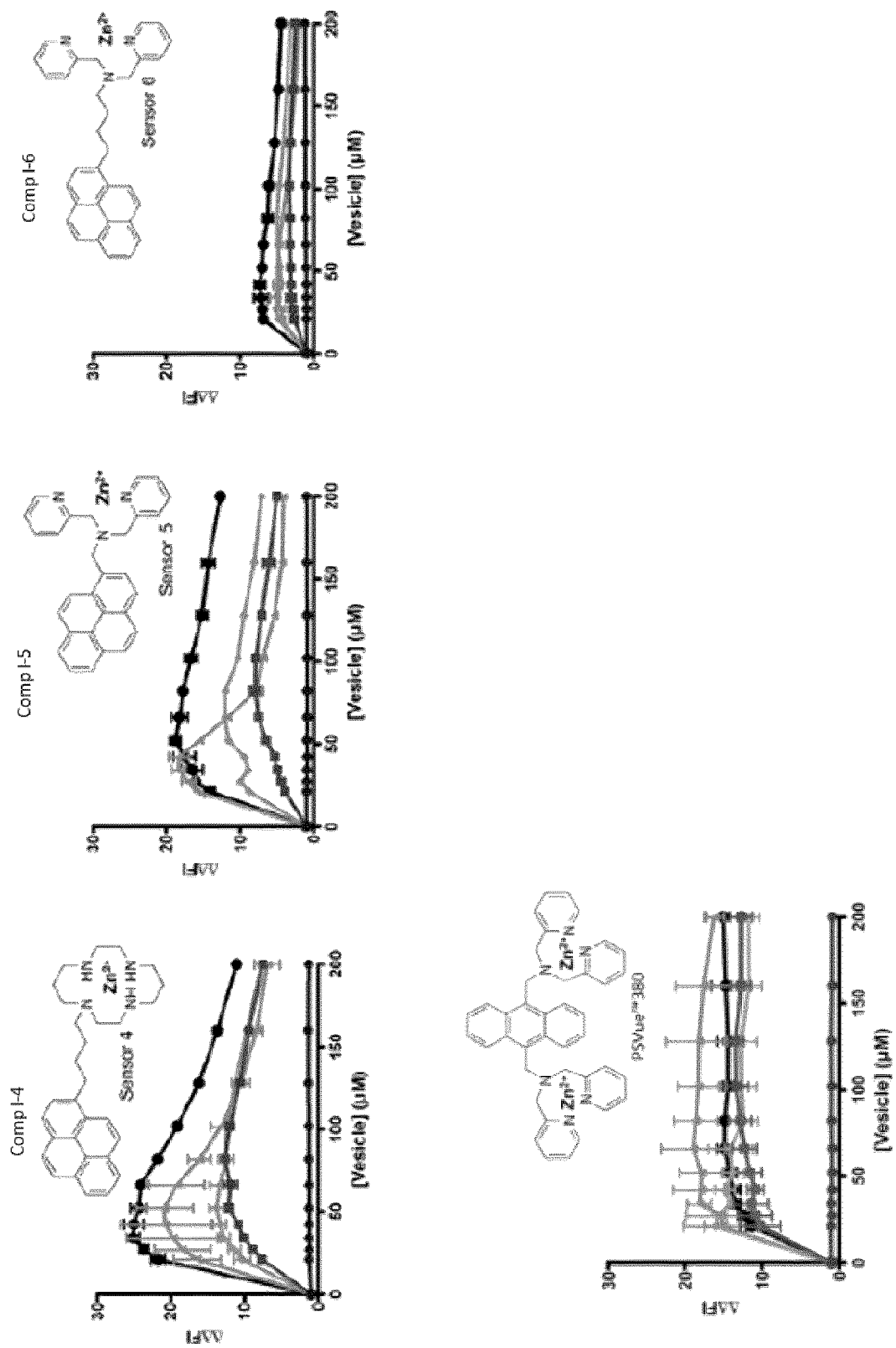
Figure 5:
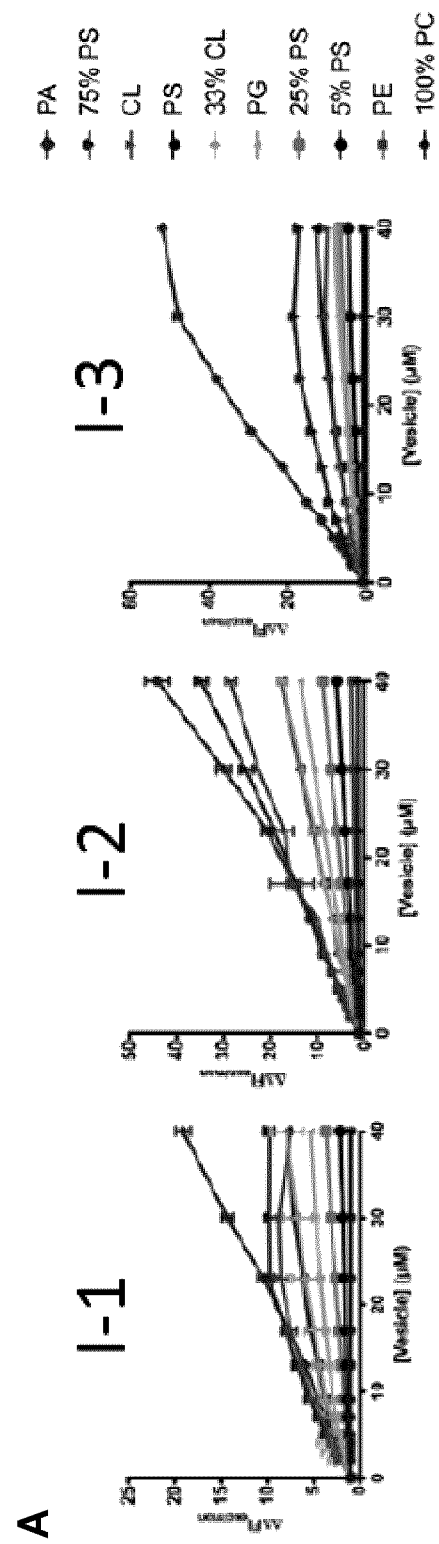
FIG. 5 shows the $\Delta\Delta FI_{exc/mon}$ data for exemplary compounds I-1, I-2, I-3, I-4, I-5, I-6 and compounds II-1, II-4, and II-5 for zwitterionic (PE) and negatively charged (PA, PS, PG, CL) vesicles. Panel A shows data at vesicle concentrations from 0 to 40 μM. Panel B shows data at vesicle concentrations from 0 to 200 μM. Buffer: 50 mM HEPES, 5% DMSO, pH 7.5. [I and II compounds]=25 μM, $\lambda_{ex/em}$=350/476 nm.
Figure 5:
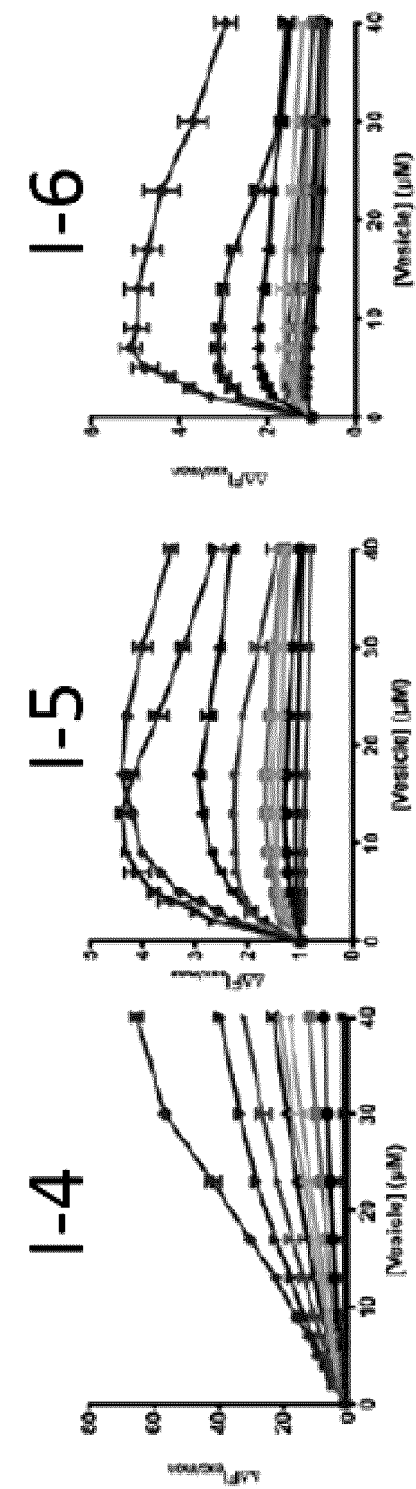
Figure 5:
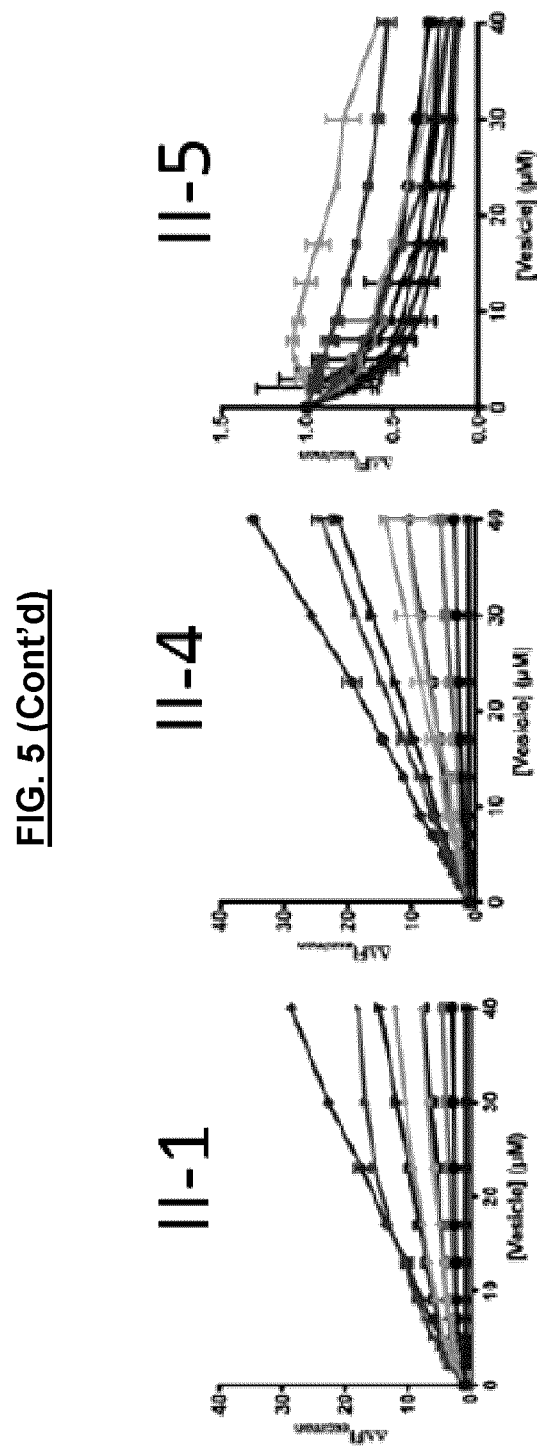
Figure 5:
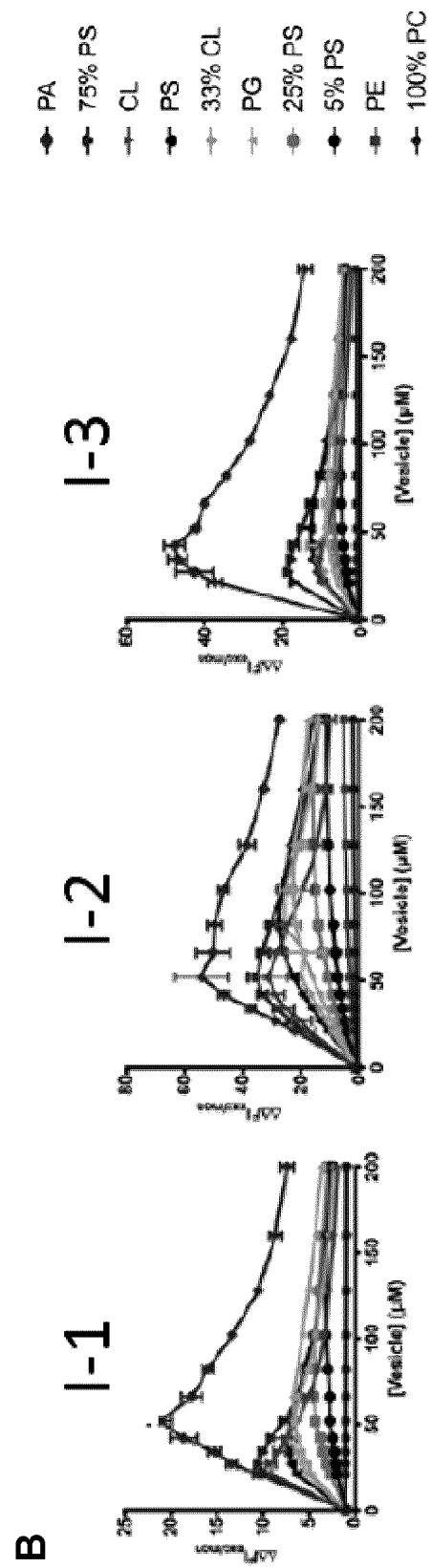
Figure 5:
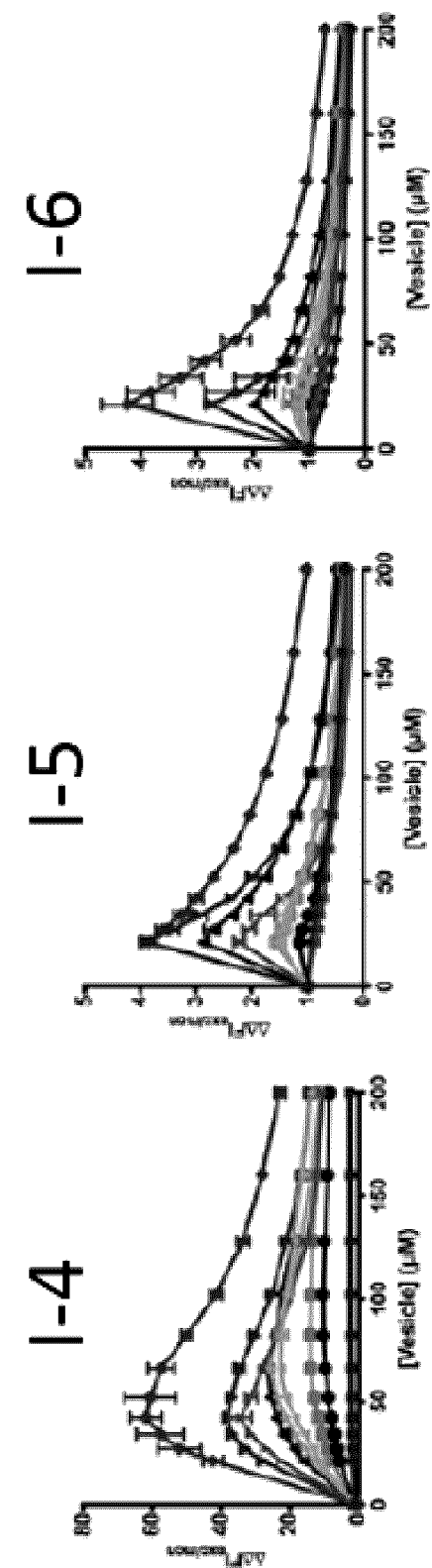
Figure 5:
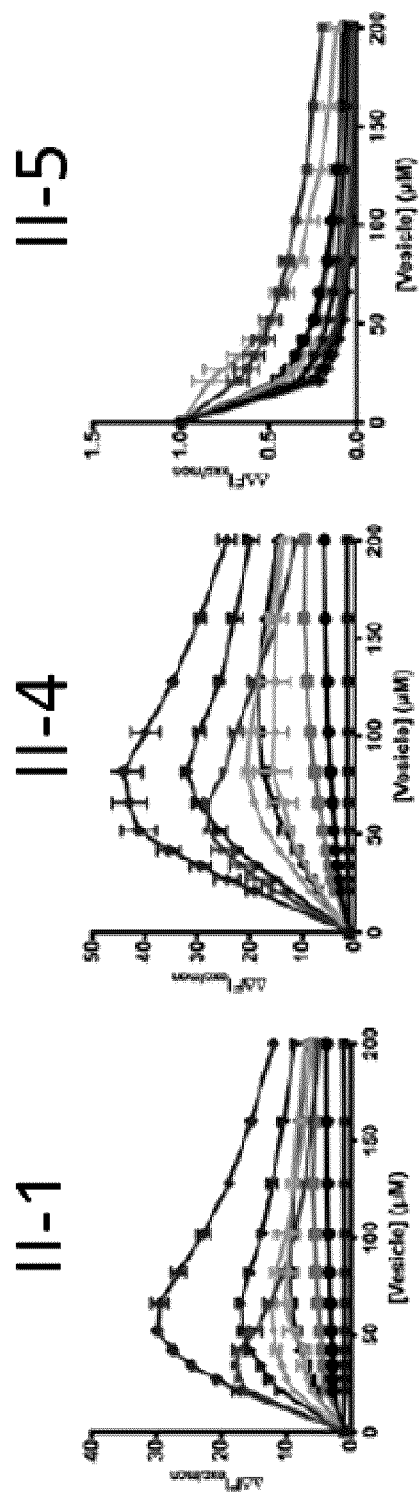

FIG. 3 shows $\Delta FI$ values of compounds I-1, I-2, I-3, I-4, I-5, I-6, and compounds II-1, II-4, and II-5 (Panel A for vesicle concentrations 0 to 40 μM, Panel B for vesicle concentration 0-200 μM). FIG. 4 shows the $\Delta\Delta FI$ values for compounds I-2, I-3, I-4, I-5, I-6 and PSVue™380. FIG. 5 shows $\Delta\Delta FI_{exc/mon}$ of I-1, I-2, I-3, I-4, I-5, I-6 and compounds II-1, II-4, and II-5 (Panel A for vesicle concentrations 0 to 40 μM, Panel B for vesicle concentration 0-200 μM).

All compounds of Formula I and PSVue™380 tested detected negatively charged, but not zwitterionic vesicles. All sensor compounds of Formula I exhibited a signal decrease in the presence of excess vesicles, suggesting that they operate by the same $[1:1]_2$ mechanism described above. On the other hand, PSVue™380 did not exhibit this signal decrease highlighting the difference in the sensing mechanisms. The increasing vesicle concentration is associated with a greater enhancement in excimer signal, as compared to that of monomer. As shown in FIG. 5, DPA-containing sensors such as compound I-6 exhibit very low $\Delta\Delta FI_{exc/mon}$, which, without wishing to be limited by theory, is attributed to analyte-mediated de-quenching of sensor fluorescence, where the monomer emission is affected to a greater extent. Thus, in further evaluating sensors' potency, only $\Delta\Delta FI$ parameter, which does not factor in monomer emission was used. Of the seven sensors tested, compound I-6 displayed the lowest $\Delta\Delta FI$ values (FIG. 4) for the negatively charged vesicles: the change in excimer fluorescence of I-6 in response to 100% PC vesicles ($\Delta FI$) approached ~7 (FIG. 4) resulting in the lower observed $\Delta\Delta FI$ values as compared to other sensors. While not wishing to be limited by theory, significant excimer formation of sensor 6 (compound I-6) in the presence of zwitterionic PC could be rationalized by the higher hydrophobicity of this sensor (contains a DPA group and a hydrophobic butyl linker) as compared to the other Ia compounds tested. With this notable PC detection, sensor compound I-6 was concluded to be sub-optimal for the selective detection of negatively charged vesicles. All exemplary sensor compounds for Formula I, and in particular sensor compounds I-3, but not PSVue™380, detected PA and CL vesicles to a greater extent (sensor compound I-3-PA $\Delta\Delta FI\sim 25$) than PS and PG vesicles. As mentioned above, while not wishing to be limited by theory, this may be attributed to the higher negative charge found in the PA and CL lipids as compared to their PS and PG counterparts. Surprisingly, PSVue™ 380 does not appear to be sensitive to the higher negative charge of the PA and CL lipids. In previous studies by Smith et. al, it was shown that PSVue™ 380 only detected PS as part of the vesicles, and not in its free monomeric form, suggesting that the sensing mechanism of PSVue™ 380 could require formation of a [2:1] lipid-sensor complex, with each of the two $Zn^{2+}$ centres interacting with a single phosphate group. It is likely that the conformational constraint imposed via formation of a [2:1] complex prohibits the further coordinative interaction offered through the additional negative charge in PA and CL. While not wishing to be limited by theory, significant selectivity of sensor 3 (compound I-3) for PA but not CL, may be attributed to the unique conformation of this sensor which translates into improved binding to the phosphate mono-ester as compared to the phosphate-diesters of the CL, PG, and PS.

Figure 6:
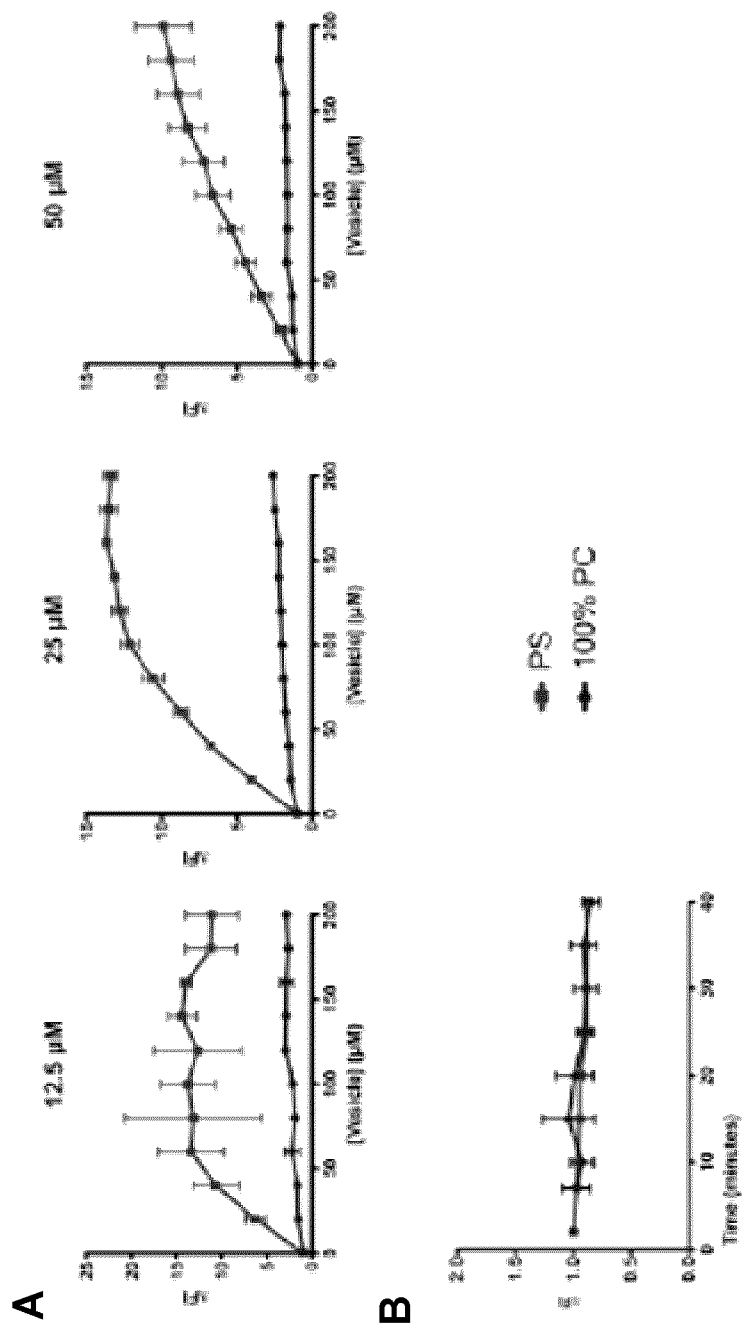
FIG. 6 shows in panel A the optimal sensor concentration testing by measuring ΔFI of sensor exemplary compound I-1 with PS and PC vesicles at varying concentrations of exemplary Ia-1. Panel B shows the ΔFI at 25 μM of I-1 at different incubation times. Buffer: 50 mM HEPES, 5% DMSO, pH 7.5. $\lambda_{ex/em}$=350/476 nm.

PSVue™380 displayed the smallest linear response (~2-10 μM), reaching full saturation >20 μM vesicles (FIG. 4). At 25 μM of sensor compounds I, a linear response is observed from 2 to a minimum of 40 μM vesicles (FIGS. 2A, 3A, and 5A); by increasing sensor compounds I concentration to 50 μM a linear response from ~5 to 200 μM can be achieved (FIG. 6A). Since the use of higher PSVue™380 concentrations leads to reduced sensitivity, it was proposed that exemplary sensors can be particularly useful in applications where quantification of negatively charged lipids over large concentration ranges is of interest. Table 1 summarizes the $\Delta\Delta FI$ for each vesicle-sensor combination at 5 and 20 μM vesicle concentrations, and allows more detailed comparison of sensors' performance. To facilitate visual comparison, within each row corresponding to a particular vesicle, the $\Delta\Delta FI$ for each sensor were ranked from lowest (light grey) to highest (dark grey). Notably sensors I-3 and I-4 are superior to PSVue™380 at sensing PA. Sensitivity comparable to that of PSVue™380 is also observed for the detection of 5 μM PS vesicles by sensors I-3 and I-4, and 20 μM CL vesicles by sensors I-4 and I-5. Sensor I-4, a butyl linker-containing cyclam, appeared to have most optimal sensing selectivity and afforded comparable or superior (as compared to PSVue™380) detection of negatively charged vesicles, especially at low (5 μM) vesicle concentration. The higher the $\Delta\Delta FI$, the more sensitive a sensor compound is to the type of vesicle. It is evident from the overall examination of Table 1 that PSVue™380 is overall more sensitive than compounds Ia, with one notable exception: sensors compounds I-3 and I-4 are superior to PSVue™380 at sensing PA. Sensitivity comparable to that of PSVue™380 is also observed for the detection of 5 μM PS vesicles by sensors compounds I-3 and I-4, and 20 μM CL vesicles by sensors compounds I-4 and I-5. Sensor I-4, butyl linker-containing cyclam, appeared to have most optimal sensing selectivity and afforded comparable or superior (as compared to PSVue™380) detection of negatively charged vesicles, especially at low (5 μM) vesicle concentration. Overall, cyclam-containing sensor compounds I-3 and I-4, and a methyl-linker DPA sensor compound I-5 appeared to be most optimal for the use in the detection of negatively charged vesicles.

TABLE 1

Summary of ΔΔFI of all sensor compounds for all vesicles tested

| Vesicle | 1-1 | 1-2 | 1-3 | 1-4 | 1-5 | 1-6 | PSVue™380 |
|---|---|---|---|---|---|---|---|
| 5 μM | | | | | | | |
| PE | 1 | 1.1 | 1 | 1 | 0.9 | 1 | 1.1 |
| PG | 2.6 | 2.5 | 2.4 | 3.4 | 1.7 | 1.8 | 3.9 |
| CL | 3.3 | 4.4 | 4.1 | 5.9 | 5 | 2.7 | 10.3 |
| 33% CL | 2.8 | 3 | 2.4 | 3.9 | 2.5 | 1.9 | 5.3 |
| 5% PS | 1.3 | 1.6 | 1.8 | 2.2 | 1.4 | 1.6 | 2.6 |
| 25% PS | 1.5 | 1.8 | 2.2 | 2.9 | 1.9 | 2.1 | 3.3 |
| PS | 2.6 | 2.8 | 3.5 | 4.5 | 2.9 | 2.9 | 4 |
| 75% PS | 3.3 | 4.2 | 6.5 | 7.1 | 5.4 | 4.5 | 6.1 |
| PA | 2.9 | 4.3 | 7.7 | 7.3 | 4.4 | 4.4 | 4.9 |
| 20 μM | | | | | | | |
| PE | 1 | 1.6 | 1 | 1.3 | 1 | 1 | 1.1 |
| PG | 5.4 | 5.5 | 6.2 | 7.7 | 3.9 | 2.7 | 10.2 |
| CL | 10.6 | 12 | 10.2 | 16.3 | 15.9 | 4.3 | 15.3 |
| 33% CL | 6.6 | 7.2 | 6 | 9.2 | 7.9 | 3.1 | 15.4 |
| 5% PS | 2.2 | 3.1 | 3.5 | 3.9 | 2.6 | 2.4 | 7.4 |
| 25% PS | 2.9 | 4.3 | 5.3 | 5.6 | 4 | 3 | 10.8 |
| PS | 6.6 | 7.6 | 9.8 | 10.3 | 8.8 | 4.8 | 16 |
| 75% PS | 9.4 | 11.7 | 15.6 | 16.7 | 16.7 | 7.5 | 17.4 |
| PA | 9.5 | 12.3 | 23.2 | 21.7 | 14.1 | 6.9 | 11.4 |

Since early apoptosis could potentially be detected via sensing of the PS-enriched outer membrane of a mammalian cell during early apoptosis, the sensitivity of PS detection by compounds of the Formula Ia was addressed.

Figure 7:
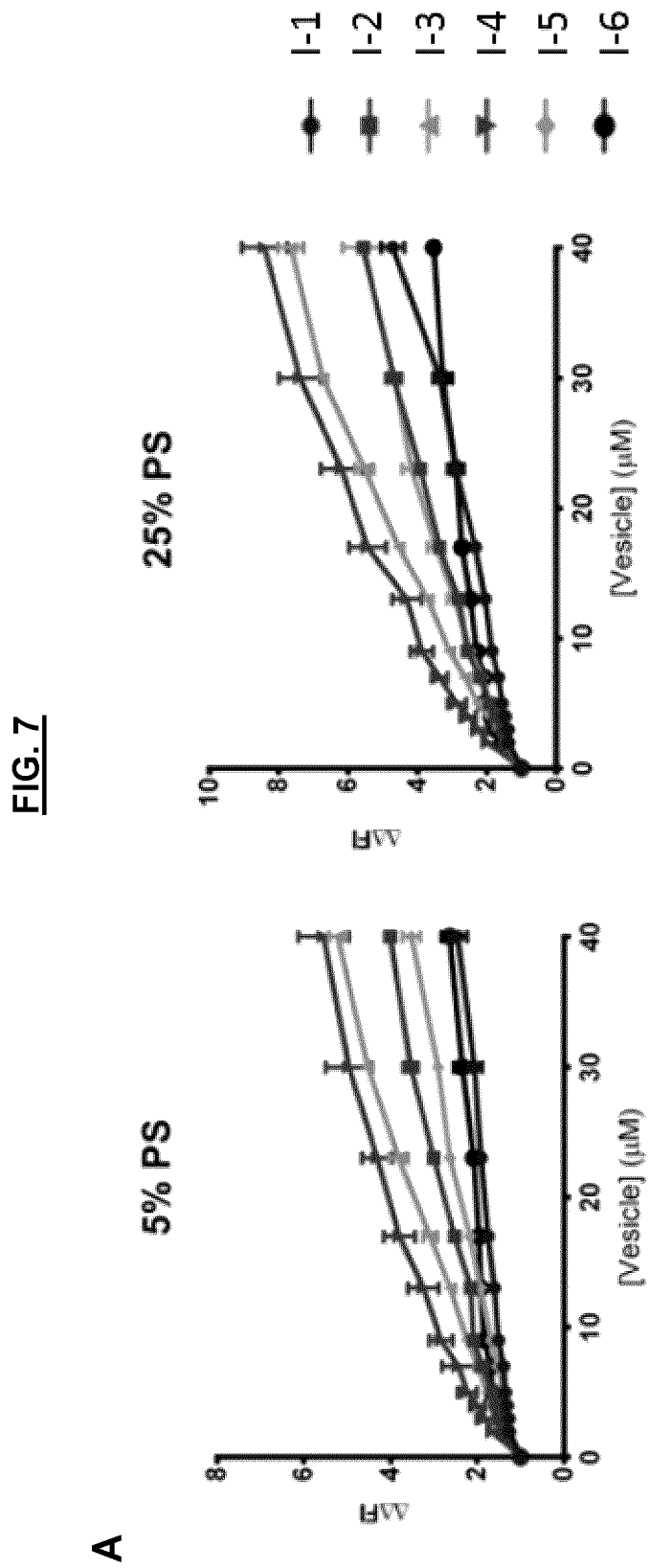
FIG. 7 shows the ΔΔFI of exemplary compounds I-1, I-2, I-3, I-4, I-5, I-6 for vesicles containing 5%, 25%, 50%, and 75% PS. Panel A shows results at vesicle concentrations from 0 to 40 μM, while panel B shows results at vesicle concentrations from 0 to 200 μM. Buffer: 50 mM HEPES, 5% DMSO, pH 7.5. [I compounds]=25 μM, $\lambda_{ex/em}$=350/476 nm.
Figure 7:
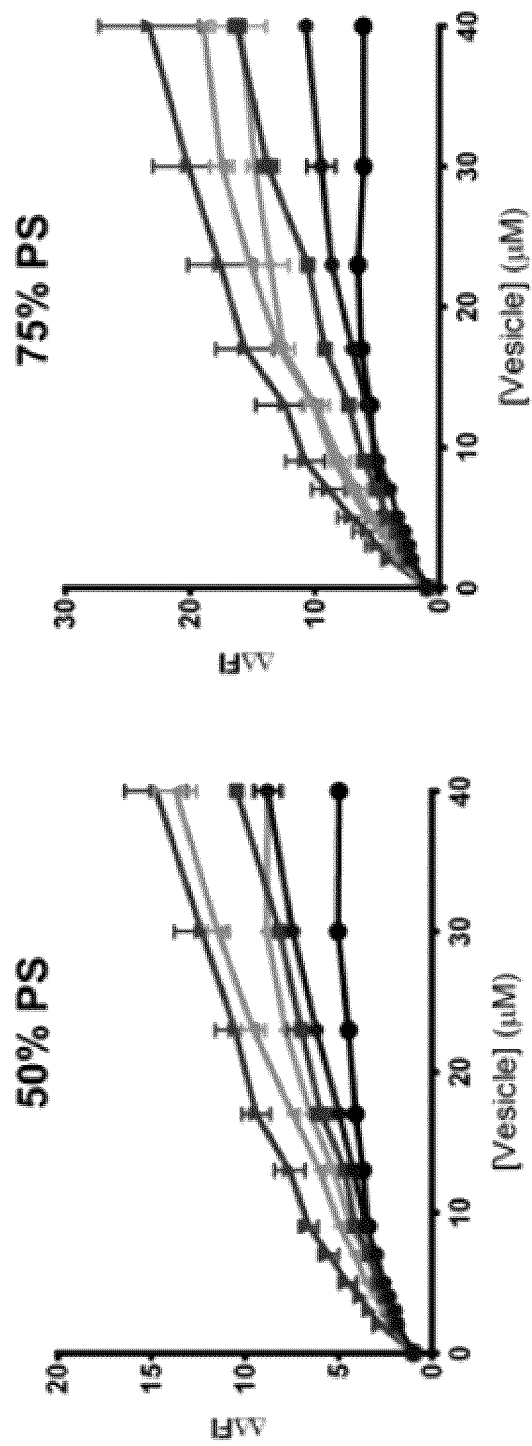
Figure 7:
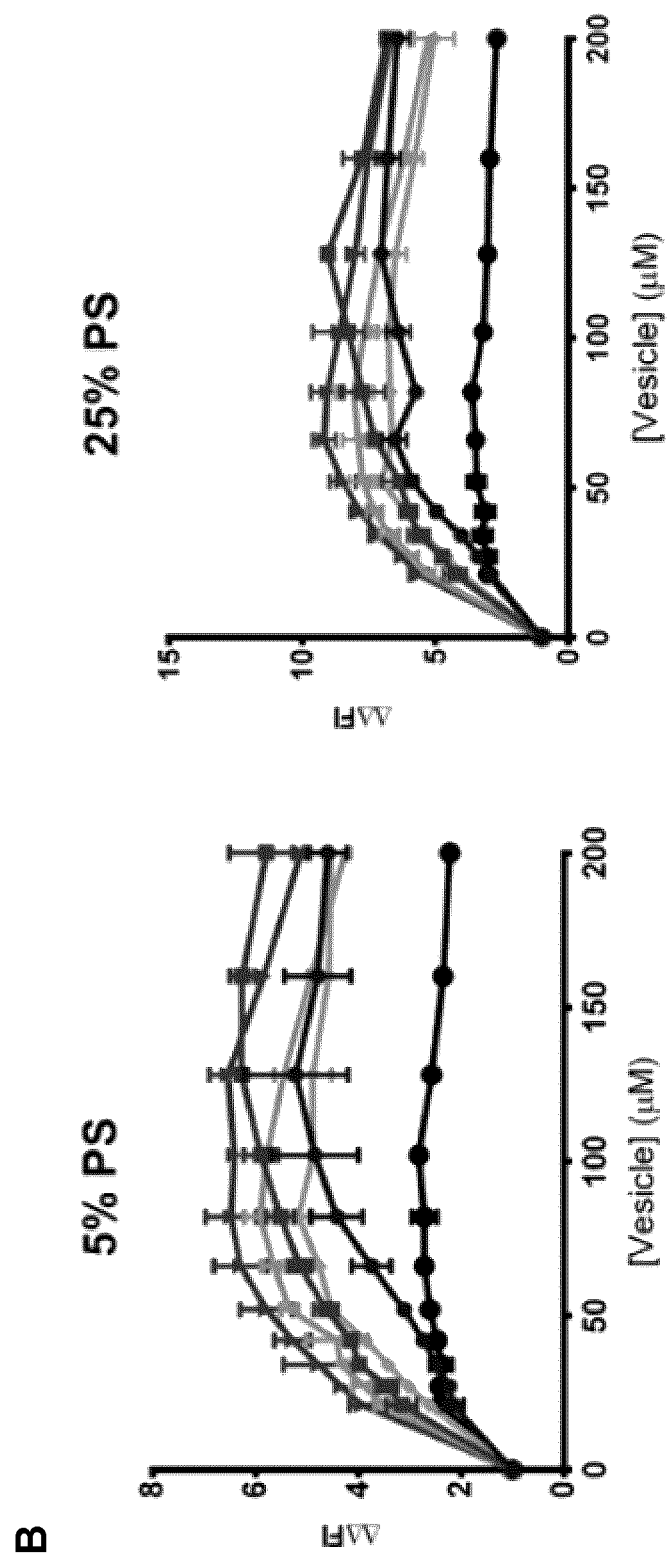
Figure 7:
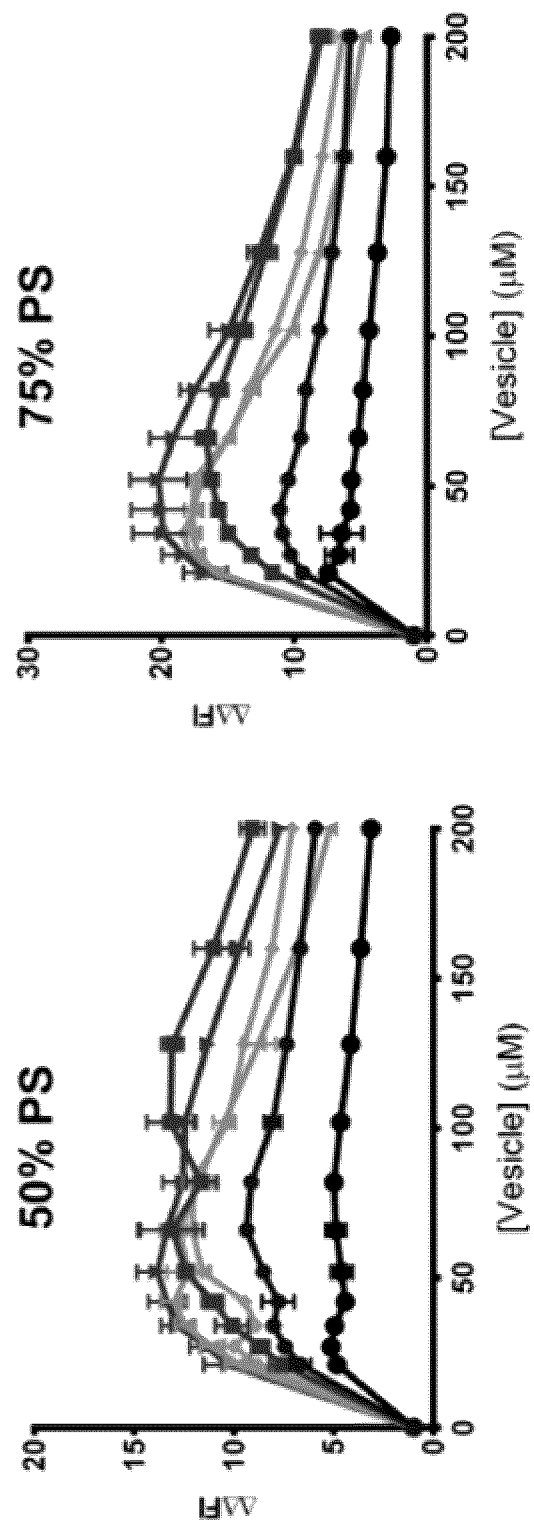

It is estimated that a mammalian cell membrane is composed of 10% PS, with the majority located on the inner leaflet in the healthy state. However, during the early stages of apoptosis, this asymmetry is lost and PS becomes symmetrically distributed resulting in ~5% of PS externalized to the outer leaflet. To address if compounds of this application could potentially be used for the detection of the PS externalization event during apoptosis, the exemplary sensors were screened against PC vesicles containing biologically-relevant levels of PS (5 and 25% PS, corresponding to 2.5 and 12.5% of PS exposed to solution; assuming that approximately half of the lipid head groups will be exposed to the interior of the vesicle). The resulting ΔΔFI for vesicle concentrations up to 40 μM are presented in FIG. 7 and Table 1 (ΔΔFI for vesicle concentrations up to 200 μM is presented in FIG. 4). It can be seen that sensor compounds I-3 and I-4 efficiently detected these PS vesicles. Additionally, as can be seen from Table 1, the signals for compounds of Formula Ia are proportional to the amount of PS present in the vesicles. Collectively, these data suggest that sensor compounds I-3 and I-4 are suitable candidates for further exploring their utility in the detection of apoptosis.

Example 42.3: Testing of Further Exemplary Sensors

Figure 8:
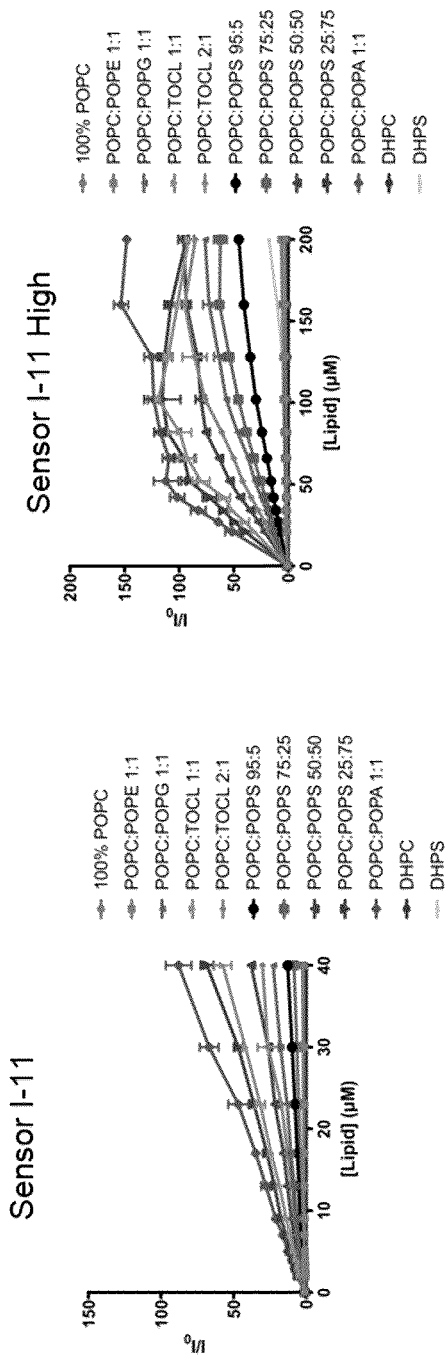
FIG. 8 shows the $\Delta FI_{exc}$ and ΔΔFI of exemplary compounds I-11, I-12 and I-9 for zwitterionic (PC, PE) and negatively charged (PA, PS, PG, CL) vesicles. Panel A shows $\Delta FI_{exc}$ of I-11 with all vesicles and short-chain lipids for vesicle concentrations from 0-40 μM (left) and 0-200 μM (right). Panel B shows ΔΔFI of I-11 with all vesicles and short-chain lipids for vesicle concentrations from 0-40 μM (left) and 0-200 μM (right). Panel C shows $\Delta FI_{exc}$ of I-12 with all vesicles and short-chain lipids for vesicle concentrations from 0-40 μM (left) and 0-200 μM (right). Panel D shows ΔΔFI of I-12 with all vesicles and short-chain lipids for vesicle concentrations from 0-40 μM (left) and 0-200 μM (right). Panel E shows $\Delta FI_{exc}$ of I-9 with all vesicles and short-chain lipids for vesicle concentrations from 0-40 μM (left) and 0-200 μM (right). Panel F shows ΔΔFI of I-9 with all vesicles and short-chain lipids for vesicle concentrations from 0-40 μM (left) and 0-200 μM (right). Buffer: 50 mM HEPES, 5% DMSO, pH 7.5. [Ia compounds]=25 μM, $\lambda_{ex/em}$=350/476 nm. ($\Delta FI_{exc}=FI_{exc\ vesicle}/FI_{exc\ buffer}$)
Figure 8:
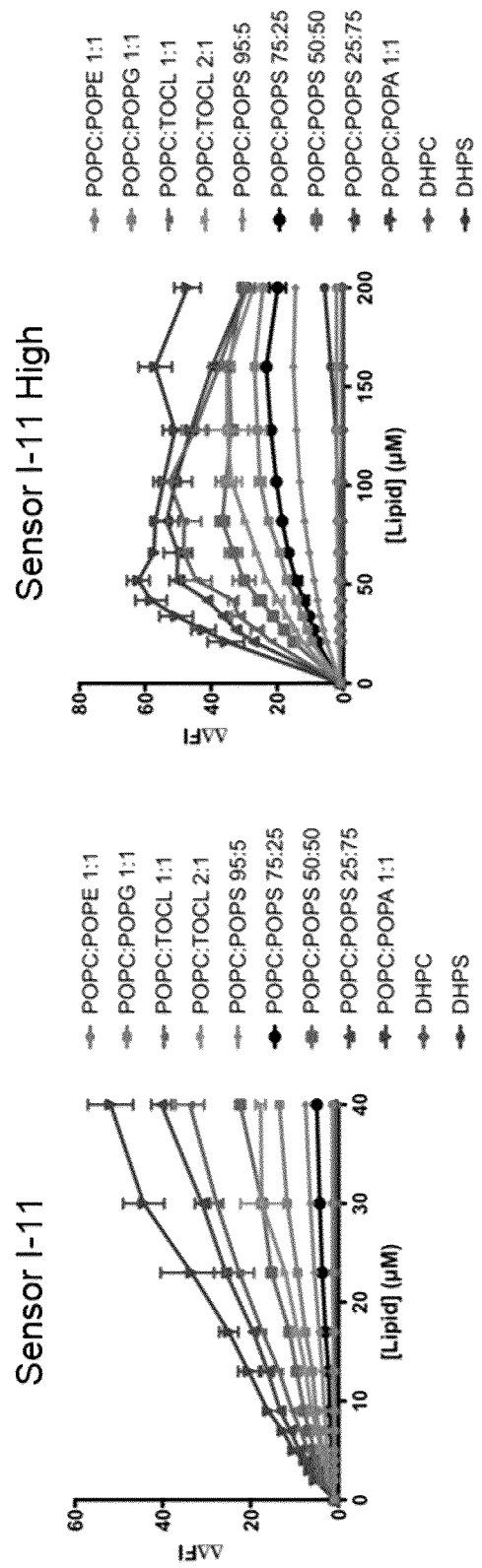
Figure 8:
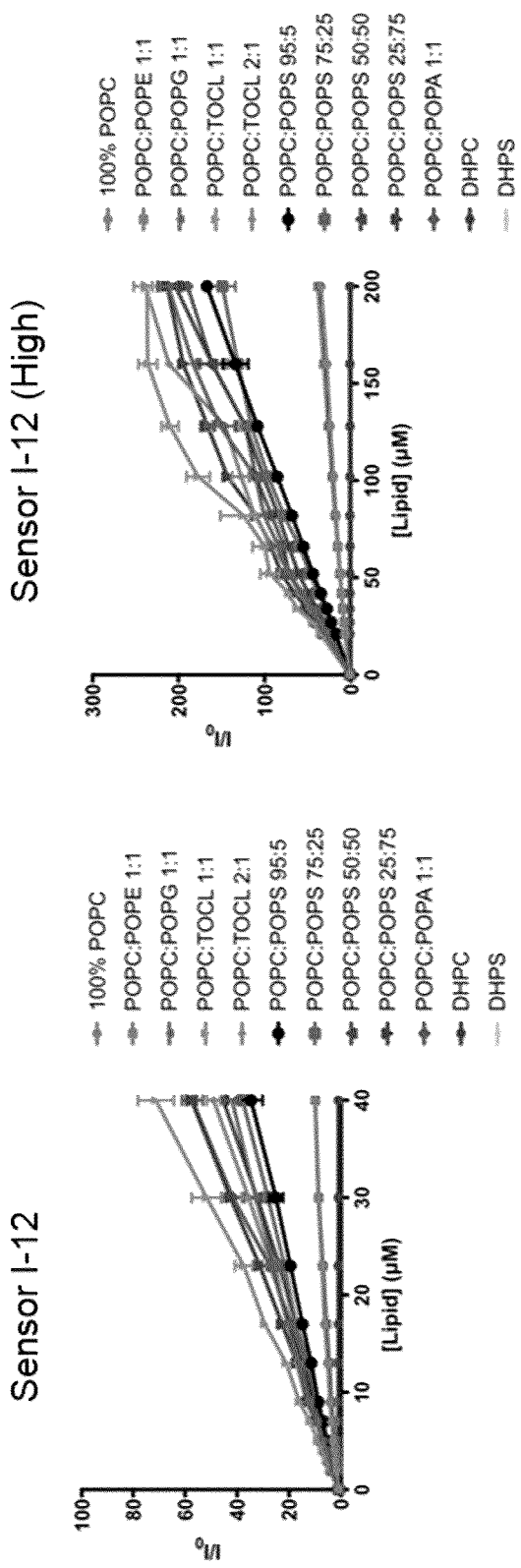
Figure 8:
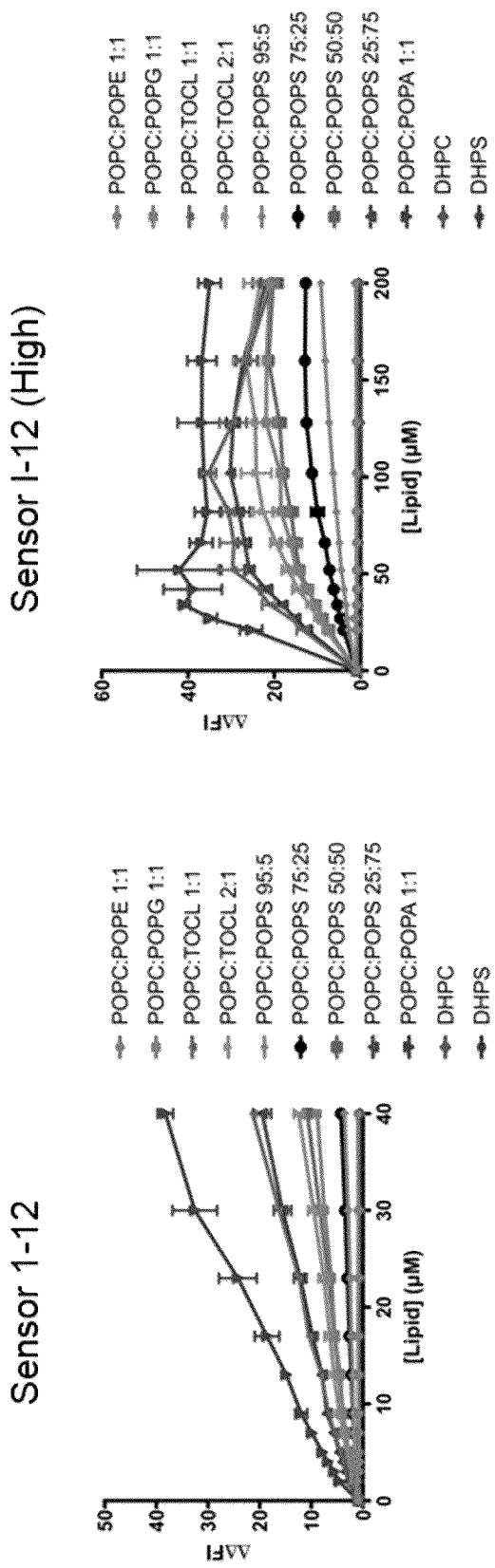
Figure 8:
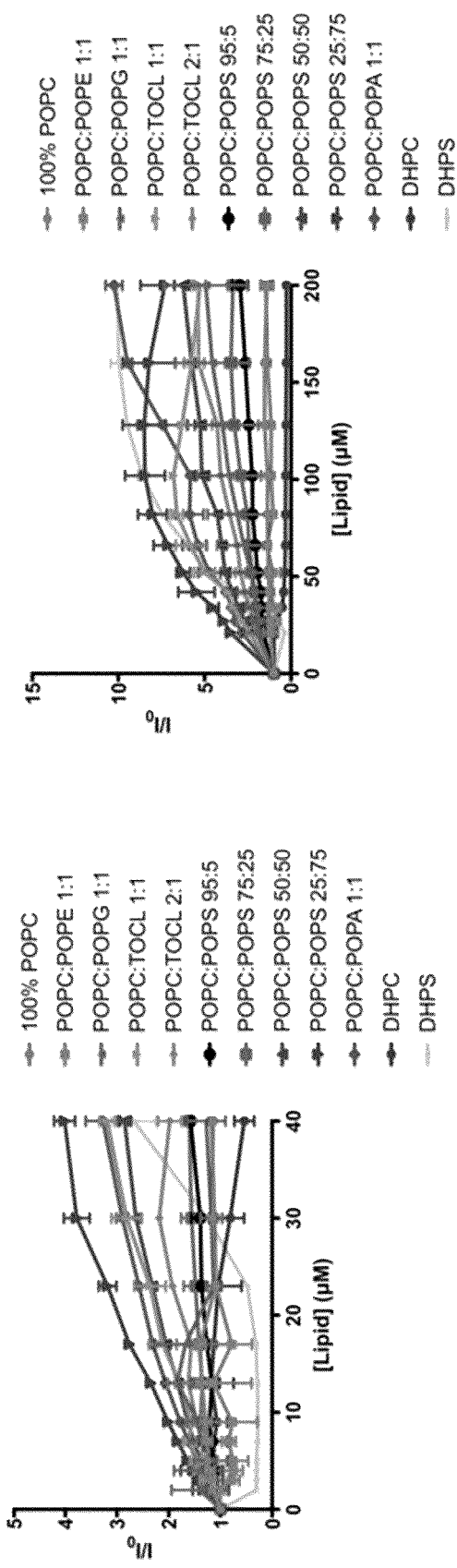
Figure 8:
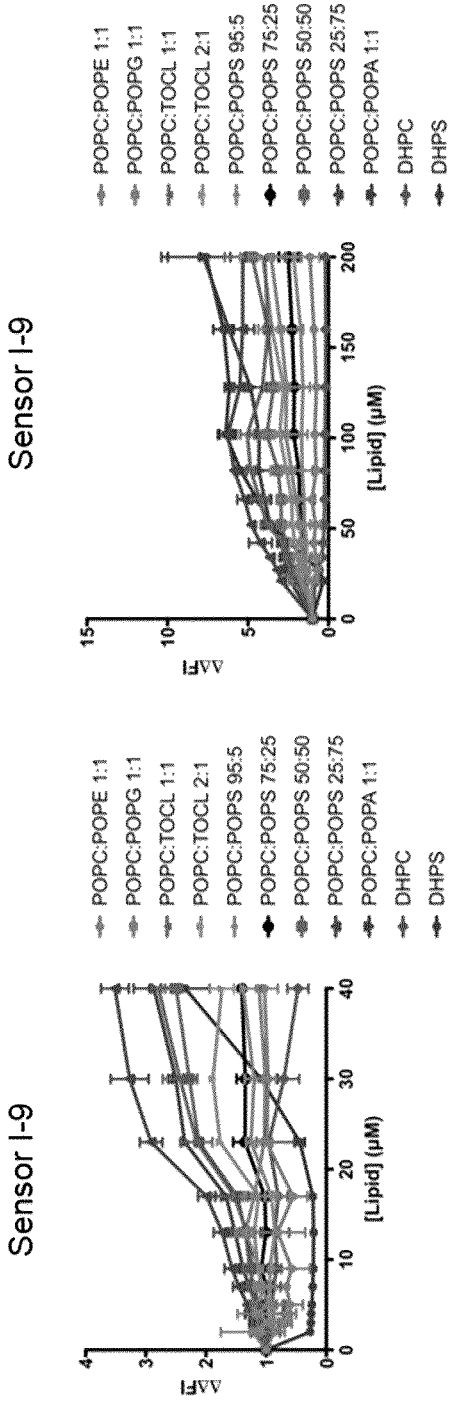

FIG. 8 shows the $\Delta FI_{exc}$ and $\Delta\Delta FI_{exc/mon}$ for compounds I-11, I-12 and I-9 with all vesicles (zwitterionic PC and PE and negatively charged PA, PG, CL and PS) and short-chain lipid controls (DHPC & DHPS). As evident in FIG. 8A, sensor compound I-11 selectively detected all negatively charged vesicles, with $\Delta FI_{exc}$~50 and above (up to ~150) over zwitterionic ones ($\Delta FI_{exc}$≤3). As evident in FIG. 8C, sensor compound I-12 selectively detected all negatively charged vesicles, with $\Delta FI_{exc}$~20 and above (up to ~80) over zwitterionic ones ($\Delta FI_{exc}$≤2). As evident in FIG. 8E, sensor compound I-9 detected the negatively charged vesicles with $\Delta FI_{exc}$~3 and above (up to ~10). However, the $\Delta FI_{exc}$ for zwitterionic vesicles was around 1, indicating that the enhancement in signal for the negatively charged vesicles as compared to the zwitterionic vesicles was low evident by the low $\Delta\Delta FI_{exc/mon}$ values as observed in FIG. 8F. Thus, sensor compound I-9 was concluded to be sub-optimal for the detection of negatively charged phospholipids.

Example 42.4: Phosphoserine Competition Experiments

Figure 9:
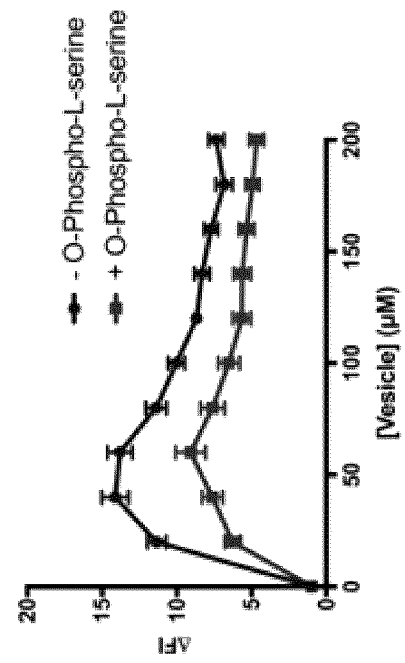
FIG. 9 shows ΔFI of exemplary sensor compound I-1 (25 μM) upon addition of PS vesicles, in the absence or presence of O-Phospho-L-serine. Panel A shows ΔFI where O-Phospho-L-serine was added before vesicle addition. Panel B shows ΔFI where O-Phospho-L-serine was added after vesicle addition. Buffer: 50 mM HEPES, 5% DMSO, pH 7.5. [Ia-1]=25 μM, $\lambda_{ex/em}$=350/476 nm.
Figure 9:
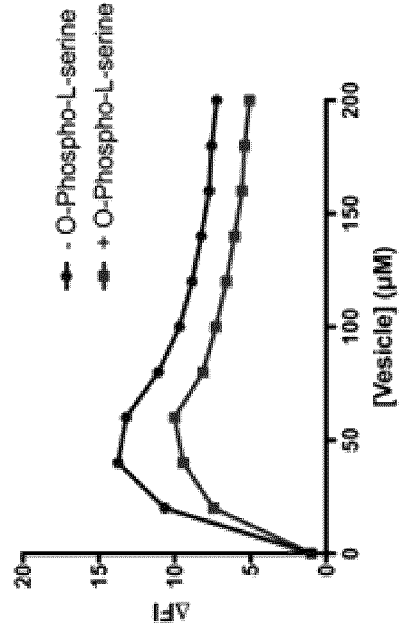

To probe whether the sensors were directly binding to the negatively charged phospholipid head groups, phosphoserine competition experiments were performed with sensor compound I-1. Briefly, it was hypothesized that if the sensing mechanism necessitates direct binding of the sensor to the phospholipid head groups, phosphoserine added to the sensor-vesicle solution would compete for binding to the sensor (yet not induce an excimer signal as demonstrated in FIG. 9), which would lead to a decrease of the excimer signal. Vesicle fluorescence intensity experiments were performed in the absence or presence of phosphoserine, where phosphoserine was added to sensor either before or after combining with vesicles.

PS vesicles were prepared from stock solutions from 400-40 μM in 20 μM intervals in pH 7.5, 50 mM HEPES. Phosphoserine Absent: PS vesicles were combined in equal volumes with 50 μM of sensor 1 (compound I-1) in pH 7.5, 50 mm HEPES, 10% DMSO and incubated for 10 min away from light, and the fluorescence intensity at 476 nm was measured after excitation at 350 nm. Phosphoserine Addition Before: A second trial was similarly performed, except sensor compound I-1 was pre-incubated with O-Phospho-L-serine (4:1 phosphoserine:sensor) for 5 min, and was then combined with PS vesicles, followed by fluorescence intensity measurements. Phosphoserine Addition After: A third trial was also performed where sensor and PS vesicles were combined as described previously, and the fluorescence intensity was measured. Following this, O-Phospho-L-serine was added (4:1 Phosphoserine:sensor) and fluorescence intensity was again measured.

In both experimental setups, the excimer signal was decreased compared to control in the presence of phosphoserine (shown in FIG. 9), supporting sensors' direct interaction with negatively charged phospholipid head groups.

Example 42.5 Zinc Metalation Fluorescence Experiments

To ascertain whether the sensing mechanism is metal-dependent, selected experiments from Example 1.1 were repeated against all vesicles using compounds III-1, II-4 and II-5, corresponding to the unmetallated counterparts of compounds I-1, I-4 and I-5 respectively. Vesicle fluorescence intensity experiments were performed in the absence or presence of zinc(II) (trifluoromethanesulfonate salt). Unmetallated PSVue™380 (PSVue™380*) was also included for reference.

All glassware was treated with 0.1 M HCl overnight, rinsed three times with MilliQ water, and oven dried. Absence of Zinc: the same procedure described for the serial dilution vesicle fluorescence intensity experiments was performed with compounds I-1, I-4, and I-5, along with their unmetallated counterparts (compounds II-1, II-4, and II-5), where sensors were combined with PA vesicles. Presence of Zinc: A second procedure with the unmetallated sensor compounds II-1, II-4 and II-5 was performed where zinc (II) trifluoromethanesulfonate was added (1 equivalent). The sensor-zinc solutions were then combined with PA vesicles, prepared as described above, incubated as described above and the fluorescence emission intensity was then measured as described above.

Figure 10:
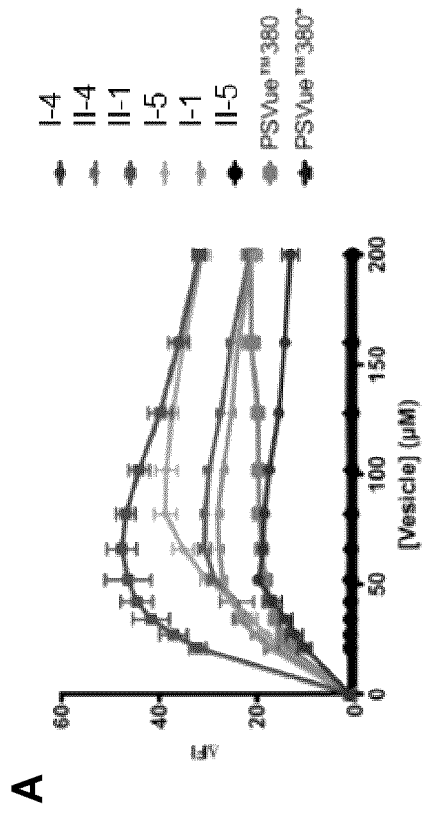
FIG. 10 shows the ΔFI and FI of exemplary metallated I and unmetallated II compounds upon addition of PA vesicles from 0 to 200 μM. Panel A shows ΔFI of exemplary compounds I-4, II-4, II-1, I-5, I-1, II-5, PSVue™380 and unmetallated PSVue™380* with PA vesicles. Panel B shows FI for exemplary compounds I-4, II-4, II-1, I-5, I-1, II-5, PSVue™380 and unmetallated PSVue™380 with PA vesicles, where metallated compounds I-4, I-5, and I-1 were prepared either as lyophilized powders (denoted as "metallated" in the figure) or a compound of formula II were combined with a solution containing equimolar amount (except for PSVue™380, which was combined with 2 equivalent) of metals salt (denoted as "in-situ metalation").
Figure 10:
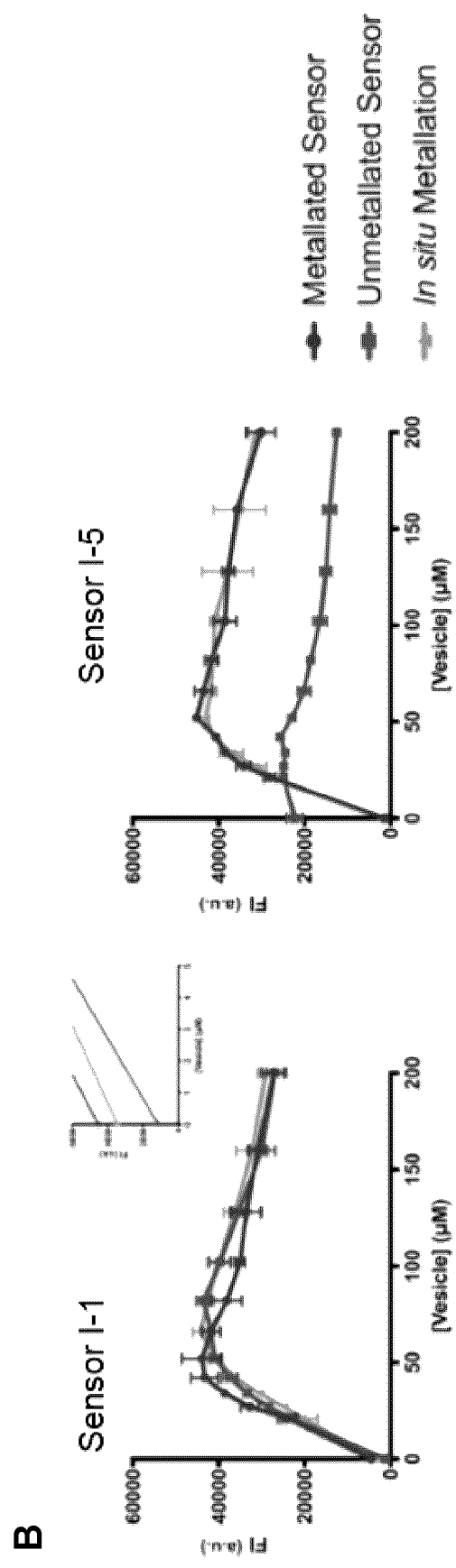
Figure 10:
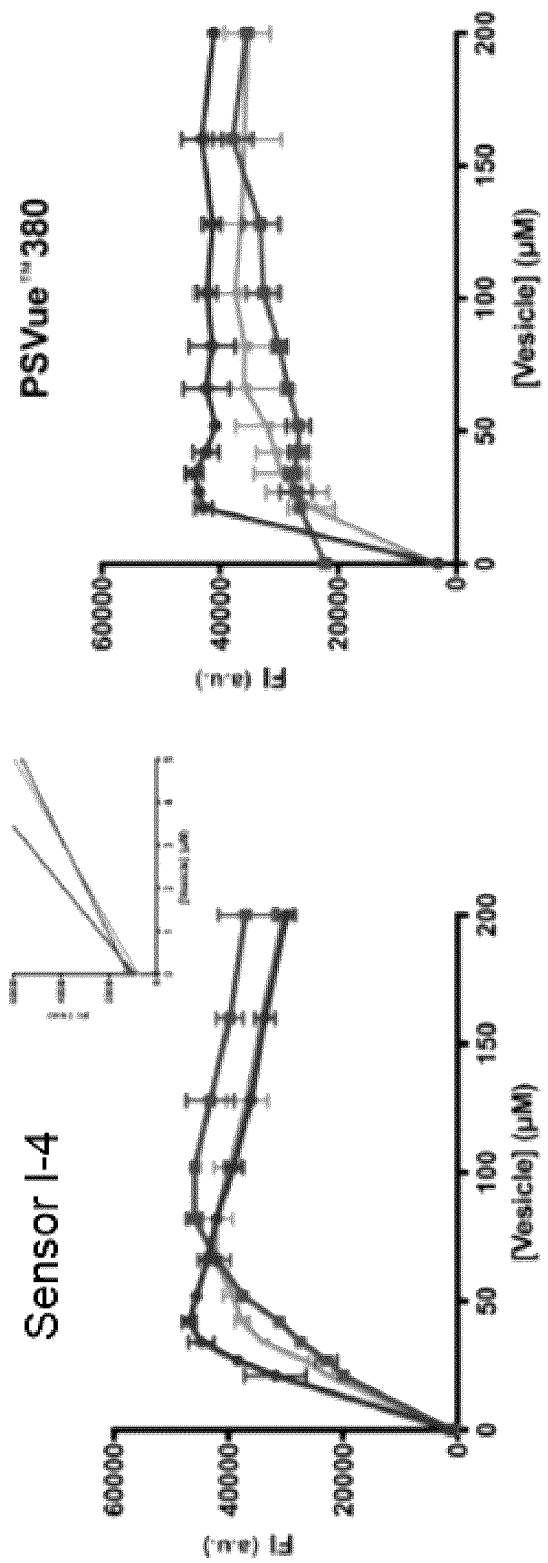

FIG. 10A shows the ΔFI of exemplary metallated compounds I, unmetallated compounds II, and metallated and unmetallated PSVue™380 at various vesicle concentrations. As the proposed sensing mechanism relies on the coordinative interaction between the chelated $Zn^{2+}$ and the negatively charged phospholipid head group (FIG. 1), it was expected that unmetallated sensors would not bind, and therefore, not detect the negatively charged vesicles. Representative results with PA vesicles are shown in FIG. 10. As expected, compound II-5 (and PSVue™380*) lost their ability to sense PA in the absence of $Zn^{2+}$. The unmetallated cyclen and cyclam sensors compound II-1 and II-4 not only retained their ability to detect PA in the absence of $Zn^{2+}$, but sensor compound II-1 also outperformed its metallated counterpart.

The ability of cyclen and cyclam, but not DPA sensors, to detect negatively charged vesicles in both, metallated and unmetallated sensor states warranted further investigation. In order to rule out the possibility that this result was an artifact of unmetallated cyclen and cyclam sensors undergoing in situ metalation with trace metal present in the buffers or plastics, whereas DPA, owing to its lower affinity to $Zn^{2+}$ (DPA Kd=70 nM in 0.1 M $KNO_3$, Cyclen Kd=0.63 fM in 0.1 M $NaNO_3$, Cyclam Kd=3.2 fM 0.5 M $KNO_3$; all at 25° C.), may fail to form metal complexes in situ. Although it was unlikely that trace metal could fully recover and further improve the sensing ability of sensors. In an effort to eliminate this possibility, all glassware was acid-treated and all buffers were chelex-treated to remove any metals, and the screens were repeated with PA vesicles. For these experiments, original non-normalized $FI_{exc}$ values were analyzed. As can be seen from FIG. 10B, unmetallated (square) and metallated (circle) sensors II-1 and II-4 showed comparable responses to increasing PA vesicle concentrations. The difference originally observed in ΔFI between the unmetallated (II-1) and metallated sensor 1 (I-1) in fact originated from the difference in their background sensor signal which was used to normalize the FI values in the ΔFI calculation (FIG. 10B, Inset). On the other hand, unmetallated DPA sensor II-5 and PSVue™380* did not respond to the increasing concentrations of PA vesicles (FIG. 10B, flat line with square markers). To eliminate the possibility that DPA sensors could not undergo in situ metalation with trace metal, equimolar amount of $Zn^{2+}$ (25 μM, trifluoromethanesulfonate salt) was added exogenously to all sensor-vesicle solutions. As expected, both DPA sensors' signal was restored to the levels of metallated sensors (FIG. 10B, triangle). Collectively, this data suggested that the sensing ability of unmetallated cyclen and cyclam sensors II-1 and II-5 was likely not an artifact of in situ metalation with trace metal. It is proposed that cyclen and cyclam sensors could potentially operate by both, a metal-independent and metal-dependent mechanisms, where in the former, cyclen and cyclam chelates are found in their doubly protonated states (cyclen pKa's=10.97, 8.97; cyclam pKa's=11.29, 10.19) and interact with the negatively charged phospholipid head group via electrostatic and hydrogen-bonding interactions. Consistent with this hypothesis is the lower potential of protonation in unmetallated DPA sensors (pKa's=7.30, 2.60, 1.12), which translates into their inability for forming significant electrostatic and hydrogen-bonding interactions with PA head groups. It is unlikely that cyclen and cyclam sensors operate in a chelate-independent mechanism, as consistent selectivity for negatively charged vesicles was demonstrated.

Example 43: Bacterial Detection

General

*E. coli* K-12 BW25113 cells were grown overnight in M9 minimal media and then harvested the following morning. Cells were then washed (spun at 5000 rpm for 10 min/wash) three times in buffer (50 mM HEPES, 75 mM NaCl, 1% BSA, 0.4% DMSO, pH 7.5). Cell concentrations were then determined using OD600 and cell samples were diluted to the appropriate concentrations. Fluorescence microscopy experiments were performed with an Olympus IX81 Inverted TIRF microscope with an X-Cite® 120Q excitation light source using maximum power. For all experiments, the excitation filter was 325/50 nm, the emission filter was 447/60 nm and exposure time was set to 30.28 ms.

Figure 11:
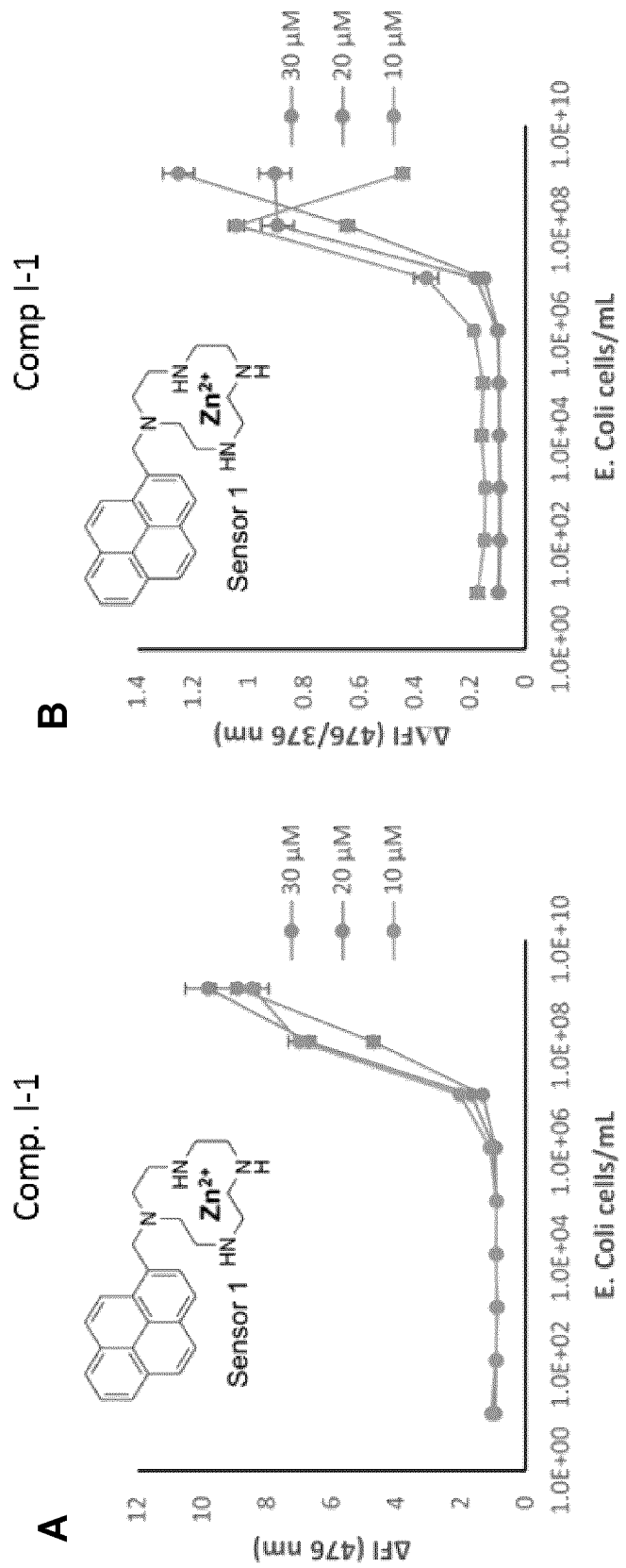
FIG. 11 shows a proof-of-concept *E. coli* titration. Panel A shows ΔFI and Panel B shows ΔΔFI of exemplary compound I-1 (10 μM) in response to increasing amounts of *E. coli* K-12 BW25113 cells/mL. Buffer: 50 mM HEPES, pH 7.5, 75 mM NaCl, 0.4% DMSO, $\lambda_{ex/em}$=350/476 nm.

FIG. 11 shows a proof-of-concept *E. coli* titration panel A shows ΔFI and panel B shows ΔΔFI of compound I-1 (10 μM) in response to increasing amounts of *E. coli* K-12 BW25113 cells/mL (50 mM HEPES, 75 mM NaCl, 1% BSA, 0.4% DMSO, pH 7.5). Results clearly indicate that compound I-1 is capable of sensing increasing amounts of bacteria.

Example 43.1 Fluorescence Microscopy Experiments with Bacteria

Coverslips were coated in Poly-L-Lysine (0.1 mg/mL) overnight. Bacteria samples were added onto the Poly-L-Lysine coated coverslip and left to stick for 5 minutes. The bacteria were first visualized in bright field and then autofluorescence was recorded with UV excitation. Sensors were added on top of the bacteria at appropriate concentrations and fluorescence emission was captured.

Figure 12:
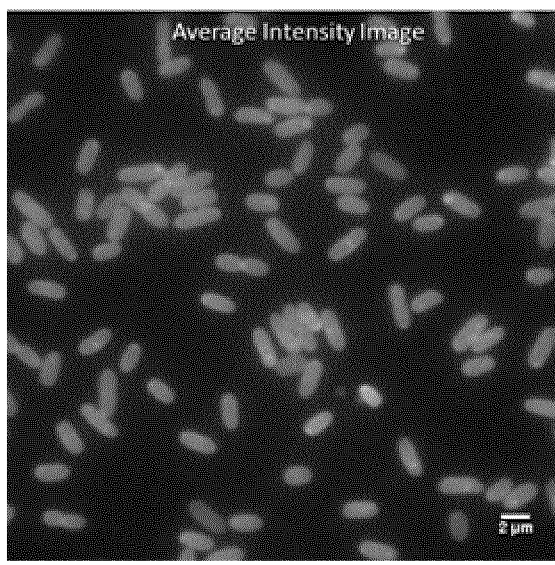
FIG. 12 shows *E. coli* K-12 BW25113 cells ($10^8$ cells/mL; 25 mM HEPES, pH 7.0, 0.4% DMSO; excitation=325/50 nm, emission=447/60 nm, exposure time=30.28 ms) detection using fluorescence microscopy. Panel A shows the average intensity image with exemplary compound I-5. Panel B shows the SRRF intensity image with exemplary compound I-5. Panel C shows the UV image with exemplary sensor compound I-1. Panel D shows the UV image with exemplary compound Ia-6 (30 μM). Panel E shows UV image with exemplary compound I-5 (10 μM). Panel F shows a petri dish control containing buffer or petri dish with *E. coli* where exemplary compound Ia-1 (40 μM) was added and the plate excited with long wave UV lamp.
Figure 12:
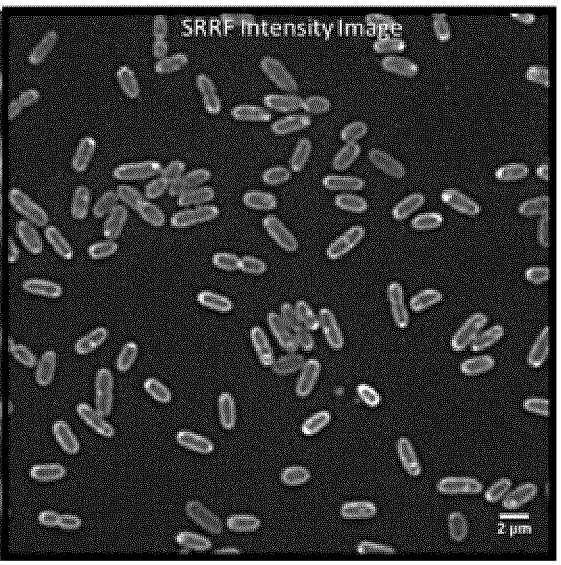
Figure 12:
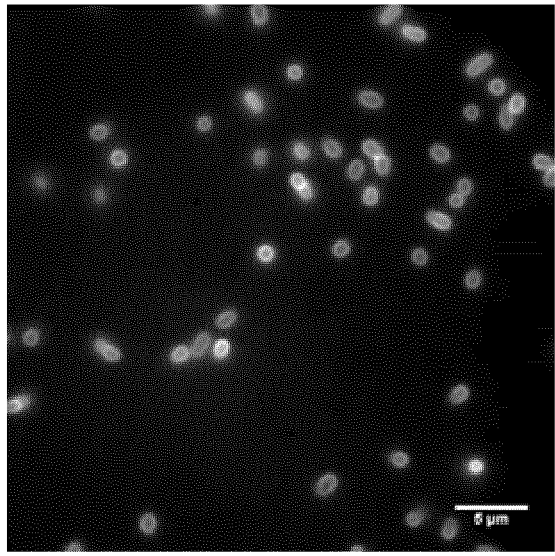
Figure 12:
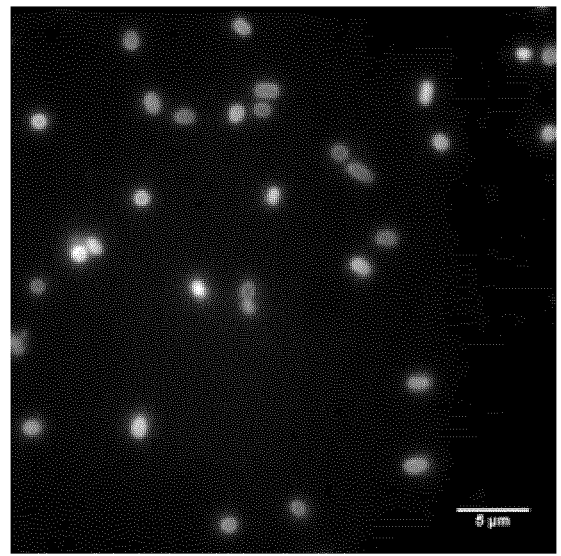
Figure 12:
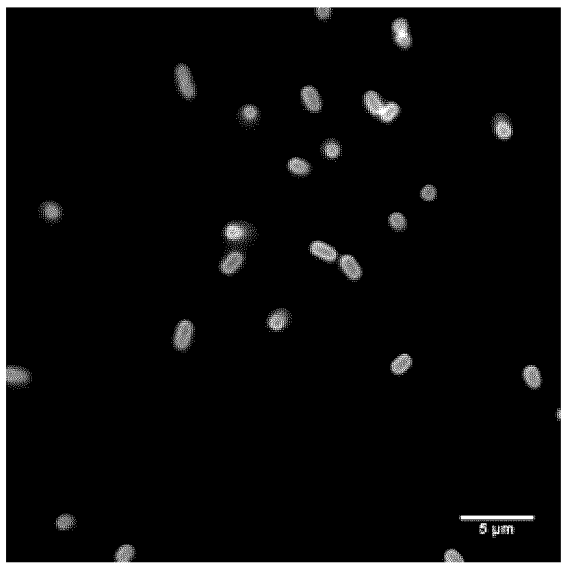
Figure 12:
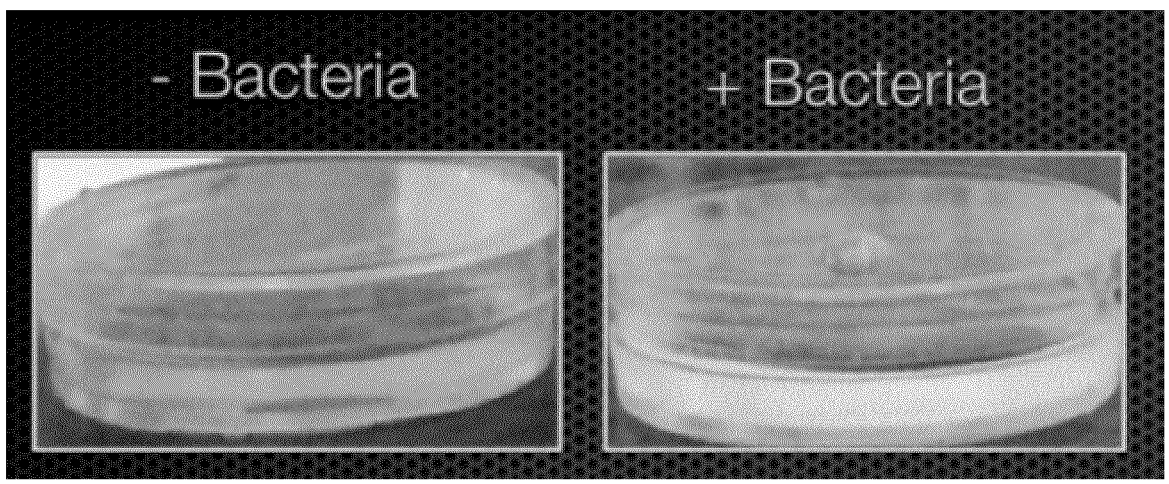

FIG. 12 shows Gram-negative bacteria *E. coli* K-12 BW25113 cells ($10^8$ cells/mL; 25 mM HEPES, pH 7.0, 0.4% DMSO; excitation=325/50 nm, emission=447/60 nm, exposure time=30.28 ms) detection using fluorescence microscopy. Panel A shows the average intensity image with compound I-5. Panel B shows the SRRF intensity image with compound I-5. Panel C shows the average intensity image with sensor compound I-1. Panel D shows the average intensity image with compound I-6 (30 μM). Panel E shows the average intensity image with compound I-5 (10 μM). Panel F shows a petri dish control with buffer or petri dish with *E. coli* where compound I-1 (40 μM) was added and the plate excited with long wave UV lamp.

Figure 13:
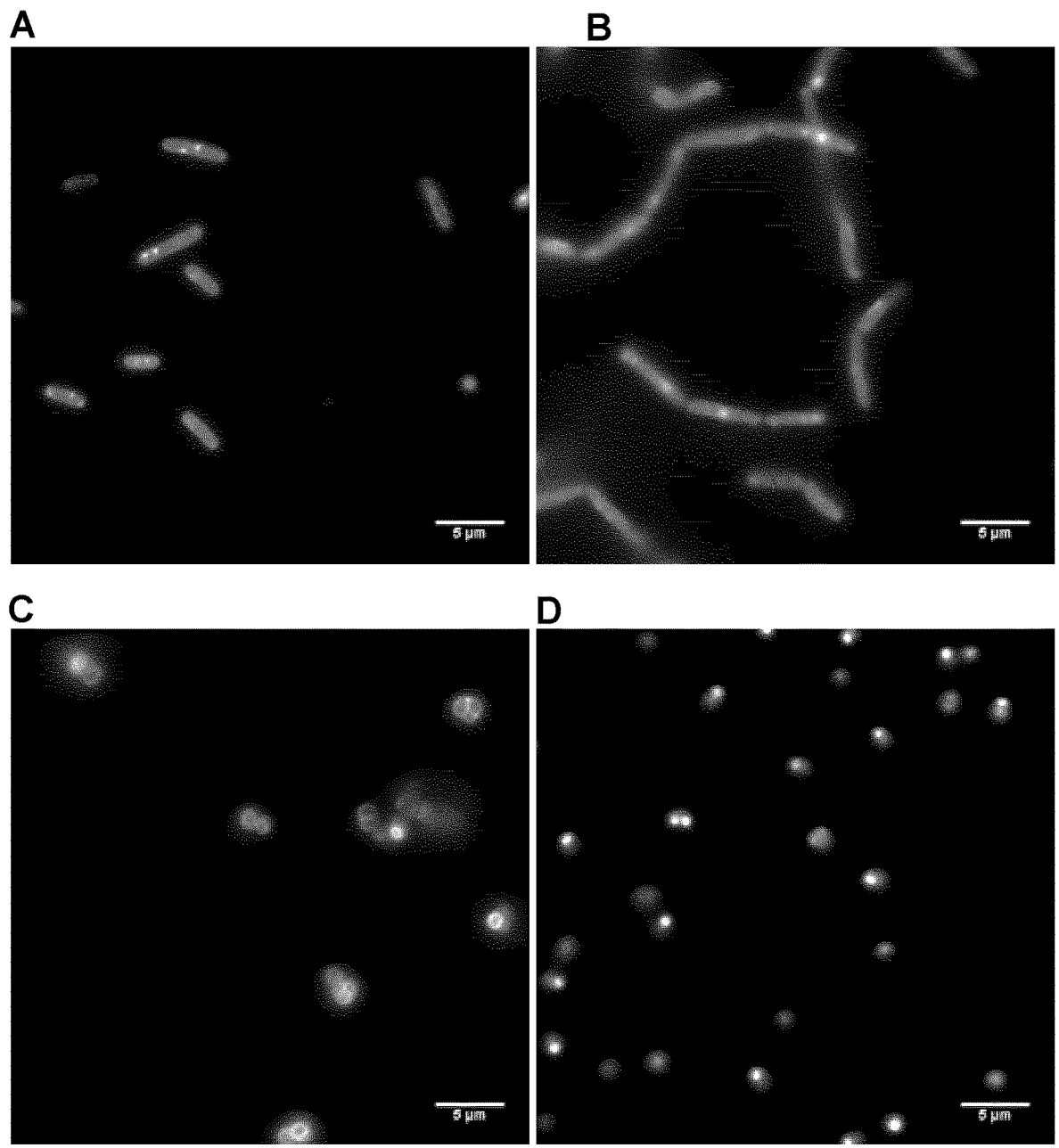
FIG. 13 shows Gram-positive bacteria *B. subtilis* (panel A), *B. megaterium* (panel B), *M. luteus* (panel C), and *S. epidermidis* (panel D) detection using fluorescence microscopy with exemplary compound I-4 (10 μM sensor compound, $10^8$ cells/mL; 50 mM HEPES, pH 7.5, 75 mM NaCl, 0.4% DMSO; excitation=325/50 nm, emission=447/60 nm, exposure time=30.28 ms).

FIG. 13 shows Gram-positive bacteria *B. subtilis* (panel A), *B. megaterium* (panel B), *M. luteus* (panel C), and *S. epidermidis* (panel D) detection using fluorescence microscopy with compound I-4 (10 μM sensor compound, $10^8$ cells/mL; 50 mM HEPES, pH 7.5, 75 mM NaCl, 0.4% DMSO; excitation=325/50 nm, emission=447/60 nm, exposure time=30.28 ms).

The results demonstrate that exemplary sensor compounds I are capable of detecting both Gram-positive and Gram-negative bacteria.

Example 43.2 Fluorescence Microscopy Experiments with Bacteria and Mammalian Cells MV4-11 mammalian cells and bacteria samples were both added to a microscope chamber slide and left to incubate for 5 minutes. Visualization was performed first in bright field and then auto-fluorescence was recorded with UV excitation. Sensors were then added into the chamber at appropriate concentrations and fluorescence emission was captured.

Figure 14:
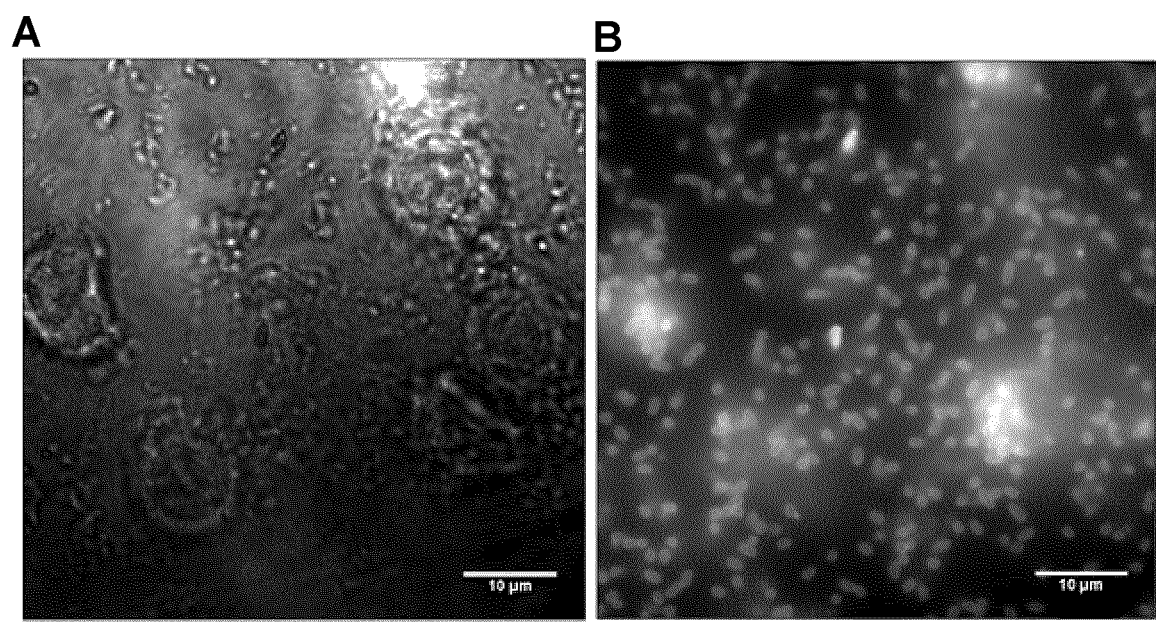
FIG. 14 shows *E. coli* K-12 BW25113 cells ($10^8$ cells/mL; 25 mM HEPES, pH 7.0, 0.4% DMSO; excitation=325/50 nm, emission=447/60 nm, exposure time=30.28 ms) detection using fluorescence microscopy with exemplary compound I-5 in presence of MV4-11 cells. Panel A shows the bright-field image. Panel B shows the UV image. [I-5]=40 μM.

FIG. 14 shows *E. coli* K-12 BW25113 cells ($10^8$ cells/mL; 25 mM HEPES, pH 7.0, 0.4% DMSO; excitation=325/50 nm, emission=447/60 nm, exposure time=30.28 ms) detection using fluorescence microscopy with compound I-5 in presence of MV4-11 cells. Panel A shows the bright-field image. Panel B shows the UV image. These results suggest that bacterial cells are detected more readily than mammalian MV4-11 cells.

Example 43.3 Fluorescence Titrations with Bacteria

Bacteria samples were titrated from $10^8$-$10^{10}$ cells/mL in a large-volume 12 well plate. Bacteria samples were added to black 384-well plates in triplicate. Sensors ([Final]=10 µM; 50 mM HEPES, pH 7.5, 75 mM NaCl, 0.4% DMSO) were added to each bacteria sample, and were incubated for 10 minutes prior to reading fluorescence intensity ($\lambda_{ex/em}$=350/476 nm, excitation bandwidth=5 nm, emission bandwidth=10 nm).

Figure 15:
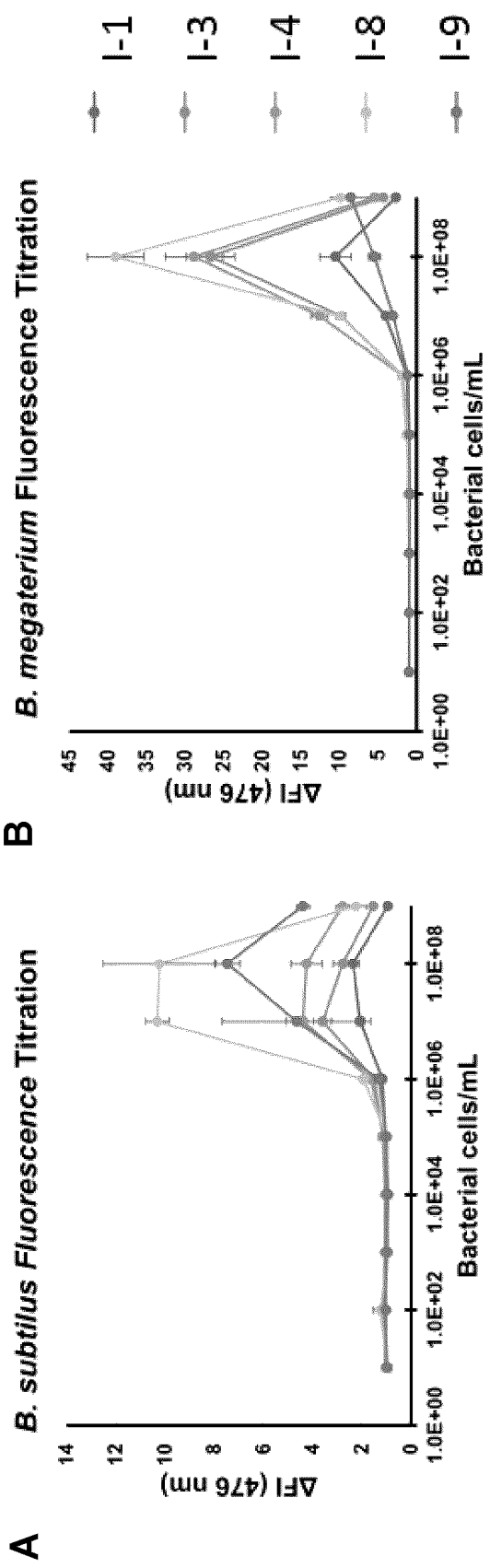
FIG. 15 shows the titration curves for *B. subtilis* (A), *B. megaterium* (B), *M. luteus* (C), *S. epidermidis* (D) (50 mM HEPES, pH 7.5, 75 mM NaCl, 0.4-2.5% DMSO) for exemplary compounds I-1, I-3, I-4, I-8 and I-9. [I compounds]=10 μM, $\lambda_{ex/em}$=350/476 nm.
Figure 15:
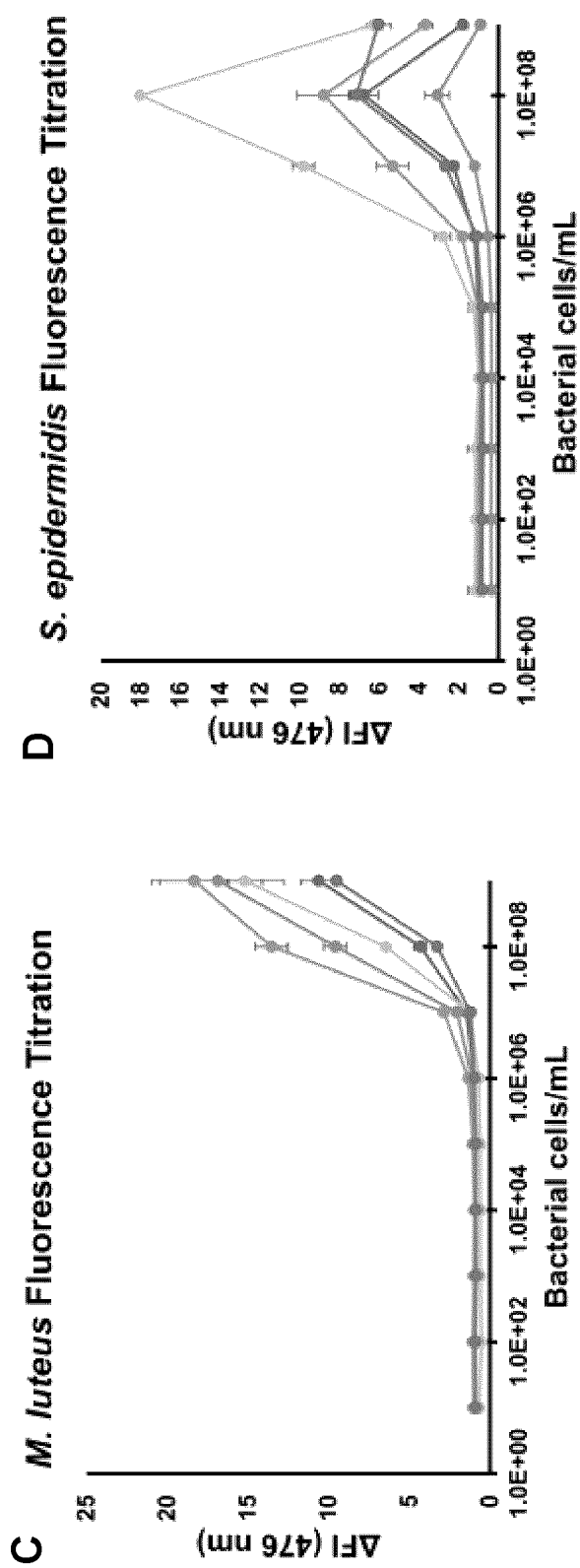

A proof-of-concept titration experiment was performed with compounds I-1, I-3, I-4, I-8 and I-9. FIG. 15 shows the titration curves for *B. subtilis* (A), *B. megaterium* (B), *M. luteus* (C), *S. epidermidis* (D) (50 mM HEPES, pH 7.5, 75 mM NaCl, 0.4-2.5% DMSO). The results suggest that these sensors can detect Gram-positive bacteria using a fluorometer in a bulk solution without bacterial immobilization.

Example 43.4 Bacteria Flow Cytometry Experiments

Bacteria samples (500 µL) were treated with 40 uM sensor (POC Sensor compound Ia-1 & Long Cyclam Sensor compound I-6). Samples were run at the Flow Cytometry Facility, Medical Sciences Building, University of Toronto, on a BD LSR Fortessa X20 using the UV laser (emission: 450/50 nm) with low flow rate (15 uL sample/min) for 2 min.

Figure 16:
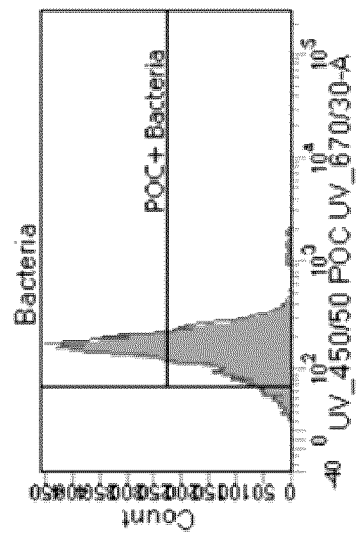
FIG. 16 shows bacteria flow cytometry results. Panel A shows *E. coli* K-12 BW25113 cells ($10^7$ CFU/mL) treated with 40 μM POC sensor (exemplary sensor compound I-1). Sample run using UV laser (BD LSR Fortessa X20, emission: 450/50 nm) in 50 mM HEPES, 75 mM NaCl, 1% BSA, 0.4% DMSO, pH 7.5. Panel B shows *E. coli* K-12 BW25113 cells ($10^8$ CFU/mL) treated with 40 μM POC sensor (exemplary sensor compound I-1). Sample run using UV laser (BD LSR Fortessa X20, emission: 450/50 nm) in 50 mM HEPES, 75 mM NaCl, 1% BSA, 0.4% DMSO, pH 7.5. Panel C shows *E. coli* K-12 BW25113 cells ($10^8$ CFU/mL) treated with 40 μM Long Cyclam (exemplary sensor compound I-4) sensor. Sample run using UV laser (BD LSR Fortessa X20, emission: 450/50 nm) in 50 mM HEPES, 75 mM NaCl, 1% BSA, 0.4% DMSO, pH 7.5. Panel D shows 40 μM POC sensor (exemplary sensor compound I-1) without bacteria. Sample run using UV laser (BD LSR Fortessa X20, emission: 450/50 nm) in 50 mM HEPES, 75 mM NaCl, 1% BSA, 0.4% DMSO, pH 7.5. Panel E shows 40 μM Long Cyclam (exemplary sensor compound I-4) without bacteria. Sample run using UV laser (BD LSR Fortessa X20, emission: 450/50 nm) in 50 mM HEPES, 75 mM NaCl, 1% BSA, 0.4% DMSO, pH 7.5.
Figure 16:
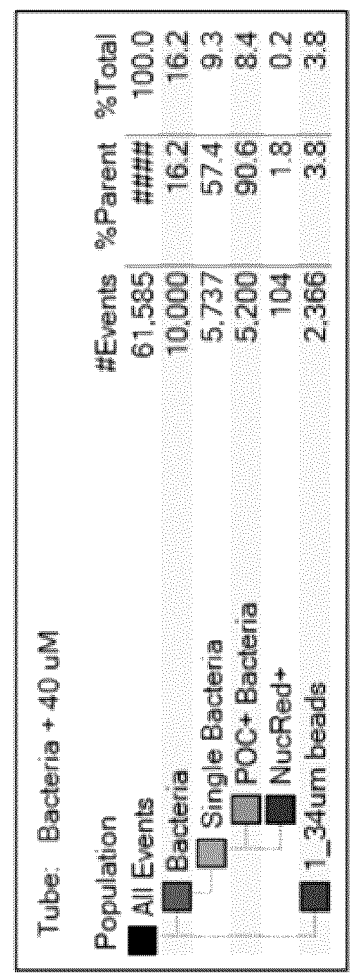
Figure 16:
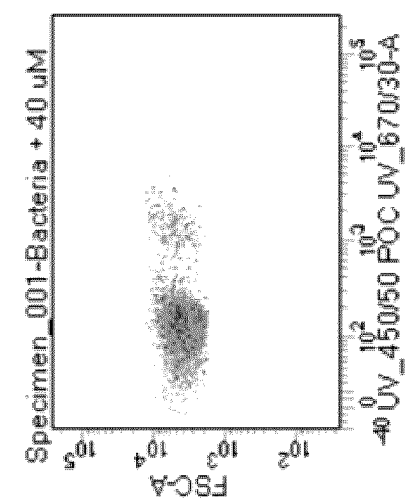
Figure 16:
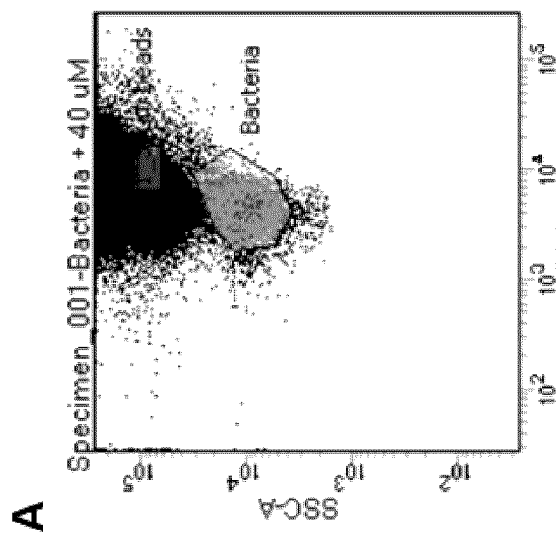
Figure 16:
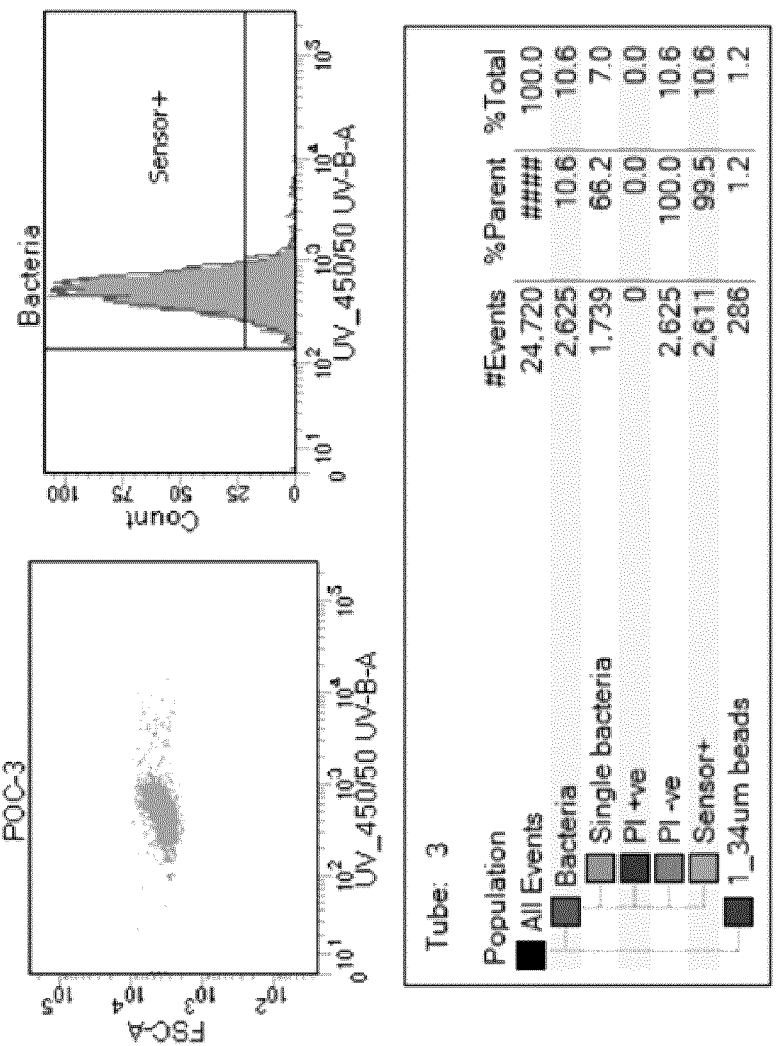
Figure 16:
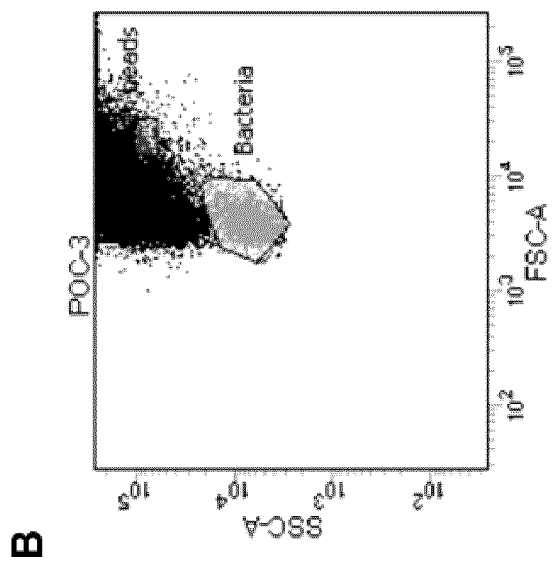
Figure 16:
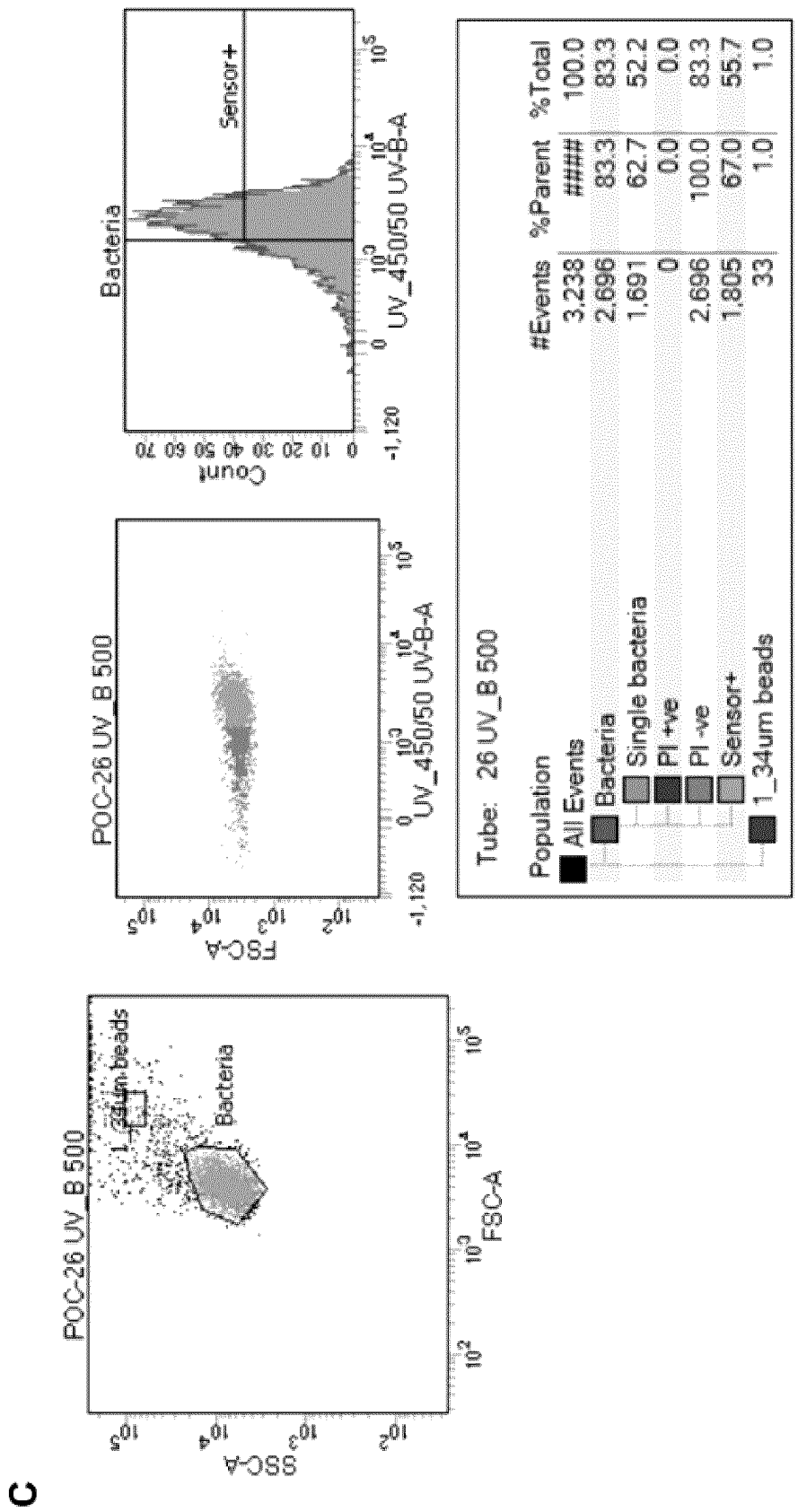
Figure 16:
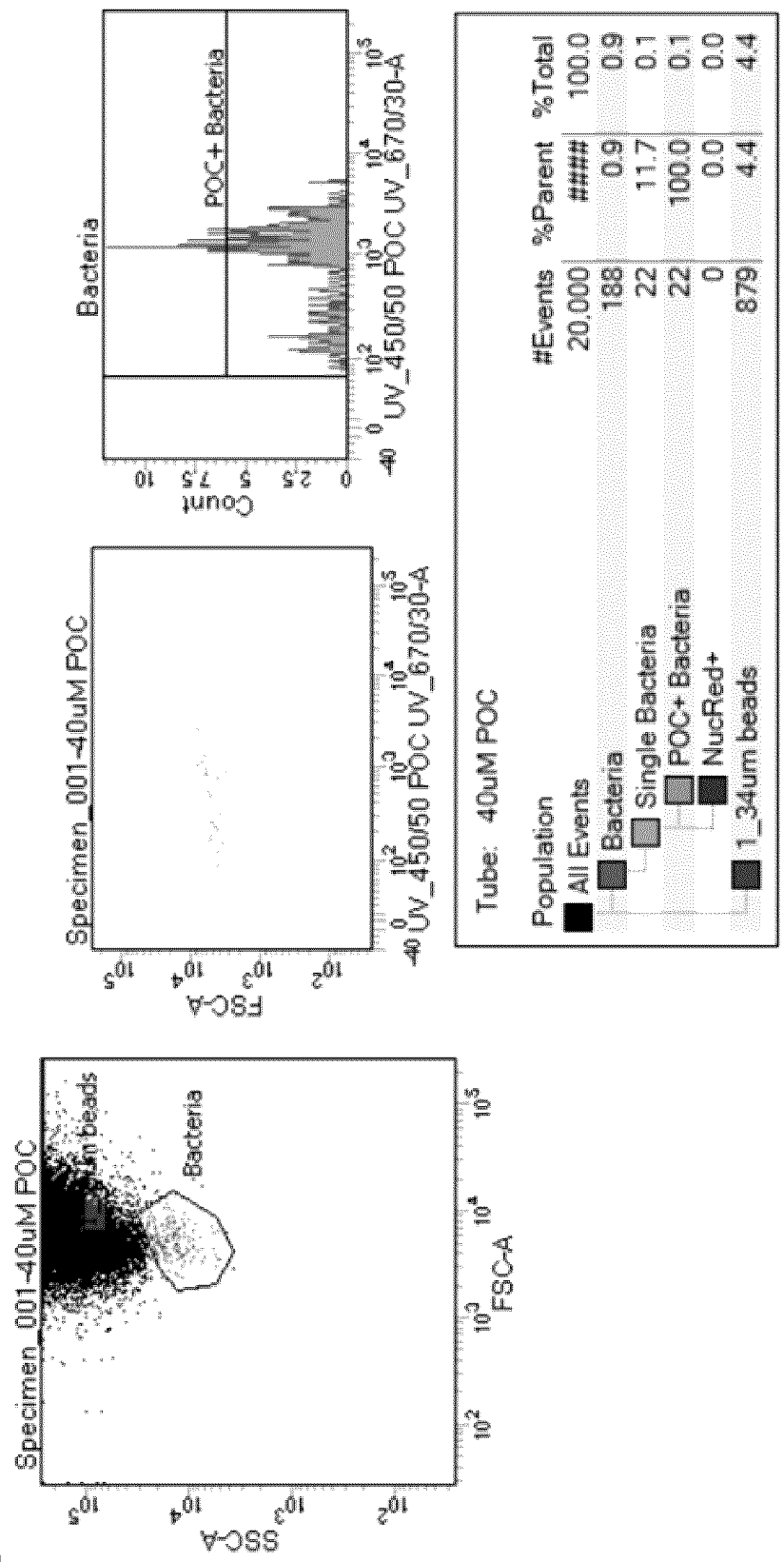
Figure 16:
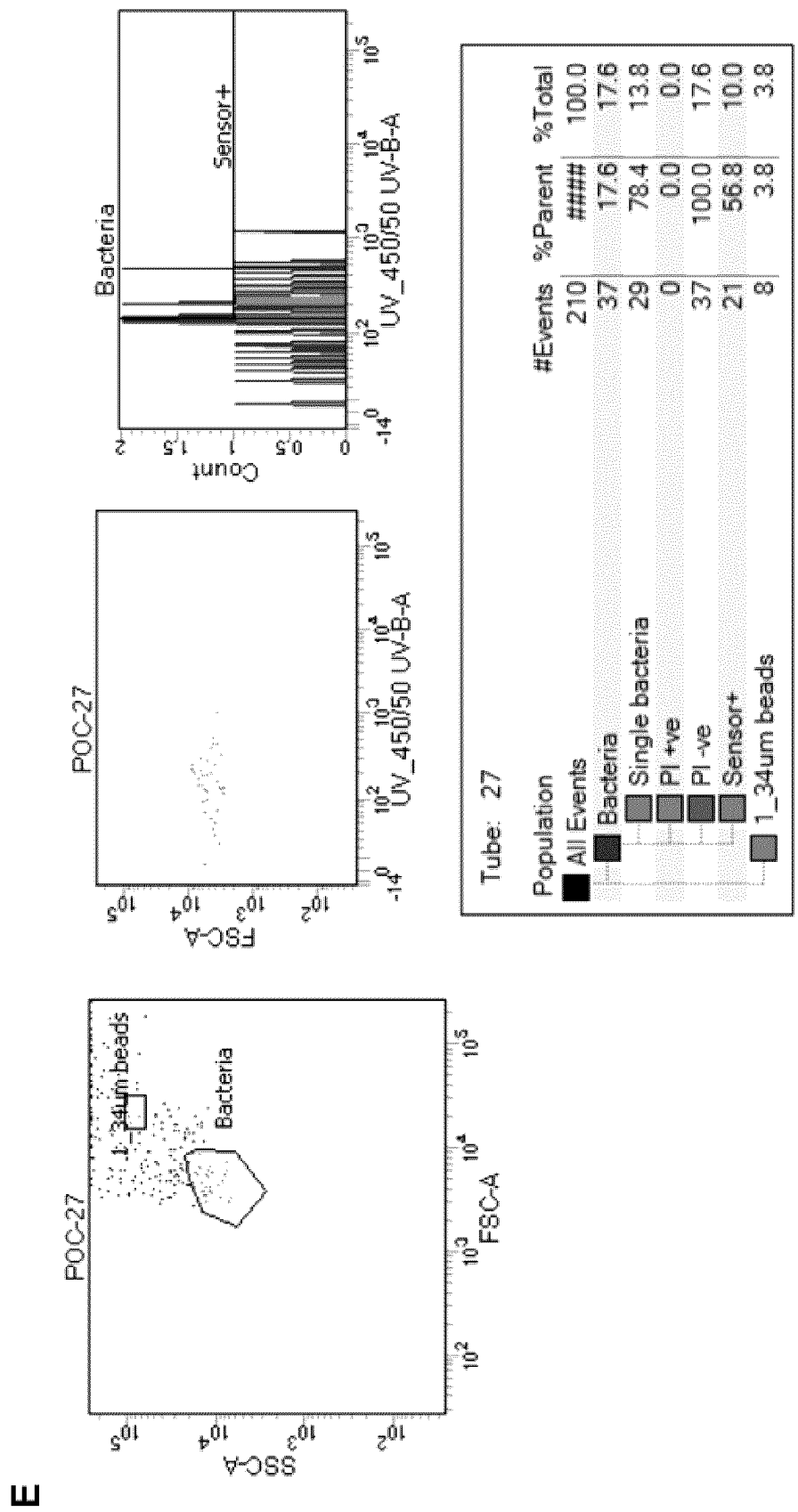

FIG. 16 shows bacteria flow cytometry results. Panel A shows *E. coli* K-12 BW25113 cells ($10^7$ CFU/mL) treated with 40 uM POC sensor (Sensor compound I-1). Sample run using UV laser (BD LSR Fortessa X20, emission: 450/50 nm) in 50 mM HEPES, 75 mM NaCl, 1% BSA, 0.4% DMSO, pH 7.5. Panel B shows *E. coli* K-12 BW25113 cells ($10^8$ CFU/mL) treated with 40 µM POC sensor (Sensor compound I-1). Sample run using UV laser (BD LSR Fortessa X20, emission: 450/50 nm) in 50 mM HEPES, 75 mM NaCl, 1% BSA, 0.4% DMSO, pH 7.5. Panel C shows *E. coli* K-12 BW25113 cells ($10^7$ CFU/mL) treated with 40 µM POC (Sensor compound I-1). Sample run using UV laser (BD LSR Fortessa X20, emission: 450/50 nm) in 50 mM HEPES, 75 mM NaCl, 1% BSA, 0.4% DMSO, pH 7.5. Panel D shows *E. coli* K-12 BW25113 cells ($10^8$ CFU/mL) treated with 40 uM Long Cyclam (Sensor compound I-6) sensor. Sample run using UV laser (BD LSR Fortessa X20, emission: 450/50 nm) in 50 mM HEPES, 75 mM NaCl, 1% BSA, 0.4% DMSO, pH 7.5. Panel E shows 40 µM POC sensor (Sensor compound I-1) without bacteria. Sample run using UV laser (BD LSR Fortessa X20, emission: 450/50 nm) in 50 mM HEPES, 75 mM NaCl, 1% BSA, 0.4% DMSO, pH 7.5. These results demonstrate that these sensors are suitable for the detection of bacteria using a flow cytometer.

Figure 17:
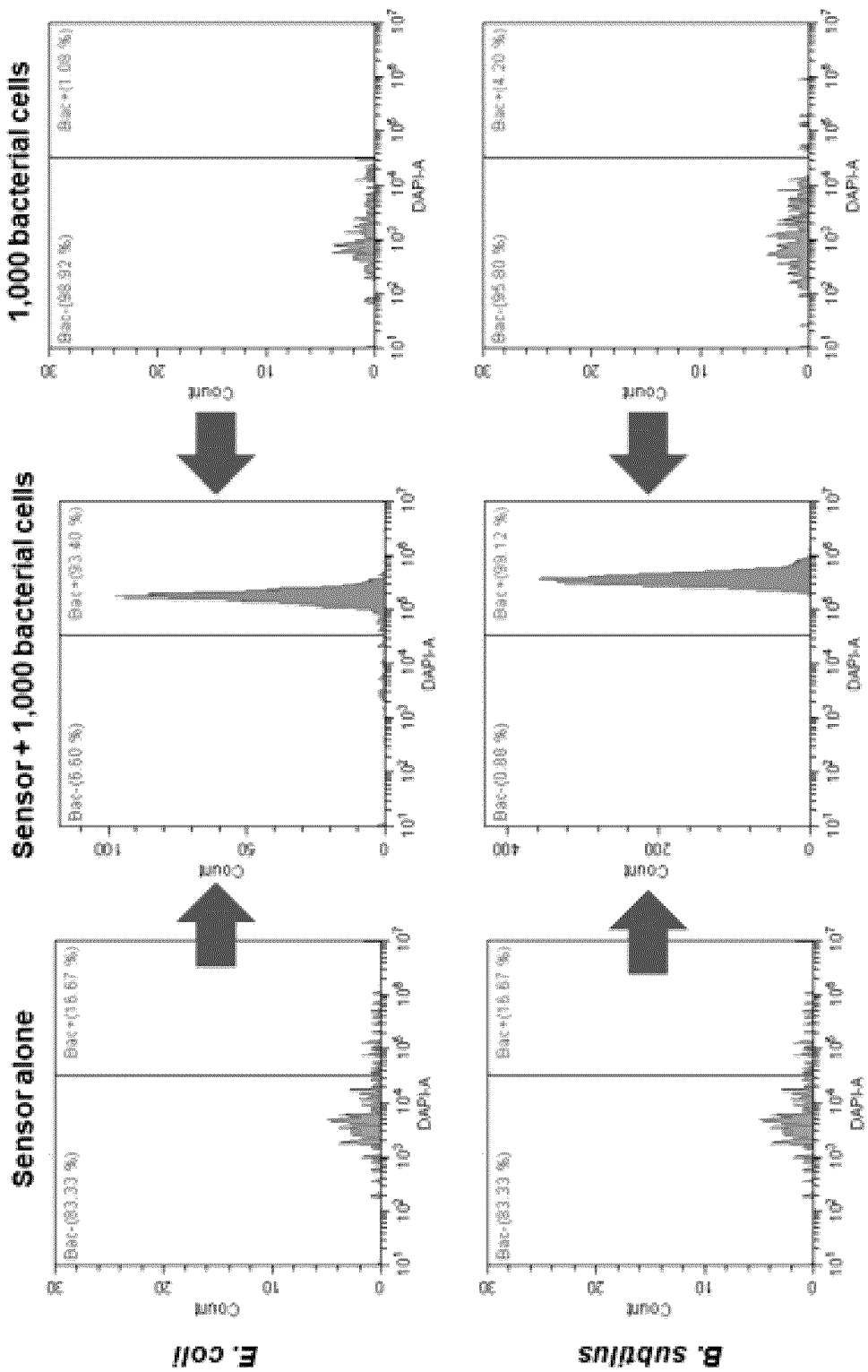
FIG. 17 shows bacteria flow cytometry results. The left panel shows fluorescence counts of exemplary sensor II-4 without bacteria. The right panel shows fluorescence counts of 1,000 bacteria cells (*E. coli* or *B. subtilis*) alone. The middle panel shows the shift of fluorescence counts when both the sensor and 1,000 bacteria cells are present. Gates were set off of unstained control. All samples run using near UV laser (exc: 375 nm, emi: 450/45 nm) and blue laser (exc: 488 nm, emi: 585/42 nm) (BeckmanCoulter, CytoFLEX S) in 50 mM HEPES, 75 mM NaCl, 1% BSA, 0.4% DMSO, pH 7.5.

FIG. 17 shows bacteria flow cytometry results. The left panel shows fluorescence counts of exemplary sensor II-4 without bacteria. The right panel shows fluorescence counts of 1,000 bacteria cells (*E. coli* or *B. subtilis*) alone. The middle panel shows the shift of fluorescence counts when both the sensor and 1,000 bacteria cells are present. Gates were set off of unstained control. All samples run using near UV laser (exc: 375 nm, emi: 450/45 nm) and blue laser (exc: 488 nm, emi: 585/42 nm) (BeckmanCoulter, CytoFLEX S) in 50 mM HEPES, 75 mM NaCl, 1% BSA, 0.4% DMSO, pH 7.5.

Example 44: LPS Detection

Figure 18:
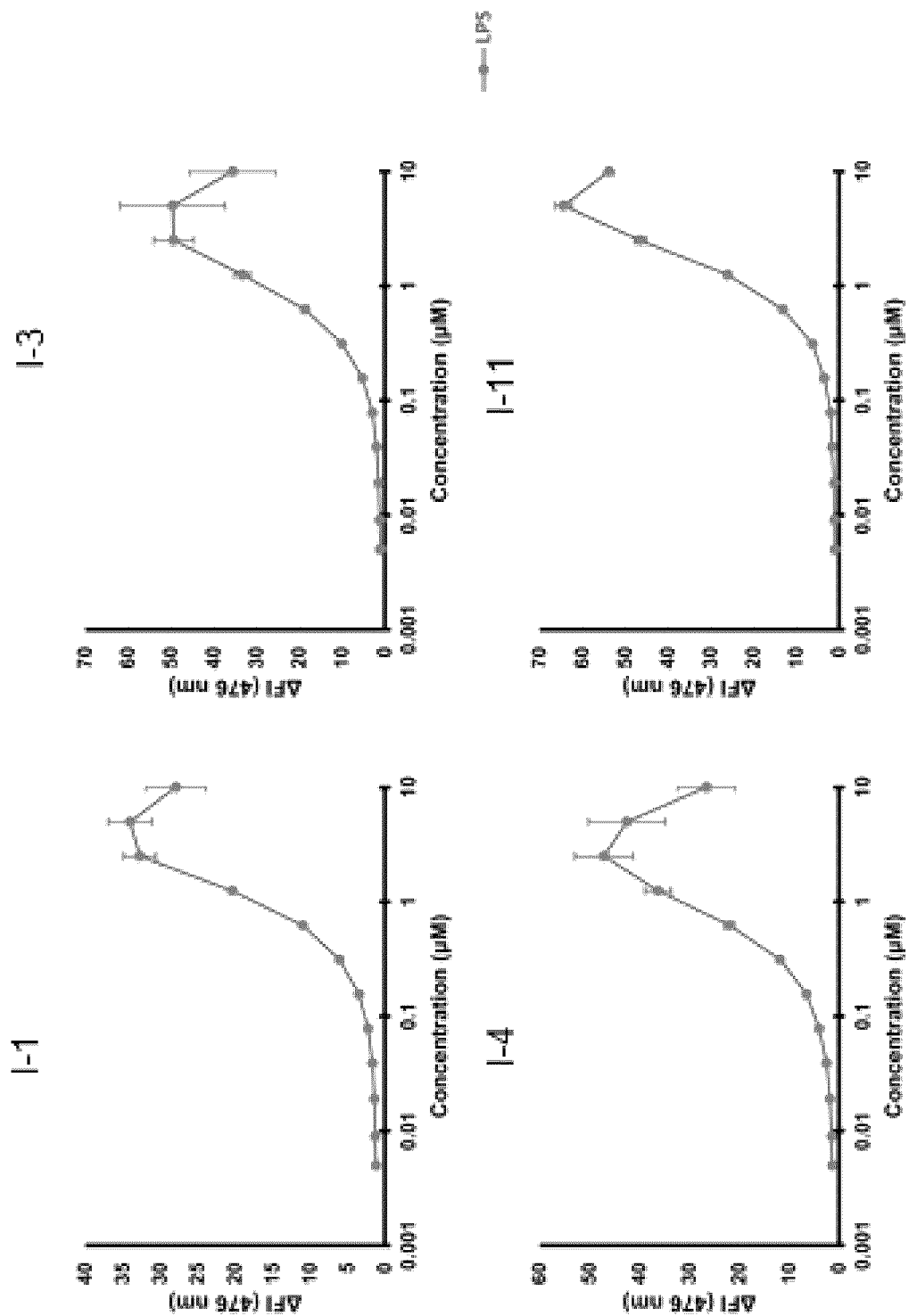
FIG. 18 shows the ΔFI of exemplary compounds I-1, I-3, I-4 and I-11 for LPS from *E. coli* O55:B5 (purchased from Sigma-Aldrich). All exemplary compounds are 10 μM in 50 mM HEPES, pH 7.5, 75 mM NaCl, 0.4-2.8% DMSO ($\lambda_{ex/em}$=350/476 nm). LPS was titrated from 10-0.005 μM in the same buffer (assuming a MW of 10 kDa). Sensor solutions were prepared from 10 mg/mL DMSO stocks in 50 mM HEPES buffer, pH 7.5, 75 mM NaCl and minimal DMSO (0.4-2.8%) at 20 μM The LPS solution was prepared at 20 μM in the same buffer without DMSO. The LPS solution was serially diluted 1:1 from 20 μM to 0.01 μM with buffer in a 96-well plate. In a 384-well black plate, 30 μL of sensor was combined with 30 μL of analyte (last row contained 30 μL buffer), the mixtures were incubated for 10 min away from light, and the fluorescence intensity was recorded at 476 nm (10 nm bandwidth) following excitation at 350 nm (5 nm bandwidth). Fluorescence intensities were used to calculate the excimer emission in response to LPS.

FIG. 18 shows the ΔFI of exemplary compounds I-1, I-3, I-4 and I-11 for LPS from *E. coli* O55:B5 (purchased from Sigma-Aldrich). All exemplary compounds were 10 µM in 50 mM HEPES, pH 7.5, 75 mM NaCl, 0.4-2.8% DMSO ($\lambda_{ex/em}$=350/476 nm). LPS was titrated from 10-0.005 µM in the same buffer (assuming a MW of 10 kDa). Sensor solutions were prepared from 10 mg/mL DMSO stocks in 50 mM HEPES buffer, pH 7.5, 75 mM NaCl and minimal DMSO (0.4-2.8%) at 20 µM. The LPS solution was prepared at 20 µM in the same buffer without DMSO. The LPS solution was serially diluted 1:1 from 20 µM to 0.01 µM with buffer in a 96-well plate. In a 384-well black plate, 30 µL of sensor was combined with 30 µL of analyte (last row contained 30 µL buffer), the mixtures were incubated for 10 min away from light, and the fluorescence intensity was recorded at 476 nm (10 nm bandwidth) following excitation at 350 nm (5 nm bandwidth). Fluorescence intensities were used to calculate the excimer emission in response to LPS.

Example 45: LTA Detection

Figure 19:
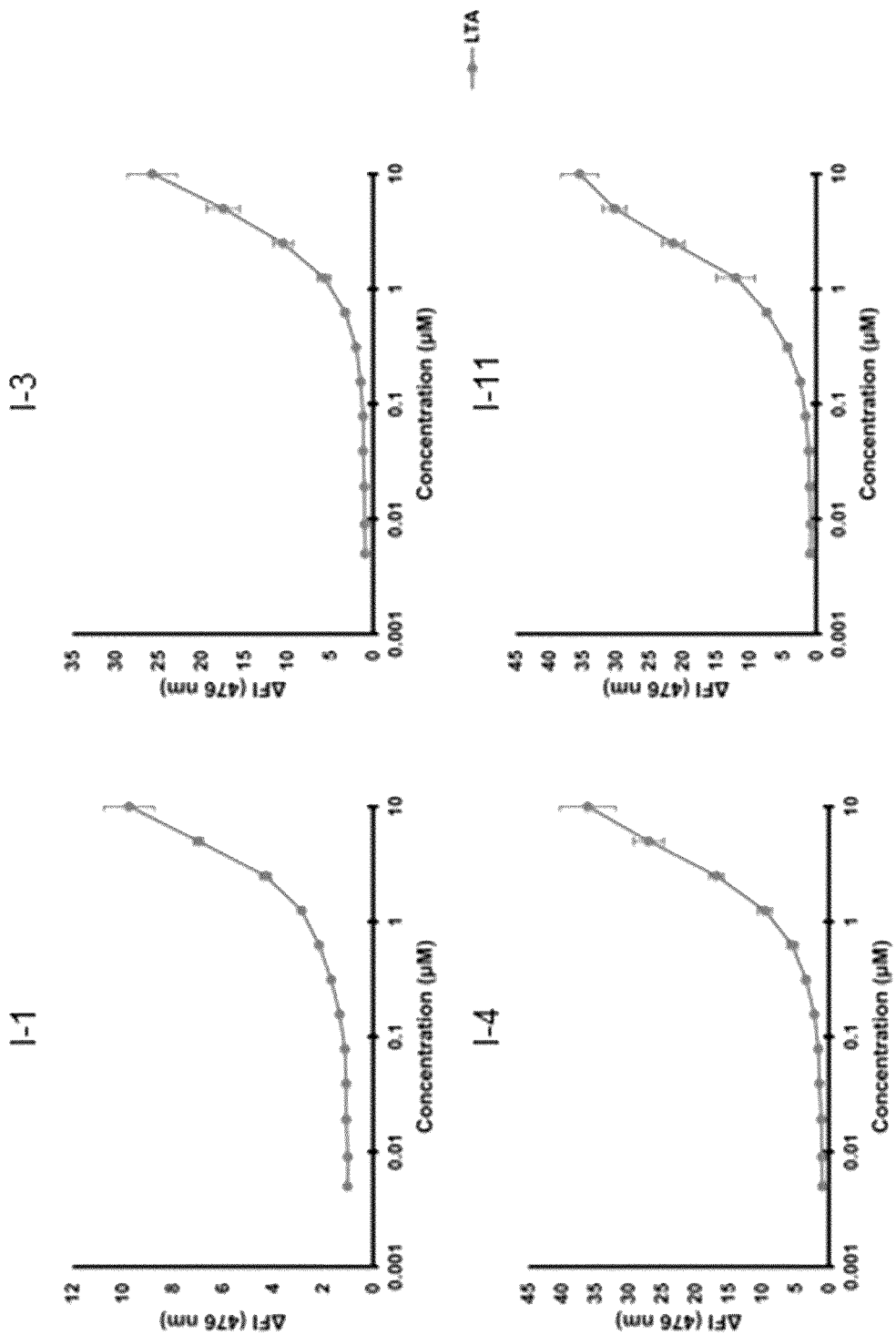
FIG. 19 shows the ΔFI of exemplary compounds I-1, I-3, I-4 and I-11 for LTA from *B. subtilis* (purchased from Sigma-Aldrich). All exemplary compounds are 10 μM in 50 mM HEPES, pH 7.5, 75 mM NaCl, 0.4-2.8% DMSO ($\lambda_{ex/em}$=350/476 nm). LTA is titrated from 10-0.005 μM in the same buffer (assuming a MW of 10 kDa). Sensor solutions were prepared from 10 mg/mL DMSO stocks in 50 mM HEPES buffer, pH 7.5, 75 mM NaCl and minimal DMSO (0.4-2.8%) at 20 μM. The LTA solution was prepared at 20 μM in the same buffer without DMSO. The LTA solution was serially diluted 1:1 from 20 μM to 0.01 μM with buffer in a 96-well plate. In a 384-well black plate, 30 μL of sensor was combined with 30 μL of analyte (last row contained 30 μL buffer), the mixtures were incubated for 10 min away from light, and the fluorescence intensity was recorded at 476 nm (10 nm bandwidth) following excitation at 350 nm (5 nm bandwidth). Fluorescence intensities were used to calculate the excimer emission in response to LTA.

FIG. 19 shows the ΔFI of exemplary compounds I-1, I-3, I-4 and I-11 for LTA from *B. subtilis* (purchased from Sigma-Aldrich). All exemplary compounds were 10 µM in 50 mM HEPES, pH 7.5, 75 mM NaCl, 0.4-2.8% DMSO ($\lambda_{ex/em}$=350/476 nm). LTA is titrated from 10-0.005 µM in the same buffer (assuming a MW of 10 kDa). Sensor solutions were prepared from 10 mg/mL DMSO stocks in 50 mM HEPES buffer, pH 7.5, 75 mM NaCl and minimal DMSO (0.4-2.8%) at 20 µM. The LTA solution was prepared at 20 µM in the same buffer without DMSO. The LTA solution was serially diluted 1:1 from 20 µM to 0.01 µM with buffer in a 96-well plate. In a 384-well black plate, 30 µL of sensor was combined with 30 µL of analyte (last row contained 30 µL buffer), the mixtures were incubated for 10 min away from light, and the fluorescence intensity was recorded at 476 nm (10 nm bandwidth) following excitation at 350 nm (5 nm bandwidth). Fluorescence intensities were used to calculate the excimer emission in response to LTA.

Example 46: Bacteria Mutant Strain Knockout Detection

Figure 20:
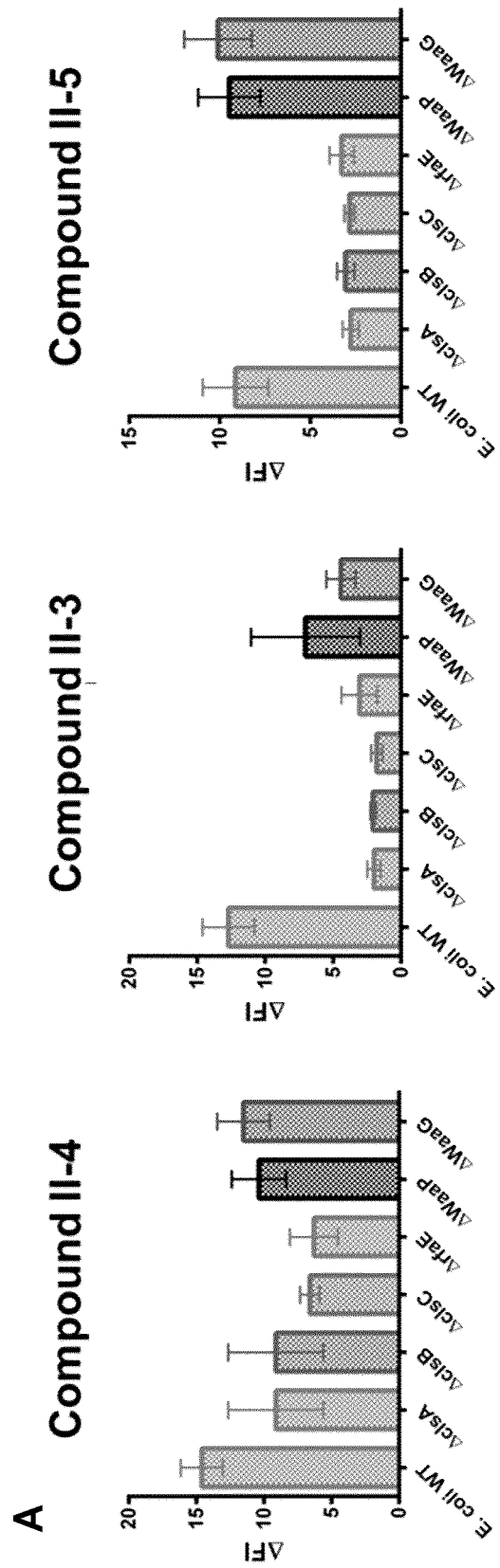
FIG. 20 shows mutant bacteria strain fluorimetry results. Panel A shows the fluorimetry results of mutant *E. coli* strains, including cardiolipin synthase knockouts (ΔclsA, ΔclsB, ΔclsC), LPS synthesis knockout (ΔrfaE) and LPS kinase knockouts (ΔWaaP, ΔwaaG) with exemplary compound II-4 (10 μM). Panel B shows the fluorimetry results of mutant *B. subtilis* strains, including cardiolipin synthase knockout (ΔclsA) and CRISPRi-mediated LTA knockout (ΔtagO) with exemplary compound II-4 (10 μM). The bacteria were at $10^8$ CFUs/mL in buffer (50 mM HEPES, pH 7.5, 75 mM NaCl, 0.4% DMSO). The mixtures were incubated for 10 min away from light, and the fluorescence intensity was recorded at 476 nm (10 nm bandwidth) following excitation at 350 nm (5 nm bandwidth). Fluorescence intensities were used to calculate the excimer emission in response to bacterial strains. Measurements were averaged over two triplicates.
Figure 20:
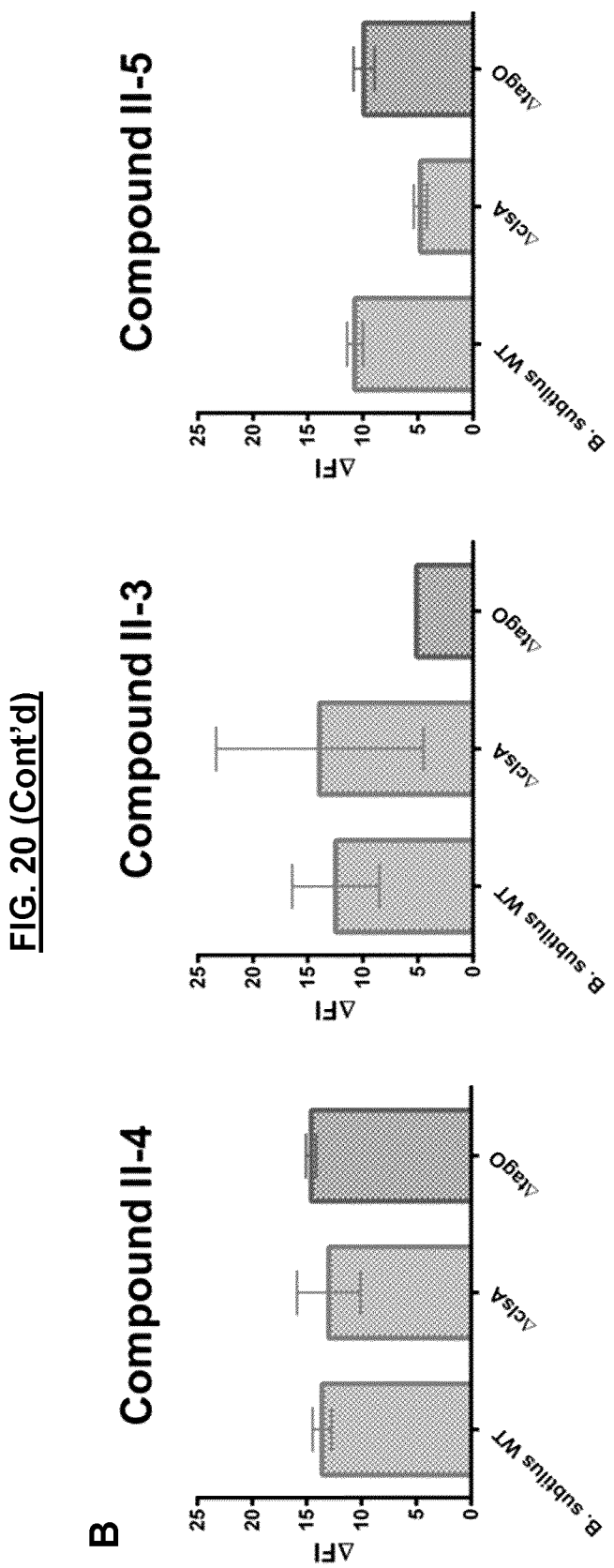

FIG. 20 shows mutant bacteria strain fluorimetry results. Panel A shows the fluorimetry results of WT and mutant *E. coli* strains, including cardiolipin synthase knockouts (ΔclsA, ΔclsB, ΔclsC), LPS synthesis knockout (ΔrfaE) and LPS kinase knockouts (ΔWaaP, ΔwaaG) with exemplary compound II-4 (10 µM). Panel B shows the fluorimetry results of WT and mutant *B. subtilis* strains, including cardiolipin synthase knockout (ΔclsA) and CRISPRi-mediated LTA knockout (ΔtagO) with exemplary compound II-4 (10 µM). The bacteria were at $10^8$ CFUs/mL in buffer (50 mM HEPES, pH 7.5, 75 mM NaCl, 0.4% DMSO). The mixtures were incubated for 10 min away from light, and the fluorescence intensity was recorded at 476 nm (10 nm bandwidth) following excitation at 350 nm (5 nm bandwidth). Fluorescence intensities were used to calculate the excimer emission in response to bacterial strains. Measurements were averaged over two triplicates.

The results of fluorimetry experiments with mutant bacteria strains show insight into the mechanism of action of the cyclen and cyclam-based sensors. Compared to the WT strains, exemplary compound II-4 showed the least changes in fluorescence, but a general decrease in fluorescence fold intensity for the E. coli strains, and no changes for B. subtilis strains. However, exemplary compounds II-3 and II-5 show that for E. coli strains, knocking out the cardiolipin synthases has the greatest effect on fluorescence fold, while the LPS kinases show little to no change. These results suggest that the mechanism of binding of the sensors towards the model gram-negative strain is membrane-dependent. Additionally, the LPS synthesis knockout (ΔrfaE) also showed fluorescence fold changes across all three sensors, presumably due to the knockout greatly disrupting the natural morphology of the bacterial membrane. For the gram-positive B. subtilis mutant strains, no clear trend could be seen. However, the fact that compound II-4 showed no fluorescence fold change against the three strains suggests that the mechanism might not be membrane-dependent, but partially or separately entirely. These results coincide with fluorescence microscopy, where E. coli cells were stained brightly on the membrane (FIG. 12), while B. subtilis cells were stained on distinct foci on or within the cells (FIG. 13).

Example 47: Apoptosis Detection

MOLM-13 cells were cultured in Roswell Park Memorial Institute (RPMI)-1640 Medium supplemented with 10% FCS and 1% antibiotic/antimycotic (Gibco, cat. 15240062).

Figure 21:
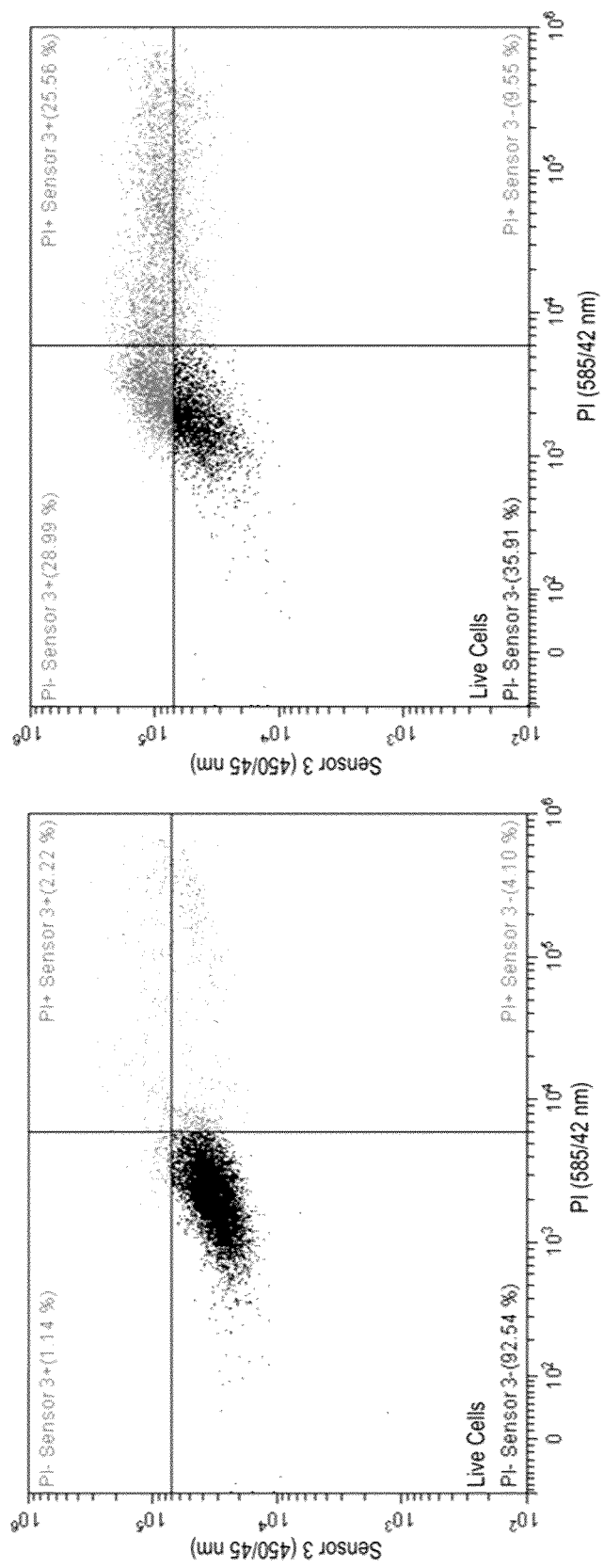
FIG. 21 shows cell apoptosis flow cytometry results. Panel A shows flow cytometry results of untreated (left) and camptothecin (10 μM, 7 hr) treated (right) MOLM-13 cells ($1.0 \times 10^6$ cells) after treatment with both exemplary compound I-3 (50 μM final) and propidium iodide (0.02 μg/μL). Panel B shows flow cytometry results of untreated (left) and camptothecin (10 μM, 7 hr) treated (right) MOLM-13 cells ($1.0 \times 10^6$ cells) after treatment with both PSVue™380 (90.9 μM final) and propidium iodide (0.02 μg/μL). Gates were set off of single stain samples. All samples run using near UV laser (exc: 375 nm, emi: 450/45 nm) and blue laser (exc: 488 nm, emi: 585/42 nm) (BeckmanCoulter, CytoFLEX S) in 50 mM HEPES, 75 mM NaCl, 1% BSA, 0.4% DMSO, pH 7.5.
Figure 21:
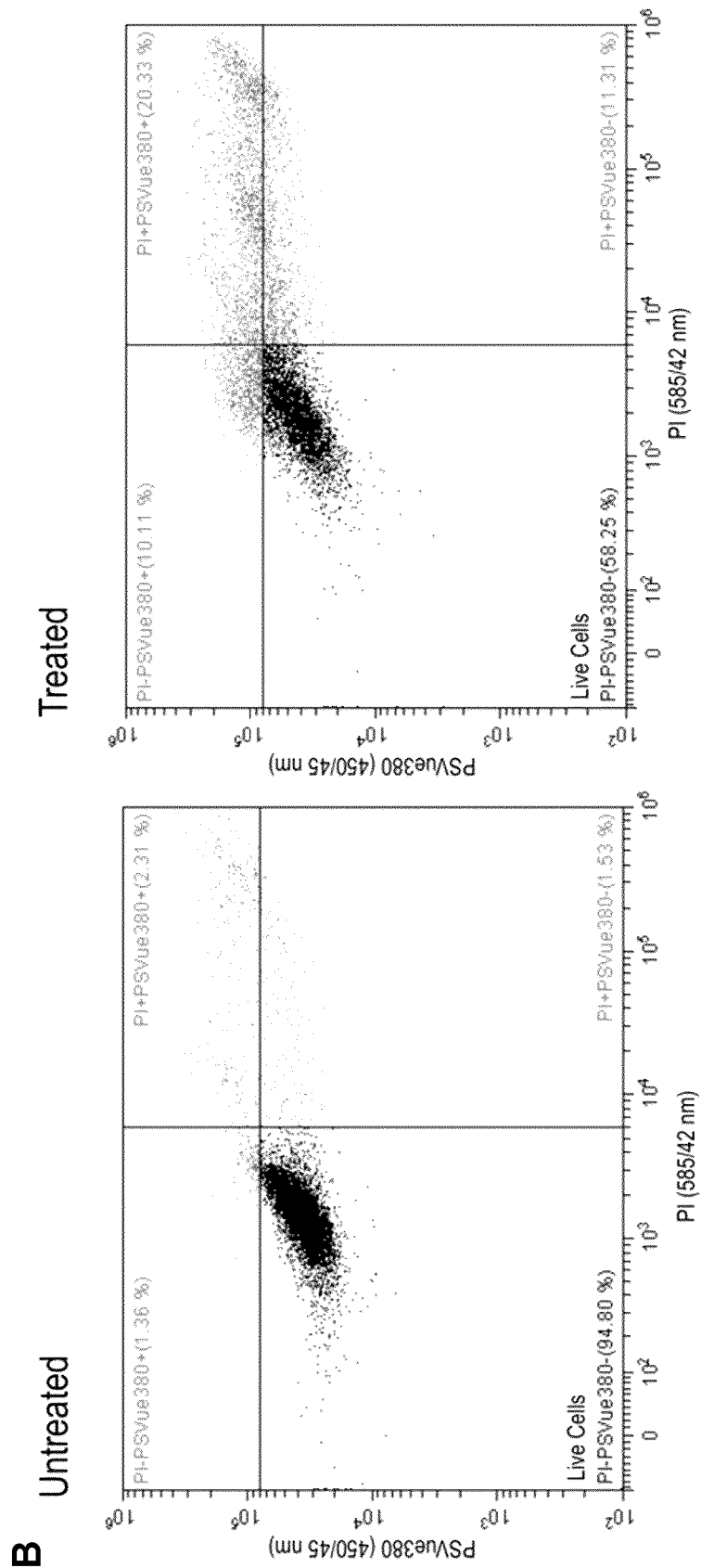

FIG. 21 shows apoptosis flow cytometry results. MOLM-13 cells were cultured to a density of $5.0 \times 10^5$ cells/mL in regular media and transferred to 6-well tissue culture treated plates ($1.0 \times 10^6$ cells/well). Treated Cells. Camptothecin (100 μL of 210 μM camptothecin in media) was added to a final concentration of 10 μM (1% DMSO final). Untreated Cells. DMSO Vehicle (100 μL DMSO in media) was added (1% DMSO final). All cells were then incubated at 37° C. for 7 hrs. Cells were then washed once with HEPES buffer (50 mM HEPES, 75 mM NaCl, 1% BSA, 0.4% DMSO, pH 7.5) and then re-suspended in HEPES buffer for staining. Cell samples were then treated simultaneously with either 1) exemplary compound I-3 (in HEPES buffer, final concentration of 50 μM), and propidium iodide (0.02 μg/μL) or 2) PSVue™380 (in HEPES buffer, final concentration of 90.9 μM as previously reported[39]) and propidium iodide (0.02 μg/μL). Samples were then incubated for 15 min away from light at 37° C. and were then analyzed by flow cytometry (CytoFLEX S, BeckmanCoulter) using the near UV laser (exc: 375 nm, emi: 450/45 nm) and blue laser (exc: 488 nm, emi: 585/42 nm). Gates were set off of single stain samples. Results demonstrate that for camptothecin treated cells, exemplary compound I-3 detects a population of cells, undetected by the dead cell stain propidium iodide. These cells are likely early apoptotic cells, as a similar population of cells is detected by PSVue™380, which has been shown to detect early apoptotic cells under similar conditions.[39]

LIST OF REFERENCES

1. G. van Meer, D. R. Voelker and G. W. Feigenson, Nat. Rev. Mol. Cell Biol., 2008, 9, 112-124.
2. R. A. Chaurio, C. Janko, L. E. Munoz, B. Frey, M. Herrmann and U. S. Gaipl, Molecules, 2009, 14, 4892-4914.
3. J. Li, X. Wang, T. Zhang, C. Wang, Z. Huang, X. Luo and Y. Deng, Asian J. Pharm. Sci., 2015, 10, 81-98.
4. J. N. Israelachvili, Intermolecular and surface forces, Academic Press, 2011.
5. P. Cullis, M. Hope and C. Tilcock, Chem. Phys. Lipids, 1986, 40, 127-144.
6. M. Bohdanowicz and S. Grinstein, Physiol. Rev., 2013, 93, 69-106.
7. R. M. Epand and R. F. Epand, Biochim. Biophys. Acta—Biomembr., 2009, 1788, 289-294.
8. C. Stace and N. Ktistakis, Biochim. Biophys. Acta—Mol. Cell Biol. Lipids, 2006, 1761, 913-926.
9. K. Athenstaedt and G. Daum, Eur. J. Biochem., 1999, 266, 1-16.
10. V. A. Sciorra and A. J. Morris, Mol. Biol. Cell, 1999, 10, 3863-76.
11. Y. Nishizuka, FASEB J., 1995, 9, 484-96.
11a. Andresen Bradley T, Rizzo Mark A, Shome Kuntala and Romero Guillermo (2002), The role of phosphatidic acid in the regulation of the Ras/MEK/Erk signaling cascade, FEBS Letters, 531.
11b. A., & Chen, J. (2001). Phosphatidic acid-mediated mitogenic activation of mTOR signaling. Science, 294 (5548), 1942-5.
12. W. Zhao, T. Róg, A. A. Gurtovenko, I. Vattulainen and M. Karttunen, Biochimie, 2008, 90, 930-938.
13. W. Dowhan, Annu. Rev. Biochem., 1997, 66, 199-232.
14. C. Osman, D. R. Voelker and T. Langer, J. Cell Biol., 2011, 192, 7-16.
15. D. Lopez, Chem. Phys. Lipids, 2015, 192, 3-11.
16. T. Lemmin, C. Bovigny, D. Lançon and M. Dal Peraro, J. Chem. Theory Comput., 2013, 9, 670-678.
17. P. A. Leventis and S. Grinstein, Annu. Rev. Biophys., 2010, 39, 407-427.
18. B. Fadeel and D. Xue, Crit. Rev. Biochem. Mol. Biol., 2009, 44, 264-77.
19. S. Elmore, Toxicol. Pathol., 2007, 35, 495-516.
20. K. Segawa, S. Kurata, Y. Yanagihashi, T. R. Brummelkamp, F. Matsuda and S. Nagata, Science (80-.)., 2014, 344, 1164-1168.
21. M. Olson and L. Julian, Cell Health Cytoskelet., 2015, Volume 7, 133.
22. N. Anderson and J. Borlak, FEBS Lett., 2006, 580, 5533-5540.
23. M. J. Reasor, K. L. Hastings and R. G. Ulrich, Expert Opin. Drug Saf., 2006, 5, 567-583.
24. N. Liu, E. A. Tengstrand, L. Chourb and F. Y. Hsieh, Toxicol. Appl. Pharmacol., 2014, 279, 467-476.
25. E. Baronas, J. Lee, C. Alden and F. Hsieh, Toxicol. Appl. Pharmacol., 2007, 218, 72-78.
25a. Mills, Gordon B., and Wouter H. Moolenaar. "The emerging role of lysophosphatidic acid in cancer." Nature Reviews Cancer, vol. 3, no. 8, 2003, p. 582+
25b. Andresen Bradley T, Rizzo Mark A, Shome Kuntala and Romero Guillermo (2002), The role of phosphatidic acid in the regulation of the Ras/MEK/Erk signaling cascade, FEBS Letters, 531.
25c. A., & Chen, J. (2001). Phosphatidic acid-mediated mitogenic activation of mTOR signaling. Science, 294 (5548), 1942-5.

25d. Xu Y, Shen Z, Wiper D W, Wu M, Morton R E, Elson P, Kennedy A W, Belinson J, Markman M, Casey G. Lysophosphatidic Acid as a Potential Biomarker for Ovarian and Other Gynecologic Cancers. JAMA. 1998; 280 (8):719-723.
26. Vermes, C. Haanen, H. Steffens-Nakken and C. Reutelingsperger, J. Immunol. Methods, 1995, 184, 39-51.
27. V. Gerke and S. E. Moss, Physiol. Rev., 2002, 82, 331-371.
28. P. Williamson, S. van den Eijnde and R. A. Schlegel, 2001, pp. 339-364.
29. M. van Engeland, L. J. W. Nieland, F. C. Ramaekers, B. Schutte and C. P. M. Reutelingsperger, Cytom., 1998, 31, 1-9.
30. B. Pläsier, D. R. Lloyd, G. C. Paul, C. R. Thomas and M. Al-Rubeai, J. Immunol. Methods, 1999, 229, 81-95.
31. J. A. Barnes and A. V Gomes, Mol. Cell. Biochem., 2002, 231, 1-7.
32. D. Arboledas, N. Olmo, M. A. Lizarbe and J. Turnay, FEBS Lett., 1997, 416, 217-20.
33. R. G. Hanshaw and B. D. Smith, Bioorg. Med. Chem., 2005, 13, 5035-5042.
34. D. Kamp, T. Sieberg and C. W. Haest, Biochemistry, 2001, 40, 9438-46.
35. A. Ojida, Y. Mito-oka, M. Inoue and I. Hamachi, J. Am. Chem. Soc., 2002, 124, 6256-6258.
36. D. R. Rice, K. J. Clear, B. D. Smith, L. Watkins, P. E. Thorpe, C. C. Barnett, P. E. Thorpe, J. B. Fleming, R. A. Brekken, D. von Laer, B. Brachvogel, E. Poschl, M. Herrmann, U. S. Gaipl, D. Lacombe, J. Verweij, E. Miyoshi, N. Taniguchi, D. Sheff, W. I. Lencer, T. Taguchi and H. Arai, Chem. Commun., 2016, 52, 8787-8801. 16
37. A. V Koulov, K. A. Stucker, C. Lakshmi, J. P. Robinson and B. D. Smith, Cell Death Differ., 2003, 10, 1357-1359.
38. C. Lakshmi, R. G. Hanshaw and B. D. Smith, 2004.
39. A. V. Koulov, R. G. Hanshaw, K. A. Stucker, C. Lakshmi and B. D. Smith, Isr. J. Chem., 2005, 45, 373-379.
40. W. M. Leevy, J. R. Johnson, C. Lakshmi, J. Morris, M. Marquez and B. D. Smith, Chem. Commun., 2006, 1595.
41. W. M. Leevy, S. T. Gammon, H. Jiang, J. R. Johnson, D. J. Maxwell, E. N. Jackson, M. Marquez, A. David Piwnica-Worms and B. D. Smith, J. Am. Chem. Soc., 2006, 128, 16476-16477.
42. R. G. Hanshaw, C. Lakshmi, T. N. Lambert, J. R. Johnson and B. D. Smith, Chem Bio Chem, 2005, 6, 2214-2220.
43. W. M. Leevy, S. T. Gammon, J. R. Johnson, A. J. Lampkins, H. Jiang, M. Marquez, D. Piwnica-Worms, M. A. Suckow and B. D. Smith, Bioconjug. Chem., 2008, 19, 686-692.
44. S. Klaschik, L. E. Lehmann, A. Raadts, M. Book, A. Hoeft and F. Stuber, J. Clin. Microbiol., 2002, 40, 4304-7
45. Afshari, A. et al. Bench-to-bedside review: Rapid molecular diagnostics for bloodstream infection—a new frontier? Crit. Care 16, 222 (2012).
46. Lee, A., Mirrett, S., Reller, L. B. & Weinstein, M. P. Detection of bloodstream infections in adults: how many blood cultures are needed? J. Clin. Microbiol. 45, 3546-8 (2007).
47. Kang, D.-K. et al. Rapid detection of single bacteria in unprocessed blood using Integrated Comprehensive Droplet Digital Detection. Nat. Commun. 5, 5427 (2014).

The invention claimed is:

1. A method of detecting negatively charged phosphate-containing membrane components comprising:
   (a) combining a solution of a sample suspected of comprising negatively charged phosphate-containing membrane components with a solution comprising a compound of Formula V, or a metal chelate salt thereof:

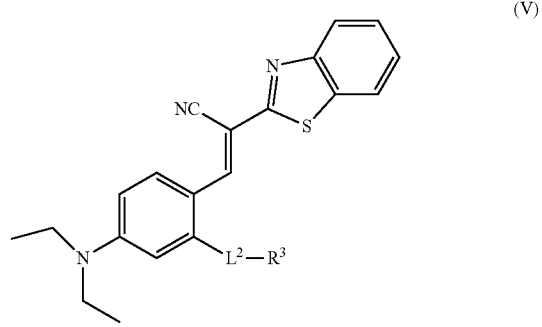

wherein $L^2$ is a linker group selected from $C_{1-20}$alkylene, $C_{2-20}$alkenylene, $C_{2-20}$alkynylene and $C_{3-10}$-cycloalkylene, or a combination thereof, each of which is optionally oxo-substituted (=O) 1-3 times, and in which 1-3 carbon atoms are optionally replaced with a heteromoiety selected from NH, O, S and Si; and $R^3$ is selected from

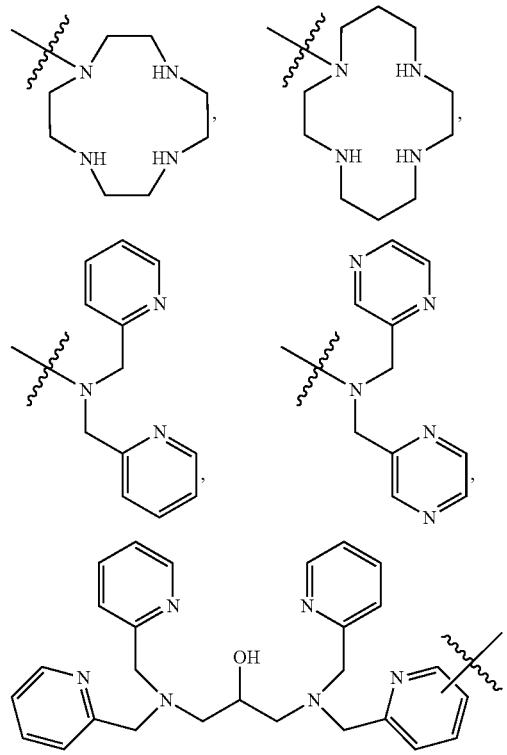

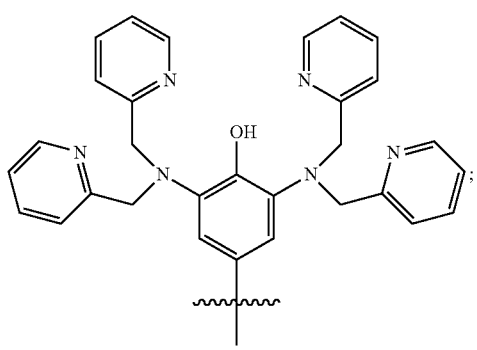

and (b) detecting a fluorescence signal;

wherein detection of the fluorescence signal in (b) indicates that the sample comprises negatively charged phosphate-containing membrane components.

2. The method of claim 1, wherein the sample is an extract from a bacterial, yeast, insect or mammalian cell line; (b) a bodily sample; or (c) urine, synovial fluid or blood, or any sample that contains or is suspected of comprising negatively charged phosphate-containing membrane components.

3. A compound of Formula V, or a metal chelate salt thereof:

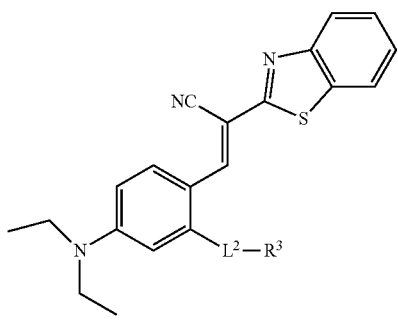

(V)

wherein

L² is a linker group selected from $C_{1-20}$alkylene, $C_{2-20}$alkenylene, $C_{2-20}$alkynylene and $C_{3-10}$-cycloalkylene, or a combination thereof, each of which is optionally oxo-substituted (=O) 1-3 times, and in which 1-3 carbon atoms are optionally replaced with a heteromoiety selected from NH, O, S and Si; and R³ is selected from

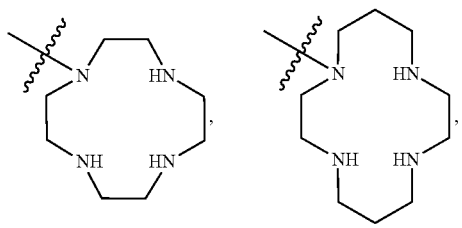

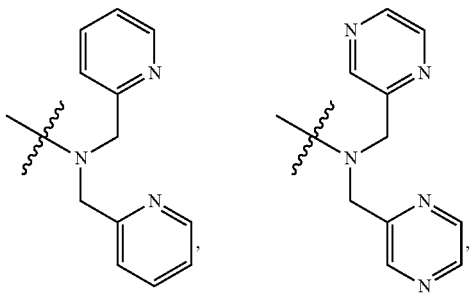

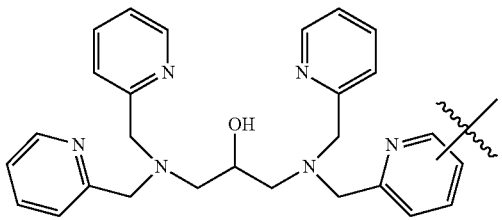

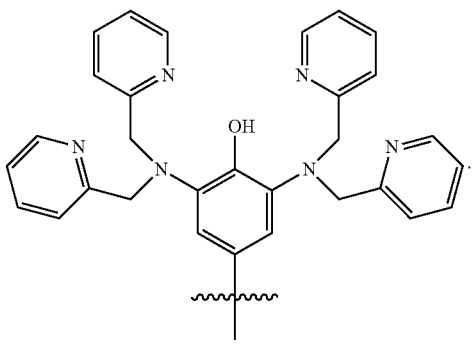

and

4. The compound of claim 3, wherein L² is selected from:

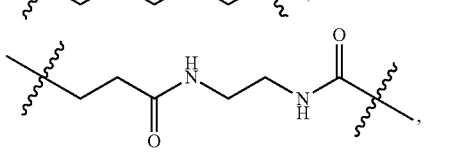

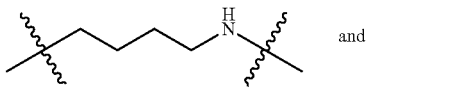 and

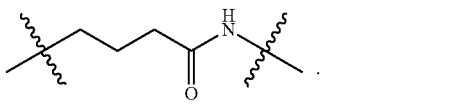

5. The compound of claim 3, wherein the metal is $Zn^{2+}$.

6. The compound of claim 5, wherein the compound is

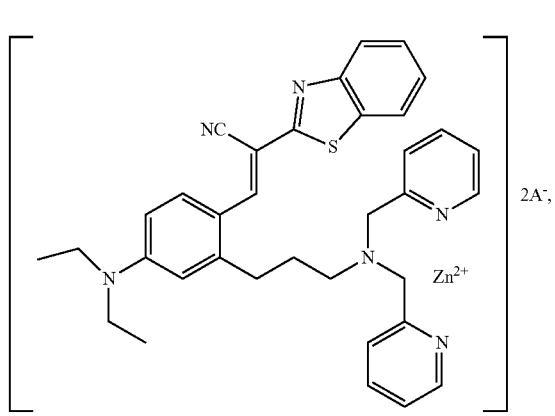

or

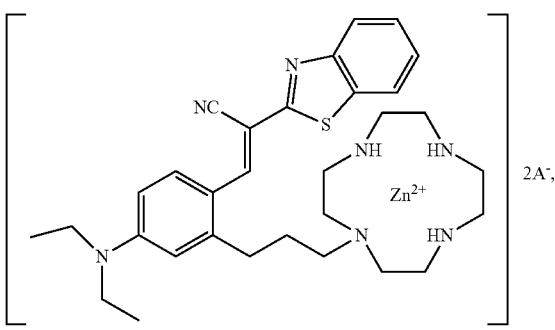

wherein A is a counteranion.

7. The compound of claim 6, wherein A is $CF_3SO_3^-$, $Cl^-$, $Br^-$, $I^-$, $CH_3COO^-$, $HPO_3^-$, $HSO_4^-$, $SO_4^{2-}$ or $NO_3^-$.

8. The method of claim 1, wherein the metal is $Zn^{2+}$.

9. The method of claim 8, wherein the compound is

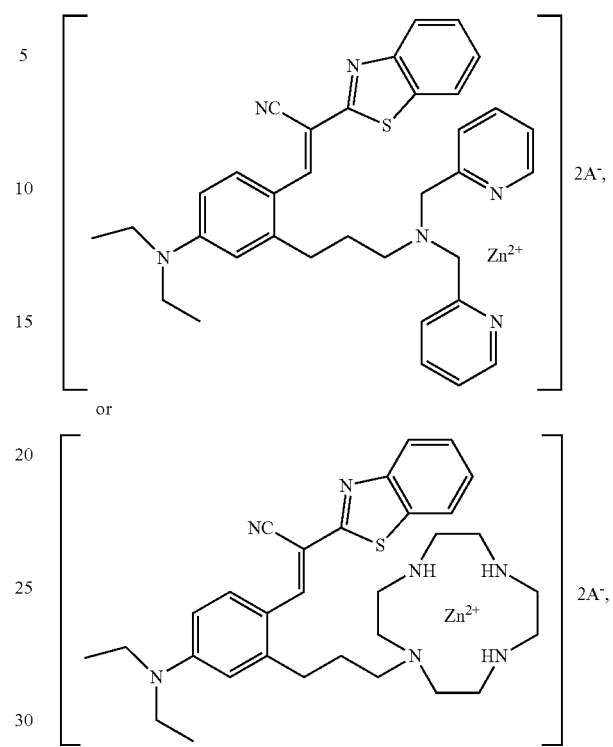

wherein A is a counteranion.

10. The method of claim 9, wherein A is $CF_3SO_3^-$, $Cl^-$, $Br^-$, $Cl^-$, $I^-$, $CH_3COO^-$, $HPO_3^-$, $HSO_4^-$, $SO_4^{2-}$ or $NO_3^-$.

11. The method of claim 2, wherein the mammalian cell line is a human cell line.

* * * * *

UNITED STATES PATENT AND TRADEMARK OFFICE
CERTIFICATE OF CORRECTION

PATENT NO. : 11,851,410 B2
APPLICATION NO. : 16/652733
DATED : December 26, 2023
INVENTOR(S) : Patrick Thomas Gunning et al.

Page 1 of 1

It is certified that error appears in the above-identified patent and that said Letters Patent is hereby corrected as shown below:

In the Claims

In Claim 4, at Column 68, Line 50, amend  to

In Claim 4, at Column 68, Line 55, amend 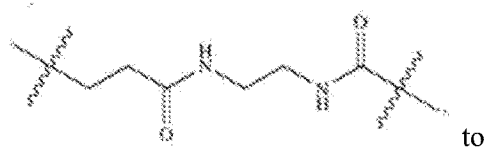 to

Signed and Sealed this
Eleventh Day of June, 2024

Katherine Kelly Vidal
*Director of the United States Patent and Trademark Office*